(12) United States Patent
Chen et al.

(10) Patent No.: US 7,482,157 B2
(45) Date of Patent: Jan. 27, 2009

(54) MONACOLIN K BIOSYNTHESIS GENES

(75) Inventors: Yi-Pei Chen, Yingge Township, Taipei County (TW); Li-Ling Liaw, Hsinchu (TW); Chun-Lin Wang, Hsinchu (TW); Chung-Tsai Lee, Dacun Township, Changhua County (TW); Ing-Er Hwang, Jhudong Township, Hsinchu County (TW); Ching-Ping Tseng, Hsinchu (TW); Gwo-Fang Yuan, Hsinchu (TW)

(73) Assignee: Food Industry Research & Development Institute, Hsinchu (TW)

( * ) Notice: Subject to any disclaimer, the term of this patent is extended or adjusted under 35 U.S.C. 154(b) by 479 days.

(21) Appl. No.: 11/022,243

(22) Filed: Dec. 23, 2004

(65) Prior Publication Data

US 2005/0227262 A1  Oct. 13, 2005

(51) Int. Cl.
| | |
|---|---|
| C12N 15/16 | (2006.01) |
| C12N 15/14 | (2006.01) |
| C12N 1/15 | (2006.01) |
| C12N 1/16 | (2006.01) |
| C12N 1/21 | (2006.01) |
| C12N 15/31 | (2006.01) |
| C12N 15/54 | (2006.01) |
| C07H 21/04 | (2006.01) |

(52) U.S. Cl. .............. 435/325; 435/252.3; 435/254.2; 435/254.11; 435/419; 536/23.1

(58) Field of Classification Search ............... None
See application file for complete search history.

(56) References Cited

U.S. PATENT DOCUMENTS

| 6,221,641 B1 | 4/2001 | Khosla et al. | ............... 435/193 |
| 6,391,583 B1 * | 5/2002 | Hutchinson et al. | ........ 435/69.1 |
| 6,391,594 B1 | 5/2002 | Khosla et al. | .............. 435/91.4 |

FOREIGN PATENT DOCUMENTS

EP  1325929 A2  9/2003

OTHER PUBLICATIONS

Abe et al., Mol. Genet. Genom., 2002, 267:636-646.*
"Monacolin K, A New Hypocholesterolemic Agent Produced by A *Monascus* Species" Endo; Aug. 1979; The Journal of Antiobiotics.
"Dihydromonacolin L and Monacolin X, New Metabolites Those Inhibit Cholesterol Biosynthesis" Endo et al.; Jul. 1984; The Journal of Antibiotics.
"Monacolins J and L, New Inhibitors of Cholesterol Biosynthesis Produced by *Monascus Ruber*" Endo et al.; Mar. 1985; The Journal of Antibiotics.
"Monacolin M, A New Inhibitor of Cholesterol Biosynthesis" Endo et al.; Dec. 1986.
"Biosynthesis of Monacolins: Conversion of Monacolin L to Monacolin J by a Monooxygenase of *Monascus Ruber*" Komagata et al.; Oct. 1988; The Journal of Antibiotics.
"Biosynthesis of Fatty Acid and Polyketide Metabolites" O'Hagan; 1993; Natural Product reports, 1995.
"Expression of a Functional Fungal Polyketide Synthase in the Bacterium *Streptomyces coelicolor* A3(2)" Bedford et al.; Mar. 1995; Journal of Bacteriology, Aug. 1995, pp. 4544-4548.
"Multiple Genetic Modifications of the Erythomycin Polyketide Synthase to Produce a Library of Novel "Unnatural" Natural Products" McDaniel et al.; Dec. 1998; Applied Biological Sciences, vol. 96, pp. 1846-1851.
"Lovastatin Biosynthesis in *Aspergillus terreus*: Characterization of Blocked Mutants, Enzyme Activities and a Multifunctional Polyketide Synthase Gene" Hendrickson et al.; Apr. 1999; Elsevier Science Ltd., Chemistry & Biology 6:429-439; www. biomednet. com/elecref/1074552100600429.
"Dissecting and Exploiting Intermodular Communication in Polyketide Synthases" Gokhale et al.; Apr. 1999; vol. 284, www. sciencemag.org.
"Modulation of Polyketide Synthase Activity by Accessory Proteins During Lovastatin Biosynthesis" Kennedy et al.; May 1999; vol. 284 www.sciencemag.org.
"Aspects of the Biosynthesis of Non-Aromatic Fungal Polyketides by Iterative Polyketide Synthases" Hutchinson et al.; May 2000; Antonie van Leeuwenhoek 78: 287-295, 2000.
"Design and Utility of Oligonucleotide Gene Probes for Fungal Polyketide Synthases" Nicholson et al.; Nov. 2000; Chemistry & Biology 8 (2001) 157-178, www.elsevier.com/locate/chembiol.
"Biosynthesis of Complex Polyketides in a Metabolically Engineered Strain of *E. coli*" Pfeifer et al.; Mar. 2001, vol. 291 www. sciencemag.org.
"Molecular Cloning and Characterization of an ML-236B (compactin) Biosynthesis Gene Cluster in *Penicillium citrinum*" Abe et al.; May 2002, Mol Genet Genomics (2002) 267:636-646.
"Phosphopantetheine Transfer in Primary and Secondary Metabolism of *Bacillus subtilis*" Mootz et al.; Apr. 2001.

* cited by examiner

*Primary Examiner*—Nancy Vogel
(74) *Attorney, Agent, or Firm*—Thomas, Kayden, Horstemeyer & Risley

(57) ABSTRACT

Cholesterol inhibitor produced by *Monascus*, monacolin k, is a secondary metabolite of polyketides. The invention provides probes specific to monacolin k biosynthesis gene cluster. BAC clones having putative monacolin k gene cluster were screened from BAC (bacterial artificial chromosome) library, and sequencing and annotation were performed on these clones. The results show that 2 polyketide synthase (PKS) genes and 7 regulatory genes related to monacolin k synthesis were obtained. Full-length cDNAs of these genes were then obtained by RT-PCR and cloned to expression vectors for the expression of these genes.

16 Claims, 10 Drawing Sheets ketoacyl synthase

| Species | Sequence | SEQ ID NO |
|---|---|---|
| A. terreus lovB | NR SY DWHGPS DIAC SS LVA H | SEQ ID NO: 55 |
| M. purpureus mkA | R SY DWHGPS DIAC S LA | SEQ ID NO: 116 |
| P. citrinum mlcA | R V S DWHGPS DIAC SS LAA | SEQ ID NO: 56 |
| Rat FAS | NR S DF GPS A AC SSS LA Q | SEQ ID NO: 57 |
| P. patulum MSAS | R S HLN MGPSTA AC S LA H | SEQ ID NO: 58 |
| A. terreus lovF | R S YD GPS DAC S LTA H | SEQ ID NO: 59 |
| M. purpureus mkB | S R S YD GPS DAC S LTA H | SEQ ID NO: 60 |
| P. citrinum mlcB | NR S YD GPS DAC S LTA H | SEQ ID NO: 61 |
| C. heterostrophus PKS1 | NR S D KGPS L DAC SGGLTA H | SEQ ID NO: 62 |
| G. fujikuroi FUM5 | R SYE D KGPSF KAC SSS LA H | SEQ ID NO: 63 |

FIG. 1A acyl transferase

| Species | Sequence | SEQ ID NO |
|---|---|---|
| A. terreus lovB | R RFT GHS SGE ACA AAGL SA | SEQ ID NO: 64 |
| M. purpureus mkA | QFA GHSSGE ACA TGL SA | SEQ ID NO: 65 |
| P. citrinum mlcA | EFS GHS SGE ACA AAGF SA | SEQ ID NO: 66 |
| A. terreus lovF | N QPV TSHS GEAA A IGA A | SEQ ID NO: 67 |
| M. purpureus mkB | RPAA TSHS GE AA AVGAF SA | SEQ ID NO: 68 |
| P. citrinum mlcB | RPTG TSHS GEAA A AGA SA | SEQ ID NO: 69 |
| C. heterostrophus PKS1 | YAQ TGHS GE A A AGA SL | SEQ ID NO: 70 |
| G. fujikuroi FUM5 | TPAA GHS GE AA A AGA SS | SEQ ID NO: 71 |
| P. patulum MSAS | TPQ M GHSVGE AA VV AGA SP | SEQ ID NO: 72 |
| Rat FAS | K DG GHSLGE AC ADGC SQ | SEQ ID NO: 73 |

FIG. 1B dehydratase

| | | |
|---|---|---|
| *A. terreus lovB* | RDLEWLDGHALQGQTVFPAAGMIVMA | SEQ ID NO: 74 |
| *M. purpureus mkA* | RDLEWLDGHALQGQVVFPAAGMIVMA | SEQ ID NO: 75 |
| *P. citrinum mlcA* | RDLEWLDGHALQGQTVFPAAGKIIMA | SEQ ID NO: 76 |
| *P. patulum MSAS* | DTKPLPGSHPLHGTELVPAAGLLNTF | SEQ ID NO: 77 |
| *A. terreus lovF* | SDLPWLRDHVVGSHLVPHAGIVCMA | SEQ ID NO: 78 |
| *M. purpureus mkB* | SDVPWLRDHVVGSRLLEPGAGELSMV | SEQ ID NO: 79 |
| *P. citrinum mlcB* | SDLPWLRDHVVGSSLIEPGAGELSMA | SEQ ID NO: 80 |
| *C. heterostrophus PKS1* | SELPWLQDHKIQSSILYPVAGMIAMA | SEQ ID NO: 81 |
| *G. fujikuroi FUM5* | DGLEWLRDHQVLNDVVEPCAGMLAMA | SEQ ID NO: 82 |
| Rat FAS | SSDHYLVDHCIDGRVLFPGTGYLYLV | SEQ ID NO: 83 |

FIG. 1C methyl transferase

| | | |
|---|---|---|
| *A. terreus lovB* | DILEIGAGTGGATK | SEQ ID NO: 84 |
| *A. terreus lovF* | RILEIGGGTGGCTQ | SEQ ID NO: 85 |
| *M. purpureus mkB* | RILEIGGGTGGCTQ | SEQ ID NO: 112 |
| *P. citrinum mlcB* | RILEIGGGTGGCTK | SEQ ID NO: 86 |
| *P. citrinum mlcA* | DILEIGLGTGIATK | SEQ ID NO: 87 |
| *M. purpureus mkA* | DILEIGAGTGGATK | SEQ ID NO: 113 |

FIG. 1D enoyl reductase

| Species | Sequence | SEQ ID NO |
|---|---|---|
| A. terreus lovF | LPGETVLIHAGAGGVGQAA | SEQ ID NO: 88 |
| M. purpureus mkB | QRGEKVLIHGGAGGVGQAA | SEQ ID NO: 89 |
| P. citrinum mlcB | RGHRVLIHSAAGGVGQAA | SEQ ID NO: 90 |
| C. heterostrophus PKS1 | RHGETVLIHAAGGLGQAL | SEQ ID NO: 91 |
| G. fujikuroi FUM5 | PGQSILIHSACGGIGIAA | SEQ ID NO: 92 |
| Rat FAS | QHGETMLIHSGSGGVGQAA | SEQ ID NO: 93 |

FIG. 1E ketoacyl reductase

| Species | Sequence | SEQ ID NO |
|---|---|---|
| A. terreus lovB | YLVGLTGDLGRSLARTMVQHGACHLVLTSR | SEQ ID NO: 94 |
| M. purpureus mkA | YLVGLTGDLGRSLARMVLHGARRLVLTSR | SEQ ID NO: 95 |
| P. citrinum mlcA | YLVGLTGDLGRSICRMILHGARHWLTSR | SEQ ID NO: 96 |
| P. patulum MSAS | YLITGGLGVLGLEYDLVEKGARRLLLSR | SEQ ID NO: 97 |
| Rat FAS | SYLITGGLGGFGLELARWLVLRGAQRLVLTSR | SEQ ID NO: 98 |
| A. terreus lovF | SYLVAGGLGGLGRRICEALVDRGARYLILSR | SEQ ID NO: 99 |
| M. purpureus mkB | SYLVGGLGGLGRRICEMVDHGARHLLLSR | SEQ ID NO: 100 |
| P. citrinum mlcB | SYLNAGGLGGLGKQECQLVDHGAKHLLLSR | SEQ ID NO: 101 |
| C. heterostrophus PKS1 | SYLIVGGVGGLGSTALMSTRGARLLLNR | SEQ ID NO: 102 |
| G. fujikuroi FUM5 | SYLIVGGIGGLGRAATMVESGARLLFFSR | SEQ ID NO: 103 |

FIG. 1F acyl carry protein

| | | |
|---|---|---|
| *A. terreus* lovB | IPLIDQGMDSLGAMTVGTWF | SEQ ID NO: 104 |
| *M. purpureus* mkA | IPLIDQGMDSLGAVTVGTWF | SEQ ID NO: 114 |
| *P. citrinum* mlcA | IPLIDQGMDSLGAVTVGSWF | SEQ ID NO: 115 |
| *P. patulum* MSAS | KAALADLGMDSVMTVTLRRQL | SEQ ID NO: 105 |
| Rat FAS | DSLADLGLDSLMGVEVRQIL | SEQ ID NO: 106 |
| *A. terreus* lovF | QTLAGLGMDSLVAIELRNWI | SEQ ID NO: 107 |
| *M. purpureus* mkB | QTLSSVGMDSLMAIELRNWI | SEQ ID NO: 108 |
| *P. citrinum* mlcB | SKNLAGVGMDSLVAIELRNWI | SEQ ID NO: 109 |
| *C. heterostrophus* PKS1 | KSLQDYGMDSLVAVELRNWI | SEQ ID NO: 110 |
| *G. fujikuroi* FUM5 | ASLTSLGMDSLMTIELRNWI | SEQ ID NO: 111 |

FIG. 1G

SEQUENCE LISTING

```
<160> NUMBER OF SEQ ID NOS: 117

<210> SEQ ID NO 1
<211> LENGTH: 226
<212> TYPE: DNA
<213> ORGANISM: Monascus BCRC 38072

<400> SEQUENCE: 1
tccactgccg tttatgttgg catgatgaca cacgactacg agacggtgtc gacgcgcgac      60
ttggagagca ttcccactta ctcggccacg ggagtcgctg ttagtgtcgc gtcgaaccgc     120
atctcatact tctttgactg gcatggcccg agtgtaagtt gctctcatgc cccatattgg     180
taatcttgaa gagttcctaa cggacttgat ggggtgaaga tgacga                   226
```

<210> SEQ ID NO 2
<211> LENGTH: 9818
<212> TYPE: DNA
<213> ORGANISM: Monascus BCRC 38072

<400> SEQUENCE: 2

| | | | | | |
|---|---|---|---|---|---|
| atgtacgtag | gacgcattgg | tgcgaccaca | tacatctctc | gtcccgcaga | ctctcgagct | 60 |
| acgccaaaag | tgatcaaaac | tcaagggtcg | atcaccacgt | ctaatctaac | atcactaaca | 120 |
| accatggctc | agtcaacata | ccccaatgag | cctattgtcg | tggtaggaag | cggctgccgc | 180 |
| tttcccgggg | gcgccaacac | gccctccaag | ctgtgggagc | tccttcggga | gcctcgcgac | 240 |
| gtccgtagca | aaatcccgaa | agagagattt | gacgtcgacg | cattctatca | tccagacgga | 300 |
| aaacaccatg | gacgaacaaa | cgcaccctat | gcctatatgc | tacaagaaga | cctgcgcgcc | 360 |
| ttcgacggcc | ctttcttcaa | tatccaggcc | ggagaggccg | agagtatgga | tccacaacag | 420 |
| cggctcttgc | tggagaccgt | gtacgaggca | gtctcagatg | ccggtatgcg | gatccaagac | 480 |
| ctgcagggggt | cttccactgc | cgtttatgtt | ggcatgatga | cacacgacta | cgagacggtg | 540 |
| tcgacgcgcg | acttggagag | cattcccact | tactcggcca | cgggagtcgc | tgttagtgtc | 600 |
| gcgtcgaacc | gcatctcata | cttctttgac | tggcatggcc | cgagtgtaag | ttgctctcat | 660 |
| gccccatatt | ggtaatcttg | aagagttcct | aacggacttg | atgggtgaa | gatgacgatc | 720 |
| gataccgcat | gcagctcgtc | tttggttgcc | gttcacctgg | ctgtacaaca | gctacgcagt | 780 |
| gggcaaagct | ccatggctat | cgccgcgggc | gccaacatga | tcctcgggcc | catgaccttc | 840 |
| gttctagaaa | gcaagttgaa | catgttatcc | ccctcgggcc | ggtcccgcat | gtgggacgct | 900 |
| ggggccgatg | gctatgctag | aggcgtgagt | gcctcctagt | ttgcagacaa | cgcgcaagtt | 960 |
| cgctaacggt | atgccttgtg | catcgatatc | tctttaggaa | gctgtttgtt | cggtagtgct | 1020 |
| taaaacattg | agccaagcct | tgcgcgatgg | cgacagcatt | gaatgcgtta | tccgagaaac | 1080 |
| cggtgtgaac | caagatggtc | gaacgacagg | catcacgatg | cccaaccaca | gcgctcagga | 1140 |
| ggcacttatc | agggctacct | actccaaagc | cggcctcgac | atcacgaacc | ccgaggatcg | 1200 |
| atgccagttc | ttcgaggctc | atggtcagta | agcttcctag | tatgttctgt | ctgctcgtgc | 1260 |
| actgattact | ttggactcat | ccgcatcata | ggaactggta | caccagcagg | agatccacag | 1320 |
| gaggccgagg | ccatcgcaac | cgccttttc | ggacacaaaa | aggaggcctc | cgatgctgag | 1380 |
| aacgcagaga | ctccccctctt | cgtgggcagt | gtgaagaccg | ttgtcggtca | tactgagggc | 1440 |
| actgccggcc | tggctggtct | catgaaggcg | tccttcgccg | tccagcacgg | agtgatcccg | 1500 |
| cccaacctgc | tgtttgagaa | tatcagcccc | cgcgtggccc | cattctactc | caatttgaag | 1560 |
| attgcaacag | agacaacacc | atggcccacc | atcaaacctg | gacagcctcg | ccgtgtcagt | 1620 |
| gtcaactctt | ttggtaagca | ggccttaacc | cggatgggaa | tgactgtaag | gagtccactg | 1680 |
| ctaatctcta | tggcccatga | aaaggttttcg | gtggcacgaa | tgcacatgca | attattgagg | 1740 |
| aatacataaa | gtctgaccaa | aaggtgccag | cgagccgaca | gccggtggag | tactcagaca | 1800 |
| gtcccagtac | attgaatctg | cccttggttc | tctcggccaa | gtctcagcgc | tccatgaaga | 1860 |
| caacgttgga | gagcatggta | cagttccttc | agtccaaccc | tgaagttaac | ttgcgggatc | 1920 |
| tttcatggac | tctactgcgg | aagcggtcga | ttctaccctt | ccgtcgggct | attgtcggcc | 1980 |
| atagccacga | agcaatccgt | gccgctctcg | aggcagccat | tgaagacggc | atcgttgtga | 2040 |
| gcgacttcag | cgcggatgtc | aaaggcaagc | cgtctgtgct | gggagtcttc | accggacagg | 2100 |
| gtgcccaatg | gcctgggatg | ttgaaggaac | tgattgtggg | atcatcctat | gtgcggtcga | 2160 |

```
tagcggagga gctggatcac tcactgcaga cttttgccgga gaagtaccgc ccctcctgga   2220
ccattctcga gcagctaatg ctagaagatg aggcttccaa cgtccgacac gccagcttct   2280
cccagcccct atgctgtgct gttcagattg ttctggtgcg tctcctgaaa gcagcaggaa   2340
tccagtttgc tgctgtggtc ggacacagtt ccggagagat cgcctgtgca tttgccaccg   2400
gtcttatcag tgcatccttg gcaattcgta ttgcccacct gcgtggagtc gtttcggcgg   2460
agcacgctgc ctccgcgagc ggaggacgcg gatctatgtt ggcagcaggt atgtcctatg   2520
aggaagcgaa agagctctgt gagttggatg cctttgaaag ccgcatctgt gttgctgcta   2580
gcaattcccc agacagcgtt accttctcgg agatgcggca tgcaattgag cacttgcagg   2640
gcgttctgga ggacgaggct acgttcgcca gactgctcag ggtggataca gcataccact   2700
ctcaccatat gcttccttgt gcagcgccgt atatgcaagc tttggaggaa tgcggctgtg   2760
ctgttgctga tggagacggt caggtggaag agggatcatg gtattcctct gtcaaggaca   2820
gcaacgaacc aatgggcctt gccgacgtga ctgctgagta ctggaaagat aacctggtat   2880
ccccggtgct tttctctcag gccgtccagc gggcagccat catgcaccgg ccctggatg    2940 tcgggattga agtcggttgc caccctgctc tcaagggccc gtgtctggct accatcaagg   3000
atgctctgtc ggacgttgac ctggcataca caggatgttt ggagcgcgga aagaatgata   3060
tgaatgcatt ttcccaggcc ctggcctatc tttgggagca gttcggaatt ccaagcctgg   3120
atgctgaccg ctttataagt accattgctc ccgagcgctc ctgcgtgagc ctttcgaagc   3180
agctgccgac gtactcatgg gaccattctc ggagctattg gacggaatct cgtgccactc   3240
gtcagcacct gcgaggaccg aagccgcatc ttctgctggg taagctctct gaatatagca   3300
ctccgttgac cttccagtgg ctgaactttg tccgtcctcg cgacattgaa tggctggatg   3360
ggcatgcatt gcagggccaa gtggtcttcc ctgccgcggg ttatattgtc atggcgatgg   3420
aggcggccat ggaaattgcc aactctcatc aggtgcaagt ccagctactt gagatcctgg   3480
atatgagcat tgacaaagcg gtggttttcg atgatgaaga cagtctggta gaacttaact   3540
tgaccgcgga gtaaccagc ggcatcggta aaggtgaccg gatgatcctc agcttcataa    3600
ttgattcctg tctatccagg gaaggtgacc tctccacctc agccaagggt cagctagtcg   3660
tcacattgga tgaaggccat ctccaggtga ccccagataa cgagaagcag ctcctacccc   3720
cgccagaaga agagcatcct cacatgaacc gagtgaatat caattcattc taccacgagc   3780
tggatctgat gggctacgac tacagcaaag acttccggcg cctgcatagc atgcgacgag   3840
ccgatgcacg agccagtgga atttggaat ttattcctct gaacgacgag gtccacggcc    3900
gtcctctcct gctgcatccc gctcccttgg acattgcctt ccagacagtc atcggcgcat   3960
actcctcccc cggagatcga cgtctacgct gcctgtatgt gccgacgcac attgatcgca   4020
ttgctcttgt gccctctctc tgtcttgcga cagctgcgtc cggttgtgac aagattgcct   4080
tcaatactat caacacctat gacaagggtg atttcctcag cggtgacatc gtggcgtttg   4140
acgcggagca gaccagtctg ttccatgtcg agaatattgt ttttaagccc ttctcgcccc   4200
cgactgcgtc tactgatcat ccgatcttcg ccaaatggag ctggggtcca ctgacccgg    4260 aaaccctgct ggacaacccc aaccattggg ccacggcgca ggataaggaa gcgatcccca   4320
tcattgaacg cattgtctac ttttacatca aattgttcct gcagcagctg acccgagaag   4380
atcgcgaaca agcggcattc cacctgcaga ggcagattgt gtggtgtgaa caagtcgtgg   4440
ccgacgctca cgaaggtcgt caccaatggt acgatgcagc ttgggagaat gataccgaag   4500
cccagataga gcagttatgt gccagaagct cctaccaccc tcacgttcgc ttggtacagc   4560
```

```
gagttggtca aaacctgctc gcaaccatcc gttcgaatgg caacccgttc gatctcatgg   4620
accatgatgg cctgttgacc gagttctata ccaacacgct cagttttggc ccagcgttgc   4680
actatgccca agaccttgtg ggtcaaattg cccatcgcta tcaatctatg gatatcctgg   4740
agatcggagc tggaaccggt ggcgccacca aatacgtgct ggcaacgcct caactcgggt   4800
tcaacagcta cacgtacacc gacatctcga ccggcttctt cgaaaaggca cgcgaacagt   4860
ttgctgcctt cgaggaccgc atggagtttg agcccctcga tatccgccgc agcccagcag   4920
agcaaggttt cacggagcac gtgtacgacc taatcatcgc gtccaacgtg ctacacgcaa   4980
cgcccgactt ggagaagacc atggcccatg cacgctccct gctgaagccc ggggccaga   5040 tggtgattct ggagatcacc caccggaacc acaccagact agggtttatc ttcggcctgt   5100
tcgccgattg gtgggcaggt atcgacgatg ggcggaccat ggagccattt gtgtcgtttg   5160
accgctggga tgagatcttg aagcacgtcg ggttttccgg catcgacagt cgcaccaagg   5220
accgcgatgc ggatctgttc cccacatcgg tcttcagcac gcatgccgtt aactcgacaa   5280
tcgactacct gcacaagcct cttgacgctc cagtgaagga ctcgtacccc ccgttggtgg   5340
tggtcggtgg ccagacgcca aagacccagc gcatcttgga tgagatcaaa gccgttatgc   5400
ctaatcgcca gatccagtta caccagcgtc tcgttgattt gttggatgca gaggacatgc   5460
aggccaagtt caccttttgtt gtcctcacgg agctggacga ggagctattc gctggtctca   5520
ccgaagacag ctttgaagca gtcaagctac tgctcatgta cgccgggaac atgctgtggc   5580
tgaccgagaa tgcctgggtc aagcgccctc atcaggcgag taccatcgga atgctgcgct   5640
ccatcagacg cgagcacccc gacattggtg tccatattat ggatgtcgac tctgccgaga   5700
acctggacgc acacttcctg gtcgaacagg tccttcggct ggaggaggat atcgacgaat   5760
tggcagccac gacaacgtgg actcaggagc cagaagtctt ctggtgcaat ggccgcgcct   5820
ggattcctcg tctgaagcat gataaatcga ggaataaccg tatgaactcc tcacgtcgtc   5880
agatctttga gaccctcaat ccatccaaga tccccgttgc attgaagaag gcggcagcct   5940
cctcttctta ctacctggag tcagctgaga cctggcccgt gccaggtgcc gttactgcag   6000
gggataggaa aacggtccat gttcggctca gccatcccca cgcccttcgg gttggacatc   6060
ttgggttttt ctacctcgtt cagggccacg tcctgaaggg tgatcaagca cttcctgtgg   6120
tggctttggc tgagcgcaac gcatcgattg tccacgttcg ttcagactat gtccatgttc   6180
tagaagatac cgcggtgtct gcgaacaatg gaagtttcat cttggccgct gcagcggccg   6240
tgttggccga cggtgatt cacagtgcca agagcctggg agctgatgcc tcggtcctgg   6300
tcttgaatgc cccgggcttc tgtgcccaga cattgctccg cgctgcaaga gattctggac   6360
ttcgggtcca tctggccacc acatcgtcca gtaccgaccc gtctcctggg gccgaccgtt   6420
gcgtccgact gcatccccgc gacacggata ggcgcctcaa acagcttctg ccccgtggca   6480
ctcaggcatt cttcgatctg tccaccgatc cgagcagtga aggtctcaca cagcgattgc   6540
caaacgtcct tatacccagc tgtgttcggc acagtactga atacttgctc agagataccg   6600
cttccgctgg tgggaaagct acgctgcccg cggcatactg ggagcgtgta gcctccttgg   6660
ctaatcacag cctcagtact cactttaagg agaatgataa tgccagcaat ggatgccagg   6720
tcttgtcttg cacagacatt gtcgcgcgta ataacaagag ccgtctgaac gcatcgactg   6780
tcatctcctg gccagatgac gcggccctcc cggccagaat ccgtcccatc gataccgaga   6840
ccctgtttgc agcggaaaag acgtacctct tagtcggact cactgagat ctcggccggt   6900
```

-continued

```
ccttgggccg ctggatggtc ttacacggtg cccgccgcat cgtcctcacc agccgcaacc    6960
cgcaagtgag cccgaattgg gtggcgcatg ttgaagagtt gggcggccag gttaccgttc    7020
tgtccatgta agattatctc caatctcctt ccttcgcttt gtgactcact aacacacaat    7080
gcagggatgt gacgagcgaa gactcggtgg attctggctt ggccaaactc caggatttga    7140
agttgccccc tatcggcggc attgcctttg gcccttggt gctgcaggat gtaatgctga     7200
agaacatgga cctgcaaatg atggagatgg tgctgaaacc caaggtcgag ggagcccgca    7260
tcctgcacga gaagttctcc gaccctgcca gcagcaaccc actcgacttc ttcgtcatgt    7320
tctcctcgat tgtagcggta atgggtaacc cgggccaggc caactacagc gcggcaaact    7380
gctacctgca ggcttttggcg cagcggcgat gcgcctctgg attggcggta agcttttttt    7440
ccccccaacc atcccttccc ttctgcatgt gtctgtgcta agataaacg caacgcaggc     7500
ttcgactatc gacatcggtg cagtctatgg tgtcgggttc gtgacccggg cggaactgga    7560
ggaggatttc aatgctattc ggttcatgtt tgactcggtc gaagaacatg agctgcactc    7620
tctgtttgcc gaggcggtgg tgtccggtcg acgggccatg caccagcagc agcagttcaa    7680
gacggtgctc gacatggccg atatcgaatt gacgaccggt ataccccgc tggatccgac     7740
tctcaaggat cgcattacgt tcttcgacga cgctcgggtc ggtaacttca agattcccga    7800
acggcgcggc aaggcgggcg ataacgcagc aggatccaag ggctctgtca aggaacagct    7860
cttgcaagct acaagcttgg accaggtccg tcaaatagtc attggtaagt cttggcaaca    7920
tatccttttct ttcacgcgct agtcagcaat gcgattaaca tttttctgggg cagatggtct   7980
atccgaaaag cttcgggtga cccttcagat tcccgatggg gagagcgtgc accccactat    8040
cccgctcatc gaccagggag tagactccct gggcgcggtt accgtgggta cctggttctc    8100
gaagcagctg tacctagacc tgccgcttct cagagtgctt ggaggcgcct ccgtggccga    8160
tctggcggac gacgctgctg cccggctgcc gcccagctcc attccactcg tggcagcaag    8220
cgaaggggc gcggagacct cggacaatga cacttcaggg cctgagggga ctgatctcag     8280
cgcctcgacc acaatcaccg agccctcatc tgcagacgaa gaggacgaaa agcaggagga    8340
cgacaacgac aactccgtcc tcgcccttca tccactctcc ctcggccagg agtacgcttg    8400
gagactgcaa aaggccgccg atgattcgac catcttcaac aacacgatcg gcatgttcat    8460
gacgggctcc atcgacgcca aacggctgtc caaggctctc cgagcggtct tgcgccggca    8520
cgaaatcttc cgcaccggct tgcggctgt cggtaacaat gcagatgcca cgagtctagc     8580
gcaaattgtc tttggtcgaa ccaagaacaa ggtccaagtc atccaggtgg ctgaccgggc    8640
cggcgcggaa gaaggctacc ggcagctggt gcagacacag tacgacatca ccgctggaga    8700
cactctgaga ctggtcgact tcttctgggg caaggacgag catctgttcg ttgtggccta    8760
ccatcgattt gtcggcgatg gttccaccac ggagaatatc tttgtcgaag cgagccagtt    8820
atacggcggc gtgaccctcg acaagcacgt ccctcaattt gcagacctcg cgacgcggca    8880
gcgagaagcg ctcgagtccg gccagatgga tgcggacctc gcgtactggg aatcgatgca    8940
ccaccagccc acgggcgtgg tgtccccggt cctcccgcgg atgcttctgg gcgaagatgg    9000
ccttaatagc ccgaaccacg cccgccagcc caactcgtgg aagcaacacg aagcgatcgc    9060
gcgtctcgac cccatggtcg ctttccgcat ccgcgagcgc agtcgcaagc acaaagccac    9120
gcccatgcaa ttctacctgg ctgcgtacca cgtgctcctg gcacgattga cgggcagcag    9180
cgacttcagc ataggcctgg ccgacaccaa tcgcacgaac gtggatgaac tggcgggcat    9240
gggcttttc gccaaccctgc tcccgctgcg cttccgcaac ttcgtcccgc acatcacctt    9300
```

| | |
|---|---|
| tggcgagcac ctggtcgcca ccaaggacaa ggtgcgcgag gccatgcagc acgcccgcgt | 9360 |
| gccctacggg gtgctgctcg agcgcctcgg attcgaggtc ccgggggcca ccgccgaaac | 9420 |
| agcggaaccg gccccttgt tccaagcggt cttcgattac aagcagggcc aggcggagag | 9480 |
| tggttcgatt ggcagcgcca agatgaccga ggtcatcgcg actcgcgaac gcaccccta | 9540 |
| cgatgtcgtg ctggagatgt cggatgatcc caccaaggat ccgctgctca ccgtcaagtt | 9600 |
| gcagagctcg gtgtacgagg tgcatcatcc cagggcgttc ttggagagtt atatctccat | 9660 |
| attgtcgatg ttttcgatga atcccgcgtt gaagttggct tgatatattg cggtagaggt | 9720 |
| ggtctagatt gttaaactta catgtactac gataattata cggaatagaa caagagtgat | 9780 |
| tatctgtgat gcctagaact acgaacggat gaaggtga | 9818 |

```
<210> SEQ ID NO 3
<211> LENGTH: 8081
<212> TYPE: DNA
<213> ORGANISM: Monascus BCRC 38072

<400> SEQUENCE: 3
```

| | |
|---|---|
| atgaaagcga cggcagcctc gggcacacct actcccatag ctgtagtggg catgggatgc | 60 |
| agatttgccg ggggagcaac agatccacag gcactgtgga aattgctgga gcaaggaggg | 120 |
| agcacttggt ccaagactcc atcctcgaga ttcaacgtca gcggagtcta ccaccctaac | 180 |
| ggccaacgag taggatcggt aagtcagggg atgattctga ggctcggttc tatgtgctca | 240 |
| agtataggca ttgactgctg gcagatgcac gttcggggtg gtcattttct agaccaagac | 300 |
| ccggctcttt tcgatgcctc attttcaat atgaccagtg aagttgccag tgtatgtgca | 360 |
| atgctcgttc ccggttttct cgaccgatga gtgaatgatg ttgagatcgc agcacagtgt | 420 |
| atggaccccc aacagagact catactcgaa gtcgtctatg aagcgctaga ggccggtatg | 480 |
| tgtttcagaa gaggaagcct tcactagtcc ttctttagcc tacaaaatcg tttctgacac | 540 |
| ttgaaatcgc agcggaatt ccccttgaaa gtgtggccgg ctcgaatacc gcggtcttta | 600 |
| gcggagcaat gtatcacgac taccaggatt cgctccatcg caacccggaa actctgccgc | 660 |
| gatacttcat cacgggtaat gctggcacga tgatgtcgag tcgcgtctcc cacttctatg | 720 |
| acctccgcgg tccagcgtc acagttgaca ctgcatgttc caccaccttg actgccttgc | 780 |
| acctcgcaat ccaaagcata cgagcgggag aggctgacat ggccattgtg gccgggtcga | 840 |
| atctgctctt gaactcggat gttttttgtca ccatgtccaa tttagggtga gtgtgctttc | 900 |
| ccgactctat gcattgcatg actagcatgc cagtgtcaaa aaaaaaagtt tccgatgttg | 960 |
| attgttccgt gcccgaggcc agctttctct ccccggatgg gatttcctac tcatttgatc | 1020 |
| cgagagctaa tgggtatgga cgtggagaag gggtagccgc catcatcttg aaggctctcc | 1080 |
| cccgcgcgct gcgagacggg gacccaattc gccttgttgt ccgcgagacg gcgctcaacc | 1140 |
| aagacggtcg gaccccgcc atcaccgggc cgagccccga agcgcaggcg tgcctgatcc | 1200 |
| gggaatgcta tcagaaggcc ggtctggacc cgaggcagac atcgtacgtg aagcacatg | 1260 |
| gaacaggaac tccgacaggt gatccgctgg agctggcggc catctcagct gcattccaag | 1320 |
| gccagcctct gcagatcggc tccgtaaaag ccaacctcgg gcacaccgaa gctgccagcg | 1380 |
| ggctggcaag cgtaatgaag gtggctctgg cactggaaaa agggattgtg ccacctagtg | 1440 |
| caagattcct gcagccgagc aagaagttgc tggaagagag aaaattccag gtgacgttgc | 1500 |
| ctctctctat ctcccgtctg gatttggaca cccaactaac ccatcaccac acatgtagat | 1560 |

```
tcccctatct agccaattgt ggcttccgat tgacggaatt tgtcgcgcat cgatcaacaa    1620
cttcggcttc ggaggcgcga atgctcatgc aatcgtggag cggtatgacc ccgctgcgag    1680
aatatcgacg agcaagccaa acggtcatat ccggcctcac gacagccatg tggaagcaga    1740
tcgagggaaa atctatgttt tgagtgccaa ggacgagcac agttgccagg aaatgatttc    1800
aaggttgcgc gactacctca accgcgctaa tccgactgat gaacggcaat tcctcgctaa    1860
catggcgtac actttagctt ctcgtcgctc gaatctccga tggaaggcag cctgcagggc    1920
acatagcctg gcgagccttc tctctgttct cgtaagcgat gggacgcgac ctcggagatc    1980
ggccgagaaa gcgaggctgg gatgggtctt cactggccaa ggagcacaat ggtttgcaat    2040
gggccgcgag ttaatcgagg cgtatcccgt tttcaaggag gcactcatcg agtgcgatgg    2100
ctatatcaag ggcatgggag cgaactggtc cattataggt aaatcccgaa agaacaccga    2160
tcagagctac gatagcgtga cactgactac tcatcgttcc agatgaactt cgtcgcggtg    2220
aagcagaaag tcgcgtgaac gaggcagaat ttagcctacc gttgtcaacg gctatccagg    2280
ttgcactcgt tcgtctactc tggtcgtggg ggatccgacc agcggcaatt accagccact    2340
ctagcggaga ggtagctgca gcttacgctg tcggggcatt ttcagcccga tcagccattg    2400
gaatcagcta tatacgtggt gccttgatag caaaaaccca gccggcaccg acaacgaagg    2460
ggggcatgct agctgtggga ttgagtcgca gtgaggttgg tgaatacata acacgagtac    2520
aacaacaagg cgaggaatac ttggttgtag gatgcataaa cagcccctcc aacgtgacgg    2580
tatcaggaga tttgtctgcg gttgtcagat tggaggagtt gttgcatgct gaccaaatat    2640
ttgcgagacg actcaaggtc acccaggcgt ttcactccca ccacatgcaa cctttgtcag    2700
gtgaatttcg ggaggctctg gtagaggtct tcaatgcaga catcactgac accactaatg    2760
cctgccagga tgtggtttac gcatccccca aaaccgggaa acgcctagac gattgtaacc    2820
acctgcgcga tcccatgcac tgggtggaaa gtatgctttt cccggtcgaa ttcgaatctt    2880
cattccgtga aatgtgcttc gacaggaaag atcaagcaca agaggttgat aagatcatcg    2940
agattgggcc acatgggatc ctgagcggcg caatcaagca aatcctacag ctgccggagc    3000
tcgctgcatt tgatatatcc tacctatcct gtctgtctcg agggaaaagc gcggtggaca    3060
ccattcagct tctcgccatg gaccttctcc aaggggggtta tcccgtagac ttaaacgcag    3120
tcaacttccc atacgggtgc gaagcagccg aagtccaggt gctgtccgat ttgccgacct    3180
atccctggaa tcacaagacg agatactgga aggagccacg catcagtcga gctgcacggc    3240
aacgaaagat ccccgtgcat gatctgatcg gagttcaaga gcctttgtgc cctccgcttt    3300
tgcacttgtg gcaaaatgtg cttcggatct cggatgtgcc gtggatacgc gatcacgtcg    3360
tgggctcacg aatcctttc cccggtgctg ggttcatcag catggttatt gatgggctct    3420
ctcagatctg taatcacgat cccgaaactt gcggtttaag ctacatctta cgcgacgtgg    3480
acctggcgca ggcgctgatc ctgcccacgg acggagacga aggggtggat ttgcgcctaa    3540
caattcgcgc cgctgatcag aagagtctcg gaatgcggga ctggcagaga ttctccgtct    3600
attccatcgc cggtgataag gacgactgga cggagcattg tacagggctg attcgcgcgc    3660
aggtcgatca tcctgtctcc agctcgtcga tccaacaaaa gaccaatcca ccgcaatgga    3720
gccggaagat ggcaccacag gacctgtggg cttcgctgca tgcgacggga atctgtcacg    3780
ggcccttatt ccagaatatt gagcgcattg aaagcgatgg ccaggcctcg tggtgcactc    3840
tgaccgttgc cgacacagtg gcgactatgc cgcacgccta cgagagccag cacattgtgc    3900
atccaaccac attagactcg gctatccagg cggcctatac agtgcttcca tttatgggaa    3960
```

```
cactgatgaa  gacagcgatg  gtccccagtc  gaatcggcgg  catgaagata  cccgccagct  4020
tcgcgagctt  ggaaccgggt  gatatgctgt  gcgcacaagc  aaaaataaag  aaccaaggcc  4080
tctctgcctt  tacaaccgat  gtagctgtgt  tcaacgagtc  agatatggat  gaagaggcag  4140
gtatcgagct  cgaagggctt  accttccagt  cgcttggtgc  tgttattagc  gactctaggc  4200
gagatttgac  cgagaacgag  agcacctaca  gttcctggca  tgggctccc   gacatcactc  4260
tgaccaattc  cacatggctt  gagaggatac  taagcactgg  gacccagtct  caggagatcg  4320
gggtgatgtt  ggagcttcga  cggtgtactg  tccactttat  ccaggaagca  atagaaaacc  4380
taacaacgga  agatgttgag  aggctgagtg  gtcatctcgt  caaattttat  tgctggatgc  4440
aggctcaact  ggcctgcgct  accaatggcg  agctggggca  agacagcgcc  gactggttgc  4500
gagacagtga  gcaggagaga  caaagcttgc  ggtccagagt  agtcgctgcc  accaacaatg  4560
gcgagatgat  ctgtcgtctg  gccccaagc   tatccgctat  cttgcgtggc  gagctcgacc  4620
ctcttgagct  gatgatggac  ggccaactgt  tgtctcgata  ctacatcagg  gcaatcaaat  4680
ggagccggtc  caatacgcag  gcaagcgaac  tcgtgcgcct  ctgctgccac  aagaatccac  4740
gtgcccgcat  ccttgagatt  ggcggtggaa  ctgggggtg   cacacagctc  atcgtaaacg  4800
ctttggggcc  cacgaagccg  gtaggccgct  acgacttcac  cgacgtgtct  gctggcttct  4860
tcgaagcggc  tcgaaagcgg  ttttcggggt  ggcaggatgt  gatggacttc  cgcaagttgg  4920
atatcgaggg  cgatcccgaa  gtgcagggt   ttgactgcgg  atcctacgac  gtggtgttgg  4980
cctgtcaagt  tcttcatgct  acaagcaaca  tgcagcggac  attaaacaat  gtgcgcaagc  5040
tgttgaagcc  gggaggtaaa  ctcattcttg  ttgaaaccac  gagggaccag  ctcgatttgt  5100
ttttcacatt  cgggctcctg  cccggctggt  ggctcagtga  agagccggaa  cggcagctta  5160
ccccatcact  gtctcctgag  ttatggcgca  gtgtactgag  cgctactggt  ttcagtggcg  5220
tggacctaga  ggtccgcgac  tgcgacagtg  atgagtttta  catgatcagc  accatgatgt  5280
ccacagctac  acctgggact  cctgcaacta  ccttgaatgg  accagccgag  gtgctcctgg  5340
tccatgccgc  ctcgcctccg  cccatggatt  ggctgcagaa  tctgcaggta  gccctcggcg  5400
ggaaaaacag  ttctataact  tcactcaagg  cgctccaggg  cgtttctgat  ctcaagggga  5460
agatgtgtgt  attcctgggg  gagatggacc  gcaccctact  tgaaagcgtg  gtcagtgatg  5520
acttcacatc  cttaacctct  atgctacagt  atagccaagg  tactctttgg  gttactcgag  5580
gagcggcgat  ggcgtcggat  gacccaagaa  aggccctgca  cctaggattg  ctacgcacgc  5640
tccgcaatga  gaatcacggc  cgtcgatttg  tttcattgga  cctcgacccc  ttgcgtgatc  5700
catgacggc   ccagtcctgt  gacgccattg  tcaatgtact  gaatgcagtc  ggtgcgtctc  5760
atgagaagga  gtttgagtat  gcagaacgcg  atggcactat  tcatgtgcca  cgaacgttca  5820
gcgactcaag  ctccagcgag  aaggaagact  tggttgtctt  ggagccattc  cagaatgaaa  5880
cgcgcttggt  gcgactagac  gtacagactc  cagggcttct  ggattctttg  cactttaagc  5940
tgtgttctgc  ggacgaagct  tggagtagtg  agctgccaga  ggactgggtg  agattgagc   6000
cgagggcgtt  cggtctaaac  tttcgcgata  tcatggttgc  catgggccag  ttggagtcaa  6060
atcgagtcat  gggctttgag  tgcgctggtg  tggtaactag  gttgagcaaa  gcagcaacaa  6120
caggcgcagg  agggcttgca  atcggagacc  gtgtatgtgc  actcatgaaa  gggcattggg  6180
catcgagggt  gcgacagcc   cgcaccaatg  tcatctgcat  cccagggacc  ctgagtttcg  6240
aacaagcggc  ttccatccca  ctggccttca  cgacagctta  cacctccctc  tacactgttg  6300
```

-continued

| | |
|---|---|
| ctcgccttca acggggtgaa aaagtgctaa tccatggcgg cgctggagga gtcggacagg | 6360 |
| cggccatcat ccttgctcaa ctggtcggag cggaggtctt taccactgct ggaactcact | 6420 |
| ctaagcgcaa cttcttgatc gataagttca agctggcccc cgaccatgtc ttctcgagca | 6480 |
| gagactccgg ttttatcgag ggtatcaggg cttgtaccaa tggcaagggg gttgatgtgg | 6540 |
| tgctcaattc tcttgctggg cctttgcttc aatatagctt cgactgtctg gtcaattttg | 6600 |
| gtcgcttcgt ggaaataggc aaaaaggatc tcgagcaaaa tagccgactc aacatggcga | 6660 |
| cttttgcgcg gaacgtctcc ttttcctcga ttgatatcct gtactgggaa gaagccaagt | 6720 |
| ccgccgaaat cttccgagca ttgacggaga ttatgcggct cttggaacaa agacaatcg | 6780 |
| atttgattgg gccgatatca gagtatccca tgtcggctat tgagaaggca ttccgtacga | 6840 |
| tgcagagcgg ccagcacgtc ggtaagcttg tggtggctac ggctgagacg gacatgatcc | 6900 |
| ccgttcgccg gggaaccatg ccagtcgcgt tgaagcttga cgcgtcttac ctgattgtcg | 6960 |
| gtggactggg gggtattggc agacgcattt gcgagtggat ggtggaccat ggggcacgac | 7020 |
| atctgctcat cctgtcccga agcggtcgta cggatccctt tgtgactggc tccagaagc | 7080 |
| ggggctgtgt cgtacgtata cattcatgtg atgtggcaga tgagagtcaa cttcatgcag | 7140 |
| ttcttcaaca gtgccatgag gataacatgc cccgatccg gggtatcatt caagcggcca | 7200 |
| tggtcctcaa ggacgctctt gtctcgcaaa tgacggcgga cgacttccat gttgctcttc | 7260 |
| gtccaaaggt ccagggcagt tggaatcttc acaagatcgc atctgaggtg gacttttca | 7320 |
| tcatgctctc atctctggtg ggtgtcatgg gtggcgcggg tcaagccaac tatgcggctg | 7380 |
| caggcgcgtt ccaggacgcg ctcgcacagc accgggtcgc tcaagggaag cccgctgtca | 7440 |
| ccatcgacct gggcatggtc aagtcaatcg gctatgtggc agagactgac cccgcagttg | 7500 |
| cggagcgatt ggcccggatt ggctatcaac cgatgcacga ggaagaggtc ctcgccgtgc | 7560 |
| tcgagcgagc catgtcgccc tcctcttctt cggcaccacc gtcctctaac cctactatac | 7620 |
| ccgcctcgcc cgctgtcatc gttaccggca tcaacacagg ccctggccct cacttcacaa | 7680 |
| acgccgactg gatgcaggag gcacgtttcg cgggaatcaa gtatcgtgat cccctgaagg | 7740 |
| atgaccgtgg tggggccttg tcctcttcac agcccgctga cgaggatagt gtacgcgctc | 7800 |
| ggctaagtcg ggcatctacc gaggaggagg ccactgccct agtggtgcag gtgatgggtc | 7860 |
| acagactggt gacgatgttt ggtctcactg aaagtgagat gtcggccaca cagacattgt | 7920 |
| cgagcgttgg agtcgactcg ctcgtcgcca tcgagctgcg taactggatt accgcccaac | 7980 |
| ttaatgtgga tatctcggtc tttgagttga tggagggtcg gaccattgct gaggtggcgg | 8040 |
| aggtggtagt gaagaagtat ggcgtgggaa gcaaagtcta g | 8081 |

<210> SEQ ID NO 4
<211> LENGTH: 1717
<212> TYPE: DNA
<213> ORGANISM: Monascus BCRC 38072

<400> SEQUENCE: 4

| | |
|---|---|
| atgacagttc cgacagatac ggtctcgcgt cgcctccagt ctctcgcttg gagcgacata | 60 |
| aagcagcatg ccccatggct gccgtcttct cgcactcttg tctcgggatt tctctgtttg | 120 |
| atccttcttc agattctgta ctctcgtgga cgcaaatccg acctgcgggt gtataacccg | 180 |
| aagaaatggt gggaactcac caccatgagg gccaagcggg agttcgatgc gaatgcgccc | 240 |
| gcatggattg aggcctggtt ctccaagaac gaccaaccgc tccgtttcat tgtcgactct | 300 |
| ggctattgta ccattttgcc ctcatcgatg gccgacgaat tccggaagat gaaggagctt | 360 |

-continued

```
tgcatgtaca agttttggg cacggtcagt ttatctctga gttctttcca tcttcccgct    420
attttcgtgt ctgggttact gatgatcatc ttgactgtca ggacttccac tctcatcttc    480
ccggattcga cggcttcaaa gaagtcacca gagacgcaca tctcatcacc aaggtggtca    540
tgaatcagtt ccaaacccaa gctgcgaaat acaccaagcc tcttgccgat gaggccagcg    600
cgacaattgc agatatcttt ggggacaaca agggcaagtc aagcatccta gtcaacccgt    660
tggtcgttat gttaacgggg tctctctatc ttttccagaa tggcacacgg ctcctgtcta    720
taacgagtgt ttagatttgg tgacacgcac tgtcactttc atcatggtcg gggataaact    780
ggcgcacaac gaggaatggt tggatatcgc caagcaccac gcggtgacta tggcgattca    840
ggctcgccaa ctccgcctct ggcccgtcat tctgcgccct atagtccact ggctcgagcc    900
ccagggagcc aaactgcggg cgcaagtccg acgagcccgg cagcttctcg agcccatcat    960
ccaggagcga cgcgccgaga aggccaaatg cctcgcccaa gggatcgagc cgccgcgcta   1020
cgtcgattcc attcagtggt tgaagacacc cgccaagggc caatggtacg atgcggcggg   1080
ggcgcagttg gccatggact tgccggcat ctacggcacc tctgacctga tgatcggcgg   1140
gctggtcgac atcgtccgcc acccgcatct catcgagccc cttcgcaacg agatccggac   1200
cgtcatcggc gaggaaggct ggacgccggc tcgttgtac aaactcaagc ttctggacag   1260
ctgtctcaag gaatcgcagc gcgtcaagcc cgtagaatgc ccacgatgc gcagctacgc   1320
gctccagaac gtgaccttct ccaatggaac ctttgtcccg aaaggcgagc tggtagctgt   1380
ggcggccgac cgcatgagca accctgaagt ctggcctgag ccgaagaagt acgacccgta   1440
ccgatacatg cgcctgcgag aggatcccga caaggcgttc agtgcccagc tggagaacac   1500
caacggtaac catatcggct ttgggtggca tcctcgggcg tgtcccggac ggttcttcgc   1560
ctccaaggag atcaagatca tgttggcgtt tctgctgatt cggtacgact ggaagctggt   1620
gccaaacgag ccgttgcagt attaccgtca ttccttcagc gtgcgcatcc atcctgccac   1680
caagcttatg atgcgccgtc gggacgaaga tctctga                            1717
```

<210> SEQ ID NO 5
<211> LENGTH: 792
<212> TYPE: DNA
<213> ORGANISM: Monascus BCRC 38072

<400> SEQUENCE: 5

```
atgcgtatcc aacgcaccc cgcgccccc aaagcgcccc gggccctcct ctgcgtgcac     60
ggcgccggct gctcccccgc catcttccgc gtgcagctct ccaaactccg cgccgcttta    120
cgggaagact ttgaattcgt ctacgcaacg gcacccttcc cttccgcccc tggacccggg    180
atcctgccca cgttcgaagg cctcgggccc tattacacct ggttcgaggg ttctccgtct    240
ggtgctgctg ccaaagggga taacagcaac agcaacgaca gcaactcttc tcccaccgta    300
cacgaccgcc tcgccgccgt ccacgaaccc gtccgccgcg ccatcgccga tggcagacc     360
cagaacccca gcatccccat cgtgggaacc gtcagtttct ccgagggcgc tcttgtgacc    420
gccctgctgc tctggcagca gcagatgggt aggatacccct ggctcccggt catgcaggtt    480
gcgatgttca tctgctgctg gtatcagcat gaggcgactc agtatatgcg ggaggaggta    540
ggctgcggcg gtgatggtgg cattgacggt gagaagttgg tgatccgggg ggtgctgtcg    600
ctgcacctgc agggtcgtga tgactttgcc ctggcgggtt cgaagatggt ggtgcgcag     660
cattttgtgc ccggggaggc gcaggtgttg gagtttgcgg gccggcatca tttcccgaat    720
```

```
cggccgcgcg atgtgttgga cacggttaag cggtttaggc agctgtgtgt gagggctaga    780
gtcattgggt ga                                                        792
```

<210> SEQ ID NO 6
<211> LENGTH: 1228
<212> TYPE: DNA
<213> ORGANISM: Monascus BCRC 38072

<400> SEQUENCE: 6

```
atgaccatca ccttcaccct accacctcac cagactgcgc tgacagtgga cgagcatgac     60
aaagtcacca tctgggacgt cgcccccctgt ccaagcctcc ccccgatca ggtctgcgtg    120 cgcgtcgagg ccgtagccct caaccccagc gacacgaaga tgcgcggcca attcgccacc    180
ccctacgcct tcctgggcac cgactacgcc ggcaccgtcg tcgccgtggg atcgcaggtc    240
acgcacatcc aagtcgggga ccgggtctac ggcgcccaga cgagatgtg tccgcgcacc    300 ccccgaccag ggcccttctc gcagtacacg gtcaccgcg ccgcatctg gccacggtc     360 cctgagggct ggtccttcga gcaggccgcg tcgttgcccg cgggcatcag cacggccggc    420
ctggcgatga agctgctcgg gctgcccttta ccggatccca atgctacgac ggcaccggcc    480
cttccgaagc ccgtgtatgt tttggtgtat gggggtagca ccgctactgc gacgattgtg    540
atgcagatgc tacgcttgta ctgttgcctt cctctgcctg ccagcccaag cttgatatat    600
gtcgtgctaa ccggcgggat tggatcaatc tcgtgtaggt ccggatacat ccccatagcc    660
acatgctccc cgcacaattt cgacctcgcc aaaaagcacg cgcagaaga tgtctttgac    720 tatcgtgatg ccggtctcgc gcagacgatt gtgagttcat ccctctcc caccaagtta    780 agccacgcgg ttgacgattg ctaacctgct tcagcgcaca taccaaaa acaacctccg    840 ctacgccctc gattgcatca ccaacgtcga gtccaccacc ctctgcttcg ccgccatcgg    900
ccgccgcggc ggccgctatg tctccctgaa cccgttcccg gaacacgcgg cgacccggaa    960
aatggtcacc gccgactgga ccctggggcc gaccattttc ggggaagggt cgacttggcc   1020
ggcgccgtat gggcggccgg ggagcagaaa ggaccgcgca ttcggcgagg agttgtggcg   1080
cgttgcggca aggctcgtgg aggatgggaa gatcgtgcac catcctctgc gggtgattcc   1140
tggcgggttc gaggccatta agcaggggat ggagttggtt aggactgggc agttgtcggg   1200
agagaaggtt gtggtgaagt tggggtaa                                      1228
```

<210> SEQ ID NO 7
<211> LENGTH: 1425
<212> TYPE: DNA
<213> ORGANISM: Monascus BCRC 38072

<400> SEQUENCE: 7

```
atgcgtcaat ttctctcctc tgatcgcatc aactctgaaa tccccagga gaaaagcgaa     60 atggtaggat tcagtgatat cgacaatagc agccgccaga tcaaagaaat ggaagccgct    120
ttccgatcgg ccgtgaaaac agggcagatc ccggggggcag tcatcatggc tcgagatcat    180
agtggtaagc aaacccgcat tattctgtct tcttctcttt ctatctcgac gtgtaataac    240
cgggggagtg ggccgaaggc cgactgaact atacgcgctg cttcggggcg cggacggtgg    300
tgcgcgatga gtgtaaccga ctccctccga tgcaggtcga caccccctgc cggctggcga    360
gtgccaccaa gctgcttacg acgatcatgg cgctgcaatg cgtggagcgg gggctcgtga    420
ggttggatga acggtggat cgactgctgc cggatttgag tgcgatgaag gtgctggagg    480
ggtttgatgc cgcgggggag ccgaagatga gagagcggaa ggggaagatt actttgaagt    540
```

-continued

```
aagtgaatct agctcgttgc attctatttg atacacttgt gtatgtagag aaaaggagaa      600
aaagagaaaa agagagagag actaattcac gtgctgttca cgcccagaca tctcctaaca      660
cacacctccg gcctgtccta cgtcttcctc cacccctcc tccgagaata catggccaaa       720
ggccacctcc agacggctga gaaattcggg atccagagtc ggctggcgcc cccggccgtc      780
aacgacccgg gcgccgagtg gatctacggc gccaacctcg actgggcggg gaagctggtc     840
gagcgcgcca cgggcctgga cctggagcag tacctccaag agaacatctg cgcgccgctg      900
aacatcaccg acatgacctt caagctgcag cagcgacccg atctgctggc gcggcgcgcc     960
gaccagacgc accgcaacaa ggcggacggc cgcctgcgct acgacgactc ggtgtacttc      1020
cggtccgacg gcgacgagtg ctttgggggc caggggtct tctcgggccc cgaatcctac       1080
atgaaggtcg tgcactccct gctgcagcgc gacgggcgcc tgctgcggcc cgagaccgtg      1140
gacttgatgt ccagcccgc gctcgatgcg caaacggaga agcagatgaa ccagcatatg       1200
gacgcgagcc cgcacatcaa ctacggtggg ccgatgccca tggtgttgcg gcggagtttt     1260
gggcttggtg gatgattgc cttggaggat ctggatgggc agaagtggcg ccgaaagggc      1320
tgtttaacct ttggcggcgg gccgaatatt gtatgggtaa tgttactctc agccctacgc      1380
ttcgttttct tcttcttctt cttcttcttc ttctgctcta gctga                     1425
```

<210> SEQ ID NO 8
<211> LENGTH: 3356
<212> TYPE: DNA
<213> ORGANISM: Monascus BCRC 38072

<400> SEQUENCE: 8

```
atggcatcgg cagccgtgac gccaaagctt ggctgggtgc agcaccaggt aaccaacgga      60
ttacatgccg tggtcggcca agtgtgtcga catcccatcc acacgttgct ggtgactgct      120
ctgatcgccg caacgactta tctccatgtt ttggaaggca cctttcgcgc agccaaccta     180
ggtcccggtt ccaagactga cgcagccccc ttcgacgtcc agtcgttcct ctggggcagc     240
cgaagtcttc gcctgggcga cacaagctcg tggagatggc aggtgggcga cttgtctgag    300
gcgactggcg atggccaagt atgataaacc ctttttttttt tttttttttt tctgttttgc    360
ttctgtcgat cccaaaactt gcgcgctgac tgcgaccgca ttgttattgc tttctctcta    420
atcaggtcaa tcaccactgg gctcttgtca ctctcagctt cccggcgcc tcggtcgatg      480 atcgcagccc tgccttttctg tggaacgcac tgcccgactc tgtgggcgca gagccgatca   540
cgccaacctc caacttcttc acctcgatct ccaatgaatt ctcgctggcc tttcgagtcc    600
catacaccca attgagcgat tttctggagg cggtggagtt tgttgcctcg gataaggagg     660
atcgtagctg ggccatcagg tttcctcacg gagagggcaa gcccatttcg ctgggccgct    720
ggctcgggaa ctcgtggctg tcgttccttc accgggctaa acacgccgag acggtagaca    780
tggctatcat cggtttaggc tacctcgctc tgaatatgac cctggtctct ctcttccgag    840
cgatgcgtca gttgggctcg cgtttctggc tggcagcctc cgtgctgctc tctggggcgt    900 tgcctttgt attcgggctc ggtgtcacga ctgcctgcgg cgtgccagtc gacatgcttc     960
ttctgtcgga agggattccc ttcctggttt tgaccgtggg gtttgagaag ccgatccgat    1020
ttacccgtgc tgttctctac gcatcgaatc agctccggcg cgggttgcag cagcgggacg   1080
ttgccgacaa gcatgacagc cggcagcgcc atatgatccc caacgccatg ctattcgcca    1140
tcaacagaga aggatggtcc attgtccagt cgtaccttct tgagatcggg gctctcgcat    1200
```

-continued

```
tgggtgcggt cttccggcca cgggaacgat tcggccagtt ctgcttcctg gccgcatgga   1260
tggtgctctt cgacgccatc cttcttttca ccttctacgc caccattctc tgcgtcaaac   1320
tggaggtgac ccggatgcaa accccggca ccctggatct ggcagacgac caacatgggc   1380
cgcgcatctt cgggtacaag gtcaatccga ccagcctggc ccggtggaag ctaatcatgg   1440
taggcgggtt cgtgctcttc aacgtcctcc aactgtcatc gttcttttat cgcatcatgg   1500
gaggcttcat gaccaatgcc gctctgaccc cgaccaccgt cagtccgttc aaagtggctg   1560
ccaacgggct gaacgatatt tatttggccg cccgtgccgg cggagttgag acgtgggtca   1620
cggtgctacc gccgattcga tatgtcatgg aagcatctgg gttggaaatg tcggccggca   1680
gacgtcctgt atttgatggc gtgctggccg gactggagag cccctgggt cggctctgtc   1740
tcatgggcgc tttggttttc agtctttacc tcaataacca cctgatcccg gccgcccgct   1800
ggcatttttc ccccggcgca ccgaaagaat ccgctgcgcc tgcaccccct tcatcgcccg   1860
catcggtccc cagcgctgta ccgtccctg cgccctcctc tcgcagcttc gaggaaatcg   1920
aggccctatt caaagcgaac caggcggaat ctctgaccga tgacgagctg gcggagctct   1980
gtctccgtgg taagattgcc ggatacagct tagagaagac cttggaaagc attgcctccg   2040
caggttcttc aagcacagca acaactaggc tggaggcttt cacgcgcgcg gttcgcatcc   2100
gccgggccgc cgtgtcgcgg acgccttcga ctcgggacct cagcggcggc atccaggagt   2160
cgctgctccc ctaccgcaac tacaactacg agctggtgca cggcgcctgc tgcgagaatg   2220
tgatcggata cctgccccctg cccctgggtc tcgcaggacc catggtgatc gacggccagg   2280
cgtatttcat cccgatggcc accaccgagg tgtcctagt cgccagcgcc agccggggct   2340
gcaaggcgat caacaccggg ggcggcgccg taacgatgct caagggcgac ggcatgacgc   2400
ggggcccctg tctgggattc ccttcggcga acgcgccgc cgaagcccaa cgctgggttg   2460
agtcccccgt cggccatcaa gtcctcaccg acgccttcaa cgccaccagc cgctttgccc   2520
gtctgcagac cctgactgtg gcccaggccg gcacctacct ctacatccgg ttccgcacca   2580
cgaccggcga cgcaatgggc atgaacatga tctccaaggg ggtcgagaag gccctacagg   2640
cgatgaccgc ccacgggttc cccgatatga acaccatcac cctgtcgggc aatttctgcg   2700
ccgataagaa atccgccgct atcaactgga tcggtggccg cggcaagtcg gtcatcgcgg   2760
aggccaccat ccccgccgat accgtccgga aggtcctgaa gactgacatc gatgcactgg   2820
tcgagctcaa cacggctaag aacctggtgg gtagcgccat ggctggtagt atggggggt   2880
tcaacgccca tgcgtccaat ctggttcagg cggtgttcct ggccactggg caggatcccg   2940
ctcagaatgt ggagagtagt agctgtatca caacgatgaa gaagtatgtg ttttttttt   3000
tttttccct ttatagtttc cccagattcc ctccccctta atctcaactt gtactaacag   3060
cgaaacaccc caggatcgac ggaaacctgc acattgccgt ctccatgccc tcgatggagg   3120
tcggcaccat cggtggggc accatcctcg aagcccaggg agccatgttg gacttgctcg   3180
gggtccgggg cgcccatccc accgatcctg gtgcgaacgc tcgacgcttg gcccggatcg   3240
tcgccgcggc cgtgctggcg ggtgaactga gtacctgctc tgccctagcg gccggtcatt   3300
tggtaaatgc ccatatgcgg cacaatcgca gtgcggcgtc gtcggaaaag aaataa       3356
```

<210> SEQ ID NO 9
<211> LENGTH: 1464
<212> TYPE: DNA
<213> ORGANISM: Monascus BCRC 38072

<400> SEQUENCE: 9

```
atggccctat cgccagtcca ggatccccct tcacacaccg acaaaactat gccccgccgt      60
gcatttcgcc gatcttgtga ccgatgccat gcacagaaga ttaagtgtat aggcagcgag     120
ggagctgttg cccgtgcttc atgtcaacgt tgccagcaag ctggactgcg gtgcgtttac     180
agcgagcgat gccctaagcg caagctaccc aaacccaacc cagcggaatc ttcccctgca     240
agcagcacgg ccggcctgca cacctcttct tcagattctt cgcccctgt tcctccgat      300 ggcttgccgc tagacctgcc agggccggat tcctcaggcg tctccctcca attcctcgac     360
ccgtctgccg actgcgactg gccttggtcc tcgatcggtg tggacgaaac cgttgtcaac     420
aattgcttgg acttatctca tggccatggc catggagacc tcagttgcca gctcgagctg     480
cctatgccag atcttccctc cccccttcgaa ttctcggccg aaaaatctcc ctcaccgtcg     540
gtgtctggca gcattgccgg agctgtcagt gcacaacgag aactcttcga tggcttgtcg     600
acggtgtccc aggaattgga agccatcctt ctggctgtgg cggtggagtg gccaaaacag     660
gaaatctgga cttgtgcgta actccgtttc ccttaacctc actcccccc cctcctaaa     720 gaagaagaag aacatctgga aaagctaatc tgctttatgc tattgctaga ccccattggg     780
acgttcttca acgcatcacg aagacttctt gtatatctcc aacaacaatc caacacccgc     840
agcgaccaag gcatgctgaa tgaatgtcta cgaaccaaga acctcttcat ggcagtgcat     900
tgttatatgc tgatcgtgaa gattttcacc tctctctcgg aattgctgct atcccagatc     960
cggcattccc aggctggcca gctgacaccc ttggaagggc atcagttcga gccaccaccg    1020
agcagcagca gggaccgtag cagcgtcgat accatgccca tcttcaaccc gaatctccac    1080
atcggcgggt tgttttctta tctcaaccc ttcatgcacg ccctatcctc ggcttgcacc    1140 accttgcgc tcggcgtaca gttgctgcga gagaatgaga gtgctcttgg gatcccccg    1200 gcgcagggg tggcggcctc tgtgagtatg ggcaaggagg agtgggcaga cggcgaggat    1260
gtagccagtg cagtgacgac ggcggacgag gatctccgcc agccggcctc gcggatctta    1320
tccatggtct ggagcgatga ggtgggcgac cagaaggcca agtctgctga tgctgctggt    1380
ccgcgaagcc gaaccctggc ggtgctacgg cggtgtaatc gagagatctt ttccctggcc    1440
cgccaacaca acctggcctc ctaa                                          1464
```

<210> SEQ ID NO 10
<211> LENGTH: 2148
<212> TYPE: DNA
<213> ORGANISM: Monascus BCRC 38072

<400> SEQUENCE: 10

```
atggcttccc accagtctga gaaagagaag ccacagagct gcaccactga agtccaggtc      60
agccatgtca ccggcctaaa gctaggactg gtagtaacct cggtgaccct ggtggtgttt     120
ttgatgttgt tggacatgtc tatcattgtg acagtaagca tggctccagc tcgctaggtc     180
cggacgcagc tgatcgcgat tgcaggctat cccccatatc actgctcagt ttcattccct     240 tgggatgtt ggatggtatg gaagtgcgta tcttttgtcg aggtgataat ccaaaccccc     300
tctcttattt tcgtggcaag tgggcgttcc gtttacgctg tagtgtgctc tagctgtgct     360
ctacagccct tggcagggaa gctctacact ctccttgacat tgaagtatac cttcctagca     420
ttcctcgggg tgtttgaagt cggatcagct ctctgtggcg ccgcgcgttg ttcaactatg     480
ttgatcgtgg ggcgcgcagt ggctggcatg ggaggatcgg ggctcaccaa tggagccatc     540
accatcctcg cctctgcagc tccaaaacaa cagcaaccac gtaagtgctg gtcacgggtc     600
```

-continued

```
gaccgatcgg acttcggtga tggcatactg acaaagctac atagtgttaa tcgggatcat    660
gatgggtcgt aagcttcctt atgcactaac tcccaaaggc caaacacgag gtctgatttg    720
aatctagtga gccaaattgc cattgtctgt ggaccattgc tgggaggtgc ttttacccaa    780
cacgcaagtt ggcggtggtg tatgtcccaa cgttgttttg tatgttgcca gtcgacgttc    840
ttgctgaaat ggaaacccac gatcgttctt ccacccaggc ttctatatca atcttcctgt    900
cggagcgctg gccgccatcc tccttctcgc catccacatt cctaagagtg tgccaacatc    960
ggattgcaca atgcctgctc ccagagctgt tggggtccgg tcatcctga gtcagctcga    1020 tctcctgggg tttgtgctct tcgccgcctt tgccgtgatg atctcacttg cgttagaatg    1080
gggcgggtcc gattatatgt gggatagctc cgtaatcatc ggcttgttct gtggtgccgg    1140
catctcgctg gtggtgtttg ggttctggga acgctacgta ggcaactcga tggcgatgat    1200
tcctttctcg gtggccagtc gtcgacaagt ctggtgctcg tgtcttttct tgggcttttt    1260
ctccggggcc ttgctcacct tctcttacta ccttcctatc tacttccagg ccgtgaagga    1320
cgtctctccc accatgagtg gggtgtatat gcttccaggc atagggggac aaattgtgat    1380
ggcgatcgtc tccggcgcaa tcagtgagtt cagaatatca ctttgataat ttctgttttg    1440
tggggaaacc atgcacgact gaccaatcta tataagtcgg caaaacgggg tattacattc    1500
cctgggcgct tgccagtggg atcatcgtat ctatctccgc aggcctggta tcgaccttcc    1560
agccgcatac ctcaatcgca gcgtgggtga tgtatcaatt catgggggc tttggtcgag    1620 gatgtggaat gcagaccgta cgttacccca accaacatac gaggtgtttt tgtttctgtt    1680
ctgtttctgg tttgttccag gttcttttct atttctgtac tcactctagc tcactcgctc    1740
tctatctcct tctagcccat cattgccatt caacatgccc tgccaccaca atgagtgcg    1800 ctcggtatct cgctggccat gttcggccag accttcggcg gctccctctt cctcaccttg    1860
gccaagctcg tcttcagcgc cggccttgac gccggcttac gcgagtatgc gcccgccgtc    1920
agcgcagagg cggtgacggc cgcgggcgcc acgggcttcc gcgatgtcgt ccccgcaaat    1980
ctcctttctc aggttctcct ggcatactgt aaagggatag accatacatt ctaccttgcg    2040
gtcggggcat cgggagccac ttttttgttt gcgtggggaa tgggtcaggt cggtttgatt    2100
tggtgggggg aggaaaggac ggggttcggc cgcgatgaac gagtctag              2148
```

<210> SEQ ID NO 11
<211> LENGTH: 3075
<212> TYPE: PRT
<213> ORGANISM: Monascus BCRC 38072

<400> SEQUENCE: 11

Met Tyr Val Gly Arg Ile Gly Ala Thr Thr Tyr Ile Ser Arg Pro Ala
1               5                   10                  15

Asp Ser Arg Ala Thr Pro Lys Val Ile Lys Thr Gln Gly Ser Ile Thr
                20                  25                  30

Thr Ser Asn Leu Thr Ser Leu Thr Thr Met Ala Gln Ser Thr Tyr Pro
            35                  40                  45

Asn Glu Pro Ile Val Val Gly Ser Gly Cys Arg Phe Pro Gly Gly
        50                  55                  60

Ala Asn Thr Pro Ser Lys Leu Trp Glu Leu Leu Arg Glu Pro Arg Asp
65                  70                  75                  80

Val Arg Ser Lys Ile Pro Lys Glu Arg Phe Asp Val Asp Ala Phe Tyr
                85                  90                  95

His Pro Asp Gly Lys His His Gly Arg Thr Asn Ala Pro Tyr Ala Tyr

```
                100                 105                 110
Met Leu Gln Glu Asp Leu Arg Ala Phe Asp Gly Pro Phe Asn Ile
            115                 120                 125
Gln Ala Gly Glu Ala Glu Ser Met Asp Pro Gln Gln Arg Leu Leu
            130                 135                 140
Glu Thr Val Tyr Glu Ala Val Ser Asp Ala Gly Met Arg Ile Gln Asp
145                 150                 155                 160
Leu Gln Gly Ser Ser Thr Ala Val Tyr Val Gly Met Met Thr His Asp
                165                 170                 175
Tyr Glu Thr Val Ser Thr Arg Asp Leu Glu Ser Ile Pro Thr Tyr Ser
            180                 185                 190
Ala Thr Gly Val Ala Val Ser Val Ala Ser Asn Arg Ile Ser Tyr Phe
            195                 200                 205
Phe Asp Trp His Gly Pro Ser Met Thr Ile Asp Thr Ala Cys Ser Ser
    210                 215                 220
Ser Leu Val Ala Val His Leu Ala Val Gln Gln Leu Arg Ser Gly Gln
225                 230                 235                 240
Ser Ser Met Ala Ile Ala Ala Gly Ala Asn Met Ile Leu Gly Pro Met
                245                 250                 255
Thr Phe Val Leu Glu Ser Lys Leu Asn Met Leu Ser Pro Ser Gly Arg
            260                 265                 270
Ser Arg Met Trp Asp Ala Gly Ala Asp Gly Tyr Ala Arg Gly Glu Ala
            275                 280                 285
Val Cys Ser Val Val Leu Lys Thr Leu Ser Gln Ala Leu Arg Asp Gly
    290                 295                 300
Asp Ser Ile Glu Cys Val Ile Arg Glu Thr Gly Val Asn Gln Asp Gly
305                 310                 315                 320
Arg Thr Thr Gly Ile Thr Met Pro Asn His Ser Ala Gln Glu Ala Leu
                325                 330                 335
Ile Arg Ala Thr Tyr Ser Lys Ala Gly Leu Asp Ile Thr Asn Pro Glu
            340                 345                 350
Asp Arg Cys Gln Phe Phe Glu Ala His Gly Thr Gly Thr Pro Ala Gly
            355                 360                 365
Asp Pro Gln Glu Ala Glu Ala Ile Ala Thr Ala Phe Phe Gly His Lys
    370                 375                 380
Lys Glu Ala Ser Asp Ala Glu Asn Ala Glu Thr Pro Leu Phe Val Gly
385                 390                 395                 400
Ser Val Lys Thr Val Val Gly His Thr Glu Gly Thr Ala Gly Leu Ala
                405                 410                 415
Gly Leu Met Lys Ala Ser Phe Ala Val Gln His Gly Val Ile Pro Pro
            420                 425                 430
Asn Leu Leu Phe Glu Asn Ile Ser Pro Arg Val Ala Pro Phe Tyr Ser
            435                 440                 445
Asn Leu Lys Ile Ala Thr Glu Thr Thr Pro Trp Pro Thr Ile Lys Pro
    450                 455                 460
Gly Gln Pro Arg Arg Val Ser Val Asn Ser Phe Gly Phe Gly Gly Thr
465                 470                 475                 480
Asn Ala His Ala Ile Ile Glu Glu Tyr Ile Lys Ser Asp Gln Lys Val
                485                 490                 495
Pro Ala Ser Arg Gln Pro Val Glu Tyr Ser Asp Ser Pro Ser Thr Leu
            500                 505                 510
Asn Leu Pro Leu Val Leu Ser Ala Lys Ser Gln Arg Ser Met Lys Thr
            515                 520                 525
```

```
Thr Leu Glu Ser Met Val Gln Phe Leu Gln Ser Asn Pro Glu Val Asn
            530                 535                 540

Leu Arg Asp Leu Ser Trp Thr Leu Leu Arg Lys Arg Ser Ile Leu Pro
545                 550                 555                 560

Phe Arg Arg Ala Ile Val Gly His Ser His Glu Ala Ile Arg Ala Ala
                565                 570                 575

Leu Glu Ala Ala Ile Glu Asp Gly Ile Val Val Ser Asp Phe Ser Ala
            580                 585                 590

Asp Val Lys Gly Lys Pro Ser Val Leu Gly Val Phe Thr Gly Gln Gly
            595                 600                 605

Ala Gln Trp Pro Gly Met Leu Lys Glu Leu Ile Val Gly Ser Ser Tyr
        610                 615                 620

Val Arg Ser Ile Ala Glu Glu Leu Asp His Ser Leu Gln Thr Leu Pro
625                 630                 635                 640

Glu Lys Tyr Arg Pro Ser Trp Thr Ile Leu Glu Gln Leu Met Leu Glu
            645                 650                 655

Asp Glu Ala Ser Asn Val Arg His Ala Ser Phe Ser Gln Pro Leu Cys
            660                 665                 670

Cys Ala Val Gln Ile Val Leu Val Arg Leu Leu Lys Ala Ala Gly Ile
        675                 680                 685

Gln Phe Ala Ala Val Val Gly His Ser Ser Gly Glu Ile Ala Cys Ala
    690                 695                 700

Phe Ala Thr Gly Leu Ile Ser Ala Ser Leu Ala Ile Arg Ile Ala His
705                 710                 715                 720

Leu Arg Gly Val Val Ser Ala Glu His Ala Ala Ser Ala Ser Gly Gly
            725                 730                 735

Arg Gly Ser Met Leu Ala Ala Gly Met Ser Tyr Glu Glu Ala Lys Glu
        740                 745                 750

Leu Cys Glu Leu Asp Ala Phe Glu Ser Arg Ile Cys Val Ala Ala Ser
    755                 760                 765

Asn Ser Pro Asp Ser Val Thr Phe Ser Gly Asp Ala Asp Ala Ile Glu
770                 775                 780

His Leu Gln Gly Val Leu Glu Asp Glu Ala Thr Phe Ala Arg Leu Leu
785                 790                 795                 800

Arg Val Asp Thr Ala Tyr His Ser His His Met Leu Pro Cys Ala Ala
            805                 810                 815

Pro Tyr Met Gln Ala Leu Glu Glu Cys Gly Cys Ala Val Ala Asp Gly
        820                 825                 830

Asp Gly Gln Val Glu Glu Gly Ser Trp Tyr Ser Ser Val Lys Asp Ser
    835                 840                 845

Asn Glu Pro Met Gly Leu Ala Asp Val Thr Ala Glu Tyr Trp Lys Asp
    850                 855                 860

Asn Leu Val Ser Pro Val Leu Phe Ser Gln Ala Val Gln Arg Ala Ala
865                 870                 875                 880

Ile Met His Arg Pro Leu Asp Val Gly Ile Glu Val Gly Cys His Pro
            885                 890                 895

Ala Leu Lys Gly Pro Cys Leu Ala Thr Ile Lys Asp Ala Leu Ser Asp
        900                 905                 910

Val Asp Leu Ala Tyr Thr Gly Cys Leu Glu Arg Gly Lys Asn Asp Met
    915                 920                 925

Asn Ala Phe Ser Gln Ala Leu Ala Tyr Leu Trp Glu Gln Phe Gly Ile
930                 935                 940
```

```
Pro Ser Leu Asp Ala Asp Arg Phe Ile Ser Thr Ile Ala Pro Glu Arg
945                 950                 955                 960

Ser Cys Val Ser Leu Ser Lys Gln Leu Pro Thr Tyr Ser Trp Asp His
            965                 970                 975

Ser Arg Ser Tyr Trp Thr Glu Ser Arg Ala Thr Arg Gln His Leu Arg
        980                 985                 990

Gly Pro Lys Pro His Leu Leu Leu Gly Lys Leu Ser Glu Tyr Ser Thr
    995                 1000                1005

Pro Leu Thr Phe Gln Trp Leu Asn Phe Val Arg Pro Arg Asp Ile
    1010                1015                1020

Glu Trp Leu Asp Gly His Ala Leu Gln Gly Gln Val Val Phe Pro
    1025                1030                1035

Ala Ala Gly Tyr Ile Val Met Ala Met Glu Ala Ala Met Glu Ile
    1040                1045                1050

Ala Asn Ser His Gln Val Gln Val Gln Leu Leu Glu Ile Leu Asp
    1055                1060                1065

Met Ser Ile Asp Lys Ala Val Val Phe Asp Asp Glu Asp Ser Leu
    1070                1075                1080

Val Glu Leu Asn Leu Thr Ala Glu Val Thr Ser Gly Ile Gly Lys
    1085                1090                1095

Gly Asp Arg Met Ile Leu Ser Phe Ile Ile Asp Ser Cys Leu Ser
    1100                1105                1110

Arg Glu Gly Asp Leu Ser Thr Ser Ala Lys Gly Gln Leu Val Val
    1115                1120                1125

Thr Leu Asp Glu Gly His Leu Gln Val Thr Pro Asp Asn Glu Lys
    1130                1135                1140

Gln Leu Leu Pro Pro Glu Glu Glu His Pro His Met Asn Arg
    1145                1150                1155

Val Asn Ile Asn Ser Phe Tyr His Glu Leu Asp Leu Met Gly Tyr
    1160                1165                1170

Asp Tyr Ser Lys Asp Phe Arg Arg Leu His Ser Met Arg Arg Ala
    1175                1180                1185

Asp Ala Arg Ala Ser Gly Ile Leu Glu Phe Ile Pro Leu Asn Asp
    1190                1195                1200

Glu Val His Gly Arg Pro Leu Leu Leu His Pro Ala Pro Leu Asp
    1205                1210                1215

Ile Ala Phe Gln Thr Val Ile Gly Ala Tyr Ser Ser Pro Gly Asp
    1220                1225                1230

Arg Arg Leu Arg Cys Leu Tyr Val Pro Thr His Ile Asp Arg Ile
    1235                1240                1245

Ala Leu Val Pro Ser Leu Cys Leu Ala Thr Ala Ala Ser Gly Cys
    1250                1255                1260

Asp Lys Ile Ala Phe Asn Thr Ile Asn Thr Tyr Asp Lys Gly Asp
    1265                1270                1275

Phe Leu Ser Gly Asp Ile Val Ala Phe Asp Ala Glu Gln Thr Ser
    1280                1285                1290

Leu Phe His Val Glu Asn Ile Val Phe Lys Pro Phe Ser Pro Pro
    1295                1300                1305

Thr Ala Ser Thr Asp His Pro Ile Phe Ala Lys Trp Ser Trp Gly
    1310                1315                1320

Pro Leu Thr Pro Glu Thr Leu Leu Asp Asn Pro Asn His Trp Ala
    1325                1330                1335

Thr Ala Gln Asp Lys Glu Ala Ile Pro Ile Ile Glu Arg Ile Val
```

-continued

```
            1340                1345                1350

Tyr Phe Tyr Ile Lys Leu Phe Leu Gln Gln Leu Thr Arg Glu Asp
    1355                1360                1365

Arg Glu Gln Ala Ala Phe His Leu Gln Arg Gln Ile Val Trp Cys
    1370                1375                1380

Glu Gln Val Val Ala Asp Ala His Glu Gly Arg His Gln Trp Tyr
    1385                1390                1395

Asp Ala Ala Trp Glu Asn Asp Thr Glu Ala Gln Ile Glu Gln Leu
    1400                1405                1410

Cys Ala Arg Ser Ser Tyr His Pro His Val Arg Leu Val Gln Arg
    1415                1420                1425

Val Gly Gln Asn Leu Leu Ala Thr Ile Arg Ser Asn Gly Asn Pro
    1430                1435                1440

Phe Asp Leu Met Asp His Asp Gly Leu Leu Thr Glu Phe Tyr Thr
    1445                1450                1455

Asn Thr Leu Ser Phe Gly Pro Ala Leu His Tyr Ala Gln Asp Leu
    1460                1465                1470

Val Gly Gln Ile Ala His Arg Tyr Gln Ser Met Asp Ile Leu Glu
    1475                1480                1485

Ile Gly Ala Gly Thr Gly Gly Ala Thr Lys Tyr Val Leu Ala Thr
    1490                1495                1500

Pro Gln Leu Gly Phe Asn Ser Tyr Thr Tyr Thr Asp Ile Ser Thr
    1505                1510                1515

Gly Phe Phe Glu Lys Ala Arg Glu Gln Phe Ala Ala Phe Glu Asp
    1520                1525                1530

Arg Met Glu Phe Glu Pro Leu Asp Ile Arg Arg Ser Pro Ala Glu
    1535                1540                1545

Gln Gly Phe Thr Glu His Val Tyr Asp Leu Ile Ile Ala Ser Asn
    1550                1555                1560

Val Leu His Ala Thr Pro Asp Leu Glu Lys Thr Met Ala His Ala
    1565                1570                1575

Arg Ser Leu Leu Lys Pro Gly Gly Gln Met Val Ile Leu Glu Ile
    1580                1585                1590

Thr His Arg Asn His Thr Arg Leu Gly Phe Ile Phe Gly Leu Phe
    1595                1600                1605

Ala Asp Trp Trp Ala Gly Ile Asp Asp Gly Arg Thr Met Glu Pro
    1610                1615                1620

Phe Val Ser Phe Asp Arg Trp Asp Glu Ile Leu Lys His Val Gly
    1625                1630                1635

Phe Ser Gly Ile Asp Ser Arg Thr Lys Asp Arg Asp Ala Asp Leu
    1640                1645                1650

Phe Pro Thr Ser Val Phe Ser Thr His Ala Val Asn Ser Thr Ile
    1655                1660                1665

Asp Tyr Leu His Lys Pro Leu Asp Ala Pro Val Lys Asp Ser Tyr
    1670                1675                1680

Pro Pro Leu Val Val Val Gly Gly Gln Thr Pro Lys Thr Gln Arg
    1685                1690                1695

Ile Leu Asp Glu Ile Lys Ala Val Met Pro Asn Arg Gln Ile Gln
    1700                1705                1710

Leu His Gln Arg Leu Val Asp Leu Leu Asp Ala Glu Asp Met Gln
    1715                1720                1725

Ala Lys Phe Thr Phe Val Val Leu Thr Glu Leu Asp Glu Glu Leu
    1730                1735                1740
```

-continued

```
Phe Ala Gly Leu Thr Glu Asp Ser Phe Glu Ala Val Lys Leu Leu
1745                1750                1755

Leu Met Tyr Ala Gly Asn Met Leu Trp Leu Thr Glu Asn Ala Trp
1760                1765                1770

Val Lys Arg Pro His Gln Ala Ser Thr Ile Gly Met Leu Arg Ser
1775                1780                1785

Ile Arg Arg Glu His Pro Asp Ile Gly Val His Ile Met Asp Val
1790                1795                1800

Asp Ser Ala Glu Asn Leu Asp Ala His Phe Leu Val Glu Gln Val
1805                1810                1815

Leu Arg Leu Glu Glu Asp Ile Asp Glu Leu Ala Ala Thr Thr Thr
1820                1825                1830

Trp Thr Gln Glu Pro Glu Val Phe Trp Cys Asn Gly Arg Ala Trp
1835                1840                1845

Ile Pro Arg Leu Lys His Asp Lys Ser Arg Asn Asn Arg Met Asn
1850                1855                1860

Ser Ser Arg Arg Gln Ile Phe Glu Thr Leu Asn Pro Ser Lys Ile
1865                1870                1875

Pro Val Ala Leu Lys Lys Ala Ala Ala Ser Ser Tyr Tyr Leu
1880                1885                1890

Glu Ser Ala Glu Thr Trp Pro Val Pro Gly Ala Val Thr Ala Gly
1895                1900                1905

Asp Arg Lys Thr Val His Val Arg Leu Ser His Pro His Ala Leu
1910                1915                1920

Arg Val Gly His Leu Gly Phe Phe Tyr Leu Val Gln Gly His Val
1925                1930                1935

Leu Lys Gly Asp Gln Ala Leu Pro Val Val Ala Leu Ala Glu Arg
1940                1945                1950

Asn Ala Ser Ile Val His Val Arg Ser Asp Tyr Val His Val Leu
1955                1960                1965

Glu Asp Thr Ala Val Ser Ala Asn Asn Gly Ser Phe Ile Leu Ala
1970                1975                1980

Ala Ala Ala Ala Val Leu Ala Glu Thr Val Ile His Ser Ala Lys
1985                1990                1995

Ser Leu Gly Ala Asp Ala Ser Val Leu Val Leu Asn Ala Pro Gly
2000                2005                2010

Phe Cys Ala Gln Thr Leu Leu Arg Ala Ala Arg Asp Ser Gly Leu
2015                2020                2025

Arg Val His Leu Ala Thr Thr Ser Ser Ser Thr Asp Pro Ser Pro
2030                2035                2040

Gly Ala Asp Arg Cys Val Arg Leu His Pro Arg Asp Thr Asp Arg
2045                2050                2055

Arg Leu Lys Gln Leu Leu Pro Arg Gly Thr Gln Ala Phe Phe Asp
2060                2065                2070

Leu Ser Thr Asp Pro Ser Ser Glu Gly Leu Thr Gln Arg Leu Pro
2075                2080                2085

Asn Val Leu Ile Pro Ser Cys Val Arg His Ser Thr Glu Tyr Leu
2090                2095                2100

Leu Arg Asp Thr Ala Ser Ala Gly Gly Lys Ala Thr Leu Pro Ala
2105                2110                2115

Ala Tyr Trp Glu Arg Val Ala Ser Leu Ala Asn His Ser Leu Ser
2120                2125                2130
```

```
Thr His Phe Lys Glu Asn Asp Asn Ala Ser Asn Gly Cys Gln Val
2135                2140                2145

Leu Ser Cys Thr Asp Ile Val Ala Arg Asn Asn Lys Ser Arg Leu
2150                2155                2160

Asn Ala Ser Thr Val Ile Ser Trp Pro Asp Asp Ala Ala Leu Pro
2165                2170                2175

Ala Arg Ile Arg Pro Ile Asp Thr Glu Thr Leu Phe Ala Ala Glu
2180                2185                2190

Lys Thr Tyr Leu Leu Val Gly Leu Thr Gly Asp Leu Gly Arg Ser
2195                2200                2205

Leu Gly Arg Trp Met Val Leu His Gly Ala Arg Arg Ile Val Leu
2210                2215                2220

Thr Ser Arg Asn Pro Gln Val Ser Pro Asn Trp Val Ala His Val
2225                2230                2235

Glu Glu Leu Gly Gly Gln Val Thr Val Leu Ser Met Asp Val Thr
2240                2245                2250

Ser Glu Asp Ser Val Asp Ser Gly Leu Ala Lys Leu Gln Asp Leu
2255                2260                2265

Lys Leu Pro Pro Ile Gly Gly Ile Ala Phe Gly Pro Leu Val Leu
2270                2275                2280

Gln Asp Val Met Leu Lys Asn Met Asp Leu Gln Met Met Glu Met
2285                2290                2295

Val Leu Lys Pro Lys Val Glu Gly Ala Arg Ile Leu His Glu Lys
2300                2305                2310

Phe Ser Asp Pro Ala Ser Ser Asn Pro Leu Asp Phe Phe Val Met
2315                2320                2325

Phe Ser Ser Ile Val Ala Val Met Gly Asn Pro Gly Gln Ala Asn
2330                2335                2340

Tyr Ser Ala Ala Asn Cys Tyr Leu Gln Ala Leu Ala Gln Arg Arg
2345                2350                2355

Cys Ala Ser Gly Leu Ala Ala Ser Thr Ile Asp Ile Gly Ala Val
2360                2365                2370

Tyr Gly Val Gly Phe Val Thr Arg Ala Glu Leu Glu Glu Asp Phe
2375                2380                2385

Asn Ala Ile Arg Phe Met Phe Asp Ser Val Glu Glu His Glu Leu
2390                2395                2400

His Ser Leu Phe Ala Glu Ala Val Val Ser Gly Arg Arg Ala Met
2405                2410                2415

His Gln Gln Gln Phe Lys Thr Val Leu Asp Met Ala Asp Ile
2420                2425                2430

Glu Leu Thr Thr Gly Ile Pro Pro Leu Asp Pro Thr Leu Lys Asp
2435                2440                2445

Arg Ile Thr Phe Phe Asp Asp Ala Arg Val Gly Asn Phe Lys Ile
2450                2455                2460

Pro Glu Arg Arg Gly Lys Ala Gly Asp Asn Ala Ala Gly Ser Lys
2465                2470                2475

Gly Ser Val Lys Glu Gln Leu Leu Gln Ala Thr Ser Leu Asp Gln
2480                2485                2490

Val Arg Gln Ile Val Ile Asp Gly Leu Ser Glu Lys Leu Arg Val
2495                2500                2505

Thr Leu Gln Ile Pro Asp Gly Glu Ser Val His Pro Thr Ile Pro
2510                2515                2520

Leu Ile Asp Gln Gly Val Asp Ser Leu Gly Ala Val Thr Val Gly
```

-continued

```
            2525                2530                2535

Thr Trp Phe Ser Lys Gln Leu Tyr Leu Asp Leu Pro Leu Leu Arg
    2540                2545                2550

Val Leu Gly Gly Ala Ser Val Ala Asp Leu Ala Asp Asp Ala Ala
    2555                2560                2565

Ala Arg Leu Pro Pro Ser Ser Ile Pro Leu Val Ala Ala Ser Glu
    2570                2575                2580

Gly Gly Ala Glu Thr Ser Asp Asn Asp Thr Ser Gly Pro Glu Gly
    2585                2590                2595

Thr Asp Leu Ser Ala Ser Thr Thr Ile Thr Glu Pro Ser Ser Ala
    2600                2605                2610

Asp Glu Glu Asp Glu Lys Gln Glu Asp Asn Asp Asn Ser Val
    2615                2620                2625

Leu Ala Leu His Pro Leu Ser Leu Gly Gln Glu Tyr Ala Trp Arg
    2630                2635                2640

Leu Gln Lys Ala Ala Asp Asp Ser Thr Ile Phe Asn Asn Thr Ile
    2645                2650                2655

Gly Met Phe Met Thr Gly Ser Ile Asp Ala Lys Arg Leu Ser Lys
    2660                2665                2670

Ala Leu Arg Ala Val Leu Arg Arg His Glu Ile Phe Arg Thr Gly
    2675                2680                2685

Phe Ala Ala Val Gly Asn Asn Ala Asp Ala Thr Ser Leu Ala Gln
    2690                2695                2700

Ile Val Phe Gly Arg Thr Lys Asn Lys Val Gln Val Ile Gln Val
    2705                2710                2715

Ala Asp Arg Ala Gly Ala Glu Glu Gly Tyr Arg Gln Leu Val Gln
    2720                2725                2730

Thr Gln Tyr Asp Ile Thr Ala Gly Asp Thr Leu Arg Leu Val Asp
    2735                2740                2745

Phe Phe Trp Gly Lys Asp Glu His Leu Phe Val Val Ala Tyr His
    2750                2755                2760

Arg Phe Val Gly Asp Gly Ser Thr Thr Glu Asn Ile Phe Val Glu
    2765                2770                2775

Ala Ser Gln Leu Tyr Gly Val Thr Leu Asp Lys His Val Pro
    2780                2785                2790

Gln Phe Ala Asp Leu Ala Thr Arg Gln Arg Glu Ala Leu Glu Ser
    2795                2800                2805

Gly Gln Met Asp Ala Asp Leu Ala Tyr Trp Glu Ser Met His His
    2810                2815                2820

Gln Pro Thr Gly Val Val Ser Pro Val Leu Pro Arg Met Leu Leu
    2825                2830                2835

Gly Glu Asp Gly Leu Asn Ser Pro Asn His Ala Arg Gln Pro Asn
    2840                2845                2850

Ser Trp Lys Gln His Glu Ala Ile Ala Arg Leu Asp Pro Met Val
    2855                2860                2865

Ala Phe Arg Ile Arg Glu Arg Ser Arg Lys His Lys Ala Thr Pro
    2870                2875                2880

Met Gln Phe Tyr Leu Ala Ala Tyr His Val Leu Leu Ala Arg Leu
    2885                2890                2895

Thr Gly Ser Ser Asp Phe Ser Ile Gly Leu Ala Asp Thr Asn Arg
    2900                2905                2910

Thr Asn Val Asp Glu Leu Ala Gly Met Gly Phe Phe Ala Asn Leu
    2915                2920                2925
```

```
Leu Pro Leu Arg Phe Arg Asn Phe Val Pro His Ile Thr Phe Gly
    2930                2935                2940

Glu His Leu Val Ala Thr Lys Asp Lys Val Arg Glu Ala Met Gln
    2945                2950                2955

His Ala Arg Val Pro Tyr Gly Val Leu Glu Arg Leu Gly Phe
    2960                2965                2970

Glu Val Pro Gly Ala Thr Ala Glu Thr Ala Glu Pro Ala Pro Leu
    2975                2980                2985

Phe Gln Ala Val Phe Asp Tyr Lys Gln Gly Gln Ala Glu Ser Gly
    2990                2995                3000

Ser Ile Gly Ser Ala Lys Met Thr Glu Val Ile Ala Thr Arg Glu
    3005                3010                3015

Arg Thr Pro Tyr Asp Val Val Leu Glu Met Ser Asp Asp Pro Thr
    3020                3025                3030

Lys Asp Pro Leu Leu Thr Val Lys Leu Gln Ser Ser Val Tyr Glu
    3035                3040                3045

Val His His Pro Arg Ala Phe Leu Glu Ser Tyr Ile Ser Ile Leu
    3050                3055                3060

Ser Met Phe Ser Met Asn Pro Ala Leu Lys Leu Ala
    3065                3070                3075

<210> SEQ ID NO 12
<211> LENGTH: 2547
<212> TYPE: PRT
<213> ORGANISM: Monascus BCRC 38072

<400> SEQUENCE: 12

Met Lys Ala Thr Ala Ala Ser Gly Thr Pro Thr Pro Ile Ala Val Val
1               5                   10                  15

Gly Met Gly Cys Arg Phe Ala Gly Gly Ala Thr Asp Pro Gln Ala Leu
                20                  25                  30

Trp Lys Leu Leu Glu Gln Gly Gly Ser Thr Trp Ser Lys Thr Pro Ser
        35                  40                  45

Ser Arg Phe Asn Val Ser Gly Val Tyr His Pro Asn Gly Gln Arg Val
    50                  55                  60

Gly Ser Met His Val Arg Gly Gly His Phe Leu Asp Gln Asp Pro Ala
65                  70                  75                  80

Leu Phe Asp Ala Ser Phe Phe Asn Met Thr Ser Glu Val Ala Ser Cys
                85                  90                  95

Met Asp Pro Gln Gln Arg Leu Ile Leu Glu Val Val Tyr Glu Ala Leu
                100                 105                 110

Glu Ala Ala Gly Ile Pro Leu Glu Ser Val Ala Gly Ser Asn Thr Ala
        115                 120                 125

Val Phe Ser Gly Ala Met Tyr His Asp Tyr Gln Asp Ser Leu His Arg
    130                 135                 140

Asn Pro Glu Thr Leu Pro Arg Tyr Phe Ile Thr Gly Asn Ala Gly Thr
145                 150                 155                 160

Met Met Ser Ser Arg Val Ser His Phe Tyr Asp Leu Arg Gly Pro Ser
                165                 170                 175

Val Thr Val Asp Thr Ala Cys Ser Thr Thr Leu Thr Ala Leu His Leu
                180                 185                 190

Ala Ile Gln Ser Ile Arg Ala Gly Glu Ala Asp Met Ala Ile Val Ala
        195                 200                 205

Gly Ser Asn Leu Leu Leu Asn Ser Asp Val Phe Val Thr Met Ser Asn
```

-continued

```
            210                 215                 220
Leu Gly Phe Leu Ser Pro Asp Gly Ile Ser Tyr Ser Phe Asp Pro Arg
225                 230                 235                 240

Ala Asn Gly Tyr Gly Arg Gly Glu Gly Val Ala Ala Ile Ile Leu Lys
                245                 250                 255

Ala Leu Pro Arg Ala Leu Arg Asp Gly Asp Pro Ile Arg Leu Val Val
            260                 265                 270

Arg Glu Thr Ala Leu Asn Gln Asp Gly Arg Thr Pro Ala Ile Thr Gly
        275                 280                 285

Pro Ser Pro Glu Ala Gln Ala Cys Leu Ile Arg Glu Cys Tyr Gln Lys
290                 295                 300

Ala Gly Leu Asp Pro Arg Gln Thr Ser Tyr Val Glu Ala His Gly Thr
305                 310                 315                 320

Gly Thr Pro Thr Gly Asp Pro Leu Glu Leu Ala Ala Ile Ser Ala Ala
                325                 330                 335

Phe Gln Gly Gln Pro Leu Gln Ile Gly Ser Val Lys Ala Asn Leu Gly
            340                 345                 350

His Thr Glu Ala Ala Ser Gly Leu Ala Ser Val Met Lys Val Ala Leu
        355                 360                 365

Ala Leu Glu Lys Gly Ile Val Pro Pro Ser Ala Arg Phe Leu Gln Pro
370                 375                 380

Ser Lys Lys Leu Leu Glu Glu Arg Lys Phe Gln Ile Pro Leu Ser Ser
385                 390                 395                 400

Gln Leu Trp Leu Pro Ile Asp Gly Ile Cys Arg Ala Ser Ile Asn Asn
                405                 410                 415

Phe Gly Phe Gly Gly Ala Asn Ala His Ala Ile Val Glu Arg Tyr Asp
            420                 425                 430

Pro Ala Ala Arg Ile Ser Thr Ser Lys Pro Asn Gly His Ile Arg Pro
        435                 440                 445

His Asp Ser His Val Glu Ala Asp Arg Gly Lys Ile Tyr Val Leu Ser
450                 455                 460

Ala Lys Asp Glu His Ser Cys Gln Glu Met Ile Ser Arg Leu Arg Asp
465                 470                 475                 480

Tyr Leu Asn Arg Ala Asn Pro Thr Asp Glu Arg Gln Phe Leu Ala Asn
                485                 490                 495

Met Ala Tyr Thr Leu Ala Ser Arg Arg Ser Asn Leu Arg Trp Lys Ala
            500                 505                 510

Ala Cys Arg Ala His Ser Leu Ala Ser Leu Leu Ser Val Leu Val Ser
        515                 520                 525

Asp Gly Thr Arg Pro Arg Arg Ser Ala Glu Lys Ala Arg Leu Gly Trp
530                 535                 540

Val Phe Thr Gly Gln Gly Ala Gln Trp Phe Ala Met Gly Arg Glu Leu
545                 550                 555                 560

Ile Glu Ala Tyr Pro Val Phe Lys Glu Ala Leu Ile Glu Cys Asp Gly
                565                 570                 575

Tyr Ile Lys Gly Met Gly Ala Asn Trp Ser Ile Asp Glu Leu Arg
            580                 585                 590

Arg Gly Glu Ala Glu Ser Arg Val Asn Glu Ala Glu Phe Ser Leu Pro
        595                 600                 605

Leu Ser Thr Ala Ile Gln Val Ala Leu Val Arg Leu Leu Trp Ser Trp
610                 615                 620

Gly Ile Arg Pro Ala Ala Ile Thr Ser His Ser Ser Gly Glu Val Ala
625                 630                 635                 640
```

-continued

```
Ala Ala Tyr Ala Val Gly Ala Phe Ser Ala Arg Ser Ala Ile Gly Ile
            645                 650                 655
Ser Tyr Ile Arg Gly Ala Leu Ile Ala Lys Thr Gln Pro Ala Pro Thr
        660                 665                 670
Thr Lys Gly Gly Met Leu Ala Val Gly Leu Ser Arg Ser Glu Val Gly
    675                 680                 685
Glu Tyr Ile Thr Arg Val Gln Gln Gly Glu Tyr Leu Val Val
690                 695                 700
Gly Cys Ile Asn Ser Pro Ser Asn Val Thr Val Ser Gly Asp Leu Ser
705                 710                 715                 720
Ala Val Val Arg Leu Glu Glu Leu Leu His Ala Asp Gln Ile Phe Ala
                725                 730                 735
Arg Arg Leu Lys Val Thr Gln Ala Phe His Ser His His Met Gln Pro
            740                 745                 750
Leu Ser Gly Glu Phe Arg Glu Ala Leu Val Glu Val Phe Asn Ala Asp
        755                 760                 765
Ile Thr Asp Thr Thr Asn Ala Cys Gln Asp Val Val Tyr Ala Ser Pro
770                 775                 780
Lys Thr Gly Lys Arg Leu Asp Asp Cys Asn His Leu Arg Asp Pro Met
785                 790                 795                 800
His Trp Val Glu Ser Met Leu Phe Pro Val Phe Glu Ser Ser Phe
                805                 810                 815
Arg Glu Met Cys Phe Asp Arg Lys Asp Gln Ala Gln Glu Val Asp Lys
            820                 825                 830
Ile Ile Glu Ile Gly Pro His Gly Val Leu Ser Gly Ala Ile Lys Gln
        835                 840                 845
Ile Leu Gln Leu Pro Glu Leu Ala Ala Phe Asp Ile Ser Tyr Leu Ser
    850                 855                 860
Cys Leu Ser Arg Gly Lys Ser Ala Val Asp Thr Ile Gln Leu Leu Ala
865                 870                 875                 880
Met Asp Leu Leu Gln Gly Gly Tyr Pro Val Asp Leu Asn Ala Val Asn
                885                 890                 895
Phe Pro Tyr Gly Cys Glu Ala Ala Glu Val Gln Val Leu Ser Asp Leu
            900                 905                 910
Pro Thr Tyr Pro Trp Asn His Lys Thr Arg Tyr Trp Lys Glu Pro Arg
        915                 920                 925
Ile Ser Arg Ala Ala Arg Gln Arg Lys Ile Pro Val His Asp Leu Ile
    930                 935                 940
Gly Val Gln Glu Pro Leu Cys Pro Pro Leu Leu His Leu Trp Gln Asn
945                 950                 955                 960
Val Leu Arg Ile Ser Asp Val Pro Trp Ile Arg Asp His Val Val Gly
                965                 970                 975
Ser Arg Ile Leu Phe Pro Gly Ala Gly Phe Ile Ser Met Val Ile Asp
            980                 985                 990
Gly Leu Ser Gln Ile Cys Asn His Asp Pro Glu Thr Cys Gly Leu Ser
            995                 1000                1005
Tyr Ile Leu Arg Asp Val Asp Leu Ala Gln Ala Leu Ile Leu Pro
    1010                1015                1020
Thr Asp Gly Asp Glu Gly Val Asp Leu Arg Leu Thr Ile Arg Ala
    1025                1030                1035
Ala Asp Gln Lys Ser Leu Gly Met Arg Asp Trp Gln Arg Phe Ser
    1040                1045                1050
```

-continued

```
Val Tyr Ser Ile Ala Gly Asp Lys Asp Trp Thr Glu His Cys
    1055                1060                1065

Thr Gly Leu Ile Arg Ala Gln Val Asp His Pro Val Ser Ser Ser
    1070                1075                1080

Ser Ile Gln Gln Lys Thr Asn Pro Pro Gln Trp Ser Arg Lys Met
    1085                1090                1095

Ala Pro Gln Asp Leu Trp Ala Ser Leu His Ala Thr Gly Ile Cys
    1100                1105                1110

His Gly Pro Leu Phe Gln Asn Ile Glu Arg Ile Glu Ser Asp Gly
    1115                1120                1125

Gln Ala Ser Trp Cys Thr Leu Thr Val Ala Asp Thr Val Ala Thr
    1130                1135                1140

Met Pro His Ala Tyr Glu Ser Gln His Ile Val His Pro Thr Thr
    1145                1150                1155

Leu Asp Ser Ala Ile Gln Ala Ala Tyr Thr Val Leu Pro Phe Met
    1160                1165                1170

Gly Thr Leu Met Lys Thr Ala Met Val Pro Ser Arg Ile Gly Gly
    1175                1180                1185

Met Lys Ile Pro Ala Ser Phe Ala Ser Leu Glu Pro Gly Asp Met
    1190                1195                1200

Leu Cys Ala Gln Ala Lys Ile Lys Asn Gln Gly Leu Ser Ala Phe
    1205                1210                1215

Thr Thr Asp Val Ala Val Phe Asn Glu Ser Asp Met Asp Glu Glu
    1220                1225                1230

Ala Gly Ile Glu Leu Glu Gly Leu Thr Phe Gln Ser Leu Gly Ala
    1235                1240                1245

Val Ile Ser Asp Ser Arg Arg Asp Leu Thr Glu Asn Glu Ser Thr
    1250                1255                1260

Tyr Ser Ser Trp His Trp Ala Pro Asp Ile Thr Leu Thr Asn Ser
    1265                1270                1275

Thr Trp Leu Glu Arg Ile Leu Ser Thr Gly Thr Gln Ser Gln Glu
    1280                1285                1290

Ile Gly Val Met Leu Glu Leu Arg Arg Cys Thr Val His Phe Ile
    1295                1300                1305

Gln Glu Ala Ile Glu Asn Leu Thr Thr Glu Asp Val Glu Arg Leu
    1310                1315                1320

Ser Gly His Leu Val Lys Phe Tyr Cys Trp Met Gln Ala Gln Leu
    1325                1330                1335

Ala Cys Ala Thr Asn Gly Glu Leu Gly Gln Asp Ser Ala Asp Trp
    1340                1345                1350

Leu Arg Asp Ser Glu Gln Glu Arg Gln Ser Leu Arg Ser Arg Val
    1355                1360                1365

Val Ala Ala Thr Asn Asn Gly Glu Met Ile Cys Arg Leu Gly Pro
    1370                1375                1380

Lys Leu Ser Ala Ile Leu Arg Gly Glu Leu Asp Pro Leu Glu Leu
    1385                1390                1395

Met Met Asp Gly Gln Leu Leu Ser Arg Tyr Tyr Ile Arg Ala Ile
    1400                1405                1410

Lys Trp Ser Arg Ser Asn Thr Gln Ala Ser Glu Leu Val Arg Leu
    1415                1420                1425

Cys Cys His Lys Asn Pro Arg Ala Arg Ile Leu Glu Ile Gly Gly
    1430                1435                1440

Gly Thr Gly Gly Cys Thr Gln Leu Ile Val Asn Ala Leu Gly Pro
```

-continued

```
        1445                1450                1455

Thr Lys Pro Val Gly Arg Tyr Asp Phe Thr Asp Val Ser Ala Gly
    1460                1465                1470

Phe Phe Glu Ala Ala Arg Lys Arg Phe Ser Gly Trp Gln Asp Val
    1475                1480                1485

Met Asp Phe Arg Lys Leu Asp Ile Glu Gly Asp Pro Glu Val Gln
    1490                1495                1500

Gly Phe Asp Cys Gly Ser Tyr Asp Val Val Leu Ala Cys Gln Val
    1505                1510                1515

Leu His Ala Thr Ser Asn Met Gln Arg Thr Leu Asn Asn Val Arg
    1520                1525                1530

Lys Leu Leu Lys Pro Gly Gly Lys Leu Ile Leu Val Glu Thr Thr
    1535                1540                1545

Arg Asp Gln Leu Asp Leu Phe Phe Thr Phe Gly Leu Leu Pro Gly
    1550                1555                1560

Trp Trp Leu Ser Glu Glu Pro Glu Arg Gln Leu Thr Pro Ser Leu
    1565                1570                1575

Ser Pro Glu Leu Trp Arg Ser Val Leu Ser Ala Thr Gly Phe Ser
    1580                1585                1590

Gly Val Asp Leu Glu Val Arg Asp Cys Asp Ser Asp Glu Phe Tyr
    1595                1600                1605

Met Ile Ser Thr Met Met Ser Thr Ala Thr Pro Gly Thr Pro Ala
    1610                1615                1620

Thr Thr Leu Asn Gly Pro Ala Glu Val Leu Leu Val His Ala Gly
    1625                1630                1635

Ser Pro Pro Pro Met Asp Trp Leu Gln Asn Leu Gln Val Ala Leu
    1640                1645                1650

Gly Gly Lys Asn Ser Ser Ile Thr Ser Leu Lys Ala Leu Gln Gly
    1655                1660                1665

Val Ser Asp Leu Lys Gly Lys Met Cys Val Phe Leu Gly Glu Met
    1670                1675                1680

Asp Arg Thr Leu Leu Glu Ser Val Val Ser Asp Asp Phe Thr Ser
    1685                1690                1695

Leu Thr Ser Met Leu Gln Tyr Ser Gln Gly Thr Leu Trp Val Thr
    1700                1705                1710

Arg Gly Ala Ala Met Ala Ser Asp Asp Pro Arg Lys Ala Leu His
    1715                1720                1725

Leu Gly Leu Leu Arg Thr Leu Arg Asn Glu Asn His Gly Arg Arg
    1730                1735                1740

Phe Val Ser Leu Asp Leu Asp Pro Leu Arg Asp Pro Trp Thr Ala
    1745                1750                1755

Gln Ser Cys Asp Ala Ile Val Asn Val Leu Asn Ala Val Gly Ala
    1760                1765                1770

Ser His Glu Lys Glu Phe Glu Tyr Ala Glu Arg Asp Gly Thr Ile
    1775                1780                1785

His Val Pro Arg Thr Phe Ser Asp Ser Ser Ser Glu Lys Glu
    1790                1795                1800

Asp Leu Val Val Leu Glu Pro Phe Gln Asn Glu Thr Arg Leu Val
    1805                1810                1815

Arg Leu Asp Val Gln Thr Pro Gly Leu Leu Asp Ser Leu His Phe
    1820                1825                1830

Lys Leu Cys Ser Ala Asp Glu Ala Trp Ser Ser Glu Leu Pro Glu
    1835                1840                1845
```

-continued

```
Asp Trp Val Glu Ile Glu Pro Arg Ala Phe Gly Leu Asn Phe Arg
    1850                1855                1860

Asp Ile Met Val Ala Met Gly Gln Leu Glu Ser Asn Arg Val Met
    1865                1870                1875

Gly Phe Glu Cys Ala Gly Val Val Thr Arg Leu Ser Lys Ala Ala
    1880                1885                1890

Thr Thr Gly Ala Gly Gly Leu Ala Ile Gly Asp Arg Val Cys Ala
    1895                1900                1905

Leu Met Lys Gly His Trp Ala Ser Arg Val Arg Thr Ala Arg Thr
    1910                1915                1920

Asn Val Ile Cys Ile Pro Gly Thr Leu Ser Phe Glu Gln Ala Ala
    1925                1930                1935

Ser Ile Pro Leu Ala Phe Thr Thr Ala Tyr Thr Ser Leu Tyr Thr
    1940                1945                1950

Val Ala Arg Leu Gln Arg Gly Glu Lys Val Leu Ile His Gly Gly
    1955                1960                1965

Ala Gly Gly Val Gly Gln Ala Ala Ile Ile Leu Ala Gln Leu Val
    1970                1975                1980

Gly Ala Glu Val Phe Thr Thr Ala Gly Thr His Ser Lys Arg Asn
    1985                1990                1995

Phe Leu Ile Asp Lys Phe Lys Leu Ala Pro Asp His Val Phe Ser
    2000                2005                2010

Ser Arg Asp Ser Gly Phe Ile Glu Gly Ile Arg Ala Cys Thr Asn
    2015                2020                2025

Gly Lys Gly Val Asp Val Val Leu Asn Ser Leu Ala Gly Pro Leu
    2030                2035                2040

Leu Gln Tyr Ser Phe Asp Cys Leu Val Asn Phe Gly Arg Phe Val
    2045                2050                2055

Glu Ile Gly Lys Lys Asp Leu Glu Gln Asn Ser Arg Leu Asn Met
    2060                2065                2070

Ala Thr Phe Ala Arg Asn Val Ser Phe Ser Ser Ile Asp Ile Leu
    2075                2080                2085

Tyr Trp Glu Glu Ala Lys Ser Ala Glu Ile Phe Arg Ala Leu Thr
    2090                2095                2100

Glu Ile Met Arg Leu Leu Glu Gln Lys Thr Ile Asp Leu Ile Gly
    2105                2110                2115

Pro Ile Ser Glu Tyr Pro Met Ser Ala Ile Glu Lys Ala Phe Arg
    2120                2125                2130

Thr Met Gln Ser Gly Gln His Val Gly Lys Leu Val Val Ala Thr
    2135                2140                2145

Ala Glu Thr Asp Met Ile Pro Val Arg Arg Gly Thr Met Pro Val
    2150                2155                2160

Ala Leu Lys Leu Asp Ala Ser Tyr Leu Ile Val Gly Gly Leu Gly
    2165                2170                2175

Gly Ile Gly Arg Arg Ile Cys Glu Trp Met Val Asp His Gly Ala
    2180                2185                2190

Arg His Leu Leu Ile Leu Ser Arg Ser Gly Arg Thr Asp Pro Phe
    2195                2200                2205

Val Thr Gly Leu Gln Lys Arg Gly Cys Val Val Arg Ile His Ser
    2210                2215                2220

Cys Asp Val Ala Asp Glu Ser Gln Leu His Ala Val Leu Gln Gln
    2225                2230                2235
```

```
Cys His Glu Asp Asn Met Pro Pro Ile Arg Gly Ile Ile Gln Ala
2240                2245                2250

Ala Met Val Leu Lys Asp Ala Leu Val Ser Gln Met Thr Ala Asp
2255                2260                2265

Asp Phe His Val Ala Leu Arg Pro Lys Val Gln Gly Ser Trp Asn
2270                2275                2280

Leu His Lys Ile Ala Ser Glu Val Asp Phe Phe Ile Met Leu Ser
2285                2290                2295

Ser Leu Val Gly Val Met Gly Gly Ala Gly Gln Ala Asn Tyr Ala
2300                2305                2310

Ala Ala Gly Ala Phe Gln Asp Ala Leu Ala Gln His Arg Val Ala
2315                2320                2325

Gln Gly Lys Pro Ala Val Thr Ile Asp Leu Gly Met Val Lys Ser
2330                2335                2340

Ile Gly Tyr Val Ala Glu Thr Asp Pro Ala Val Ala Glu Arg Leu
2345                2350                2355

Ala Arg Ile Gly Tyr Gln Pro Met His Glu Glu Glu Val Leu Ala
2360                2365                2370

Val Leu Glu Arg Ala Met Ser Pro Ser Ser Ser Ala Pro Pro
2375                2380                2385

Ser Ser Asn Pro Thr Ile Pro Ala Ser Pro Ala Val Ile Val Thr
2390                2395                2400

Gly Ile Asn Thr Gly Pro Gly Pro His Phe Thr Asn Ala Asp Trp
2405                2410                2415

Met Gln Glu Ala Arg Phe Ala Gly Ile Lys Tyr Arg Asp Pro Leu
2420                2425                2430

Lys Asp Asp Arg Gly Gly Ala Leu Ser Ser Ser Gln Pro Ala Asp
2435                2440                2445

Glu Asp Ser Val Arg Ala Arg Leu Ser Arg Ala Ser Thr Glu Glu
2450                2455                2460

Glu Ala Thr Ala Leu Val Val Gln Val Met Gly His Arg Leu Val
2465                2470                2475

Thr Met Phe Gly Leu Thr Glu Ser Glu Met Ser Ala Thr Gln Thr
2480                2485                2490

Leu Ser Ser Val Gly Val Asp Ser Leu Val Ala Ile Glu Leu Arg
2495                2500                2505

Asn Trp Ile Thr Ala Gln Leu Asn Val Asp Ile Ser Val Phe Glu
2510                2515                2520

Leu Met Glu Gly Arg Thr Ile Ala Glu Val Ala Glu Val Val Val
2525                2530                2535

Lys Lys Tyr Gly Val Gly Ser Lys Val
2540                2545

<210> SEQ ID NO 13
<211> LENGTH: 524
<212> TYPE: PRT
<213> ORGANISM: Monascus BCRC 38072

<400> SEQUENCE: 13

Met Thr Val Pro Thr Asp Thr Val Ser Arg Arg Leu Gln Ser Leu Ala
1               5                   10                  15

Trp Ser Asp Ile Lys Gln His Ala Pro Trp Leu Pro Ser Ser Arg Thr
                20                  25                  30

Leu Val Ser Gly Phe Leu Cys Leu Ile Leu Gln Ile Leu Tyr Ser
            35                  40                  45
```

-continued

```
Arg Gly Arg Lys Ser Asp Leu Arg Val Tyr Asn Pro Lys Lys Trp Trp
     50                  55                  60

Glu Leu Thr Thr Met Arg Ala Lys Arg Glu Phe Asp Ala Asn Ala Pro
 65                  70                  75                  80

Ala Trp Ile Glu Ala Trp Phe Ser Lys Asn Asp Gln Pro Leu Arg Phe
                 85                  90                  95

Ile Val Asp Ser Gly Tyr Cys Thr Ile Leu Pro Ser Ser Met Ala Asp
                100                 105                 110

Glu Phe Arg Lys Met Lys Glu Leu Cys Met Tyr Lys Phe Leu Gly Thr
                115                 120                 125

Asp Phe His Ser His Leu Pro Gly Phe Asp Gly Phe Lys Glu Val Thr
                130                 135                 140

Arg Asp Ala His Leu Ile Thr Lys Val Val Met Asn Gln Phe Gln Thr
145                 150                 155                 160

Gln Ala Ala Lys Tyr Thr Lys Pro Leu Ala Asp Glu Ala Ser Ala Thr
                165                 170                 175

Ile Ala Asp Ile Phe Gly Asp Asn Lys Glu Trp His Thr Ala Pro Val
                180                 185                 190

Tyr Asn Glu Cys Leu Asp Leu Val Thr Arg Thr Val Thr Phe Ile Met
                195                 200                 205

Val Gly Asp Lys Leu Ala His Asn Glu Glu Trp Leu Asp Ile Ala Lys
                210                 215                 220

His His Ala Val Thr Met Ala Ile Gln Ala Arg Gln Leu Arg Leu Trp
225                 230                 235                 240

Pro Val Ile Leu Arg Pro Ile Val His Trp Leu Glu Pro Gln Gly Ala
                245                 250                 255

Lys Leu Arg Ala Gln Val Arg Arg Ala Arg Gln Leu Leu Glu Pro Ile
                260                 265                 270

Ile Gln Glu Arg Arg Ala Glu Lys Ala Lys Cys Leu Ala Gln Gly Ile
                275                 280                 285

Glu Pro Pro Arg Tyr Val Asp Ser Ile Gln Trp Phe Glu Asp Thr Ala
                290                 295                 300

Lys Gly Gln Trp Tyr Asp Ala Ala Gly Ala Gln Leu Ala Met Asp Phe
305                 310                 315                 320

Ala Gly Ile Tyr Gly Thr Ser Asp Leu Met Ile Gly Gly Leu Val Asp
                325                 330                 335

Ile Val Arg His Pro His Leu Ile Glu Pro Leu Arg Asn Glu Ile Arg
                340                 345                 350

Thr Val Ile Gly Glu Glu Gly Trp Thr Pro Ala Ser Leu Tyr Lys Leu
                355                 360                 365

Lys Leu Leu Asp Ser Cys Leu Lys Glu Ser Gln Arg Val Lys Pro Val
                370                 375                 380

Glu Cys Ala Thr Met Arg Ser Tyr Ala Leu Gln Asn Val Thr Phe Ser
385                 390                 395                 400

Asn Gly Thr Phe Val Pro Lys Gly Glu Leu Val Ala Val Ala Ala Asp
                405                 410                 415

Arg Met Ser Asn Pro Glu Val Trp Pro Glu Pro Lys Lys Tyr Asp Pro
                420                 425                 430

Tyr Arg Tyr Met Arg Leu Arg Glu Asp Pro Asp Lys Ala Phe Ser Ala
                435                 440                 445

Gln Leu Glu Asn Thr Asn Gly Asn His Ile Gly Phe Gly Trp His Pro
                450                 455                 460
```

Arg Ala Cys Pro Gly Arg Phe Phe Ala Ser Lys Glu Ile Lys Ile Met
465                 470                 475                 480

Leu Ala Phe Leu Leu Ile Arg Tyr Asp Trp Lys Leu Val Pro Asn Glu
            485                 490                 495

Pro Leu Gln Tyr Tyr Arg His Ser Phe Ser Val Arg Ile His Pro Ala
        500                 505                 510

Thr Lys Leu Met Met Arg Arg Asp Glu Asp Leu
    515                 520

<210> SEQ ID NO 14
<211> LENGTH: 263
<212> TYPE: PRT
<213> ORGANISM: Monascus BCRC 38072

<400> SEQUENCE: 14

Met Arg Ile Gln Arg Thr Pro Ala Pro Pro Lys Ala Pro Arg Ala Leu
1               5                   10                  15

Leu Cys Val His Gly Ala Gly Cys Ser Pro Ala Ile Phe Arg Val Gln
            20                  25                  30

Leu Ser Lys Leu Arg Ala Ala Leu Arg Glu Asp Phe Glu Phe Val Tyr
        35                  40                  45

Ala Thr Ala Pro Phe Pro Ser Ala Pro Gly Pro Gly Ile Leu Pro Thr
    50                  55                  60

Phe Glu Gly Leu Gly Pro Tyr Tyr Thr Trp Phe Glu Gly Ser Pro Ser
65                  70                  75                  80

Gly Ala Ala Ala Lys Gly Asp Asn Ser Asn Ser Asn Asp Ser Asn Ser
                85                  90                  95

Ser Pro Thr Val His Asp Arg Leu Ala Ala Val His Glu Pro Val Arg
            100                 105                 110

Arg Ala Ile Ala Glu Trp Gln Thr Gln Asn Pro Ser Ile Pro Ile Val
        115                 120                 125

Gly Thr Val Ser Phe Ser Glu Gly Ala Leu Val Thr Ala Leu Leu Leu
    130                 135                 140

Trp Gln Gln Gln Met Gly Arg Ile Pro Trp Leu Pro Val Met Gln Val
145                 150                 155                 160

Ala Met Phe Ile Cys Cys Trp Tyr Gln His Glu Ala Thr Gln Tyr Met
                165                 170                 175

Arg Glu Glu Val Gly Cys Gly Gly Asp Gly Gly Ile Asp Gly Glu Lys
            180                 185                 190

Leu Val Ile Arg Gly Val Leu Ser Leu His Leu Gln Gly Arg Asp Asp
        195                 200                 205

Phe Ala Leu Ala Gly Ser Lys Met Val Val Ala Gln His Phe Val Pro
    210                 215                 220

Gly Glu Ala Gln Val Leu Glu Phe Ala Gly Arg His His Phe Pro Asn
225                 230                 235                 240

Arg Pro Arg Asp Val Leu Glu Thr Val Lys Arg Phe Arg Gln Leu Cys
                245                 250                 255

Val Arg Ala Arg Val Ile Gly
            260

<210> SEQ ID NO 15
<211> LENGTH: 360
<212> TYPE: PRT
<213> ORGANISM: Monascus BCRC 38072

<400> SEQUENCE: 15

```
Met Thr Ile Thr Phe Thr Leu Pro Pro His Gln Thr Ala Leu Thr Val
1               5                   10                  15

Asp Glu His Asp Lys Val Thr Ile Trp Asp Val Ala Pro Cys Pro Ser
            20                  25                  30

Leu Pro Pro Asp Gln Val Cys Val Arg Val Glu Ala Val Ala Leu Asn
        35                  40                  45

Pro Ser Asp Thr Lys Met Arg Gly Gln Phe Ala Thr Pro Tyr Ala Phe
    50                  55                  60

Leu Gly Thr Asp Tyr Ala Gly Thr Val Val Ala Val Gly Ser Gln Val
65                  70                  75                  80

Thr His Ile Gln Val Gly Asp Arg Val Tyr Gly Ala Gln Asn Glu Met
                85                  90                  95

Cys Pro Arg Thr Pro Arg Pro Gly Pro Phe Ser Gln Tyr Thr Val Thr
            100                 105                 110

Arg Gly Arg Ile Trp Ala Thr Val Pro Glu Gly Trp Ser Phe Glu Gln
        115                 120                 125

Ala Ala Ser Leu Pro Ala Gly Ile Ser Thr Ala Gly Leu Ala Met Lys
    130                 135                 140

Leu Leu Gly Leu Pro Leu Pro Asp Pro Asn Ala Thr Thr Ala Pro Ala
145                 150                 155                 160

Leu Pro Lys Pro Val Tyr Val Leu Val Tyr Gly Gly Ser Thr Ala Thr
                165                 170                 175

Ala Thr Ile Val Met Gln Met Leu Arg Leu Ser Gly Tyr Ile Pro Ile
            180                 185                 190

Ala Thr Cys Ser Pro His Asn Phe Asp Leu Ala Lys Lys His Gly Ala
        195                 200                 205

Glu Asp Val Phe Asp Tyr Arg Asp Ala Gly Leu Ala Gln Thr Ile Arg
    210                 215                 220

Thr Tyr Thr Lys Asn Asn Leu Arg Tyr Ala Leu Asp Cys Ile Thr Asn
225                 230                 235                 240

Val Glu Ser Thr Thr Leu Cys Phe Ala Ala Ile Gly Arg Ala Gly Gly
                245                 250                 255

Arg Tyr Val Ser Leu Asn Pro Phe Pro Glu His Ala Ala Thr Arg Lys
            260                 265                 270

Met Val Thr Ala Asp Trp Thr Leu Gly Pro Thr Ile Phe Gly Glu Gly
        275                 280                 285

Ser Thr Trp Pro Ala Pro Tyr Gly Arg Pro Gly Ser Glu Lys Asp Arg
    290                 295                 300

Ala Phe Gly Glu Glu Leu Trp Arg Val Ala Ala Arg Leu Val Glu Asp
305                 310                 315                 320

Gly Lys Ile Val His His Pro Leu Arg Val Ile Pro Gly Gly Phe Glu
                325                 330                 335

Ala Ile Lys Gln Gly Met Glu Leu Val Arg Thr Gly Gln Leu Ser Gly
            340                 345                 350

Glu Lys Val Val Val Lys Leu Gly
        355                 360

<210> SEQ ID NO 16
<211> LENGTH: 413
<212> TYPE: PRT
<213> ORGANISM: Monascus BCRC 38072

<400> SEQUENCE: 16

Met Arg Gln Phe Leu Ser Ser Asp Arg Ile Asn Ser Glu Ile Pro Gln
1               5                   10                  15
```

```
Glu Lys Ser Glu Met Val Gly Phe Ser Asp Ile Asp Asn Ser Ser Arg
             20                  25                  30

Gln Ile Lys Glu Met Glu Ala Ala Phe Arg Ser Ala Val Lys Thr Gly
             35                  40                  45

Gln Ile Pro Gly Ala Val Ile Met Ala Arg Asp His Ser Gly Arg Leu
         50                  55                  60

Asn Tyr Thr Arg Cys Phe Gly Ala Arg Thr Val Val Arg Asp Glu Cys
 65                  70                  75                  80

Asn Arg Leu Pro Pro Met Gln Val Asp Thr Pro Cys Arg Leu Ala Ser
                 85                  90                  95

Ala Thr Lys Leu Leu Thr Thr Ile Met Ala Leu Gln Cys Val Glu Arg
            100                 105                 110

Gly Leu Val Arg Leu Asp Glu Thr Val Asp Arg Leu Leu Pro Asp Leu
            115                 120                 125

Ser Ala Met Lys Val Leu Glu Gly Phe Asp Ala Ala Gly Glu Pro Lys
        130                 135                 140

Met Arg Glu Arg Lys Gly Lys Ile Thr Leu Lys His Leu Leu Thr His
145                 150                 155                 160

Thr Ser Gly Leu Ser Tyr Val Phe Leu His Pro Leu Leu Arg Glu Tyr
                165                 170                 175

Met Ala Lys Gly His Leu Gln Thr Ala Glu Lys Phe Gly Ile Gln Ser
            180                 185                 190

Arg Leu Ala Pro Pro Ala Val Asn Asp Pro Gly Ala Glu Trp Ile Tyr
        195                 200                 205

Gly Ala Asn Leu Asp Trp Thr Gly Lys Leu Val Glu Arg Ala Thr Gly
    210                 215                 220

Leu Asp Leu Glu Gln Tyr Leu Gln Glu Asn Ile Cys Ala Pro Leu Asn
225                 230                 235                 240

Ile Thr Asp Met Thr Phe Lys Leu Gln Gln Arg Pro Asp Leu Leu Ala
                245                 250                 255

Arg Arg Ala Asp Gln Thr His Arg Asn Lys Ala Asp Gly Arg Leu Arg
            260                 265                 270

Tyr Asp Asp Ser Val Tyr Phe Arg Ser Asp Gly Asp Glu Cys Phe Gly
        275                 280                 285

Gly Gln Gly Val Phe Ser Gly Pro Glu Ser Tyr Met Lys Val Val His
    290                 295                 300

Ser Leu Leu Gln Arg Asp Gly Arg Leu Leu Arg Pro Glu Thr Val Asp
305                 310                 315                 320

Leu Met Phe Gln Pro Ala Leu Asp Ala Gln Thr Glu Lys Gln Met Asn
                325                 330                 335

Gln His Met Asp Ala Ser Pro His Ile Asn Tyr Gly Gly Pro Met Pro
            340                 345                 350

Met Val Leu Arg Arg Ser Phe Gly Leu Gly Gly Met Ile Ala Leu Glu
        355                 360                 365

Asp Leu Asp Gly Gln Lys Trp Arg Arg Lys Gly Cys Leu Thr Phe Gly
    370                 375                 380

Gly Gly Pro Asn Ile Val Trp Val Met Leu Leu Ser Ala Leu Arg Phe
385                 390                 395                 400

Val Phe Phe Phe Phe Phe Phe Phe Phe Cys Ser Ser
                405                 410

<210> SEQ ID NO 17
<211> LENGTH: 455
```

```
<212> TYPE: PRT
<213> ORGANISM: Monascus BCRC 38072

<400> SEQUENCE: 17

Met Ala Leu Ser Pro Val Gln Asp Pro Ser His Thr Asp Lys Thr
1               5                   10                  15

Met Pro Arg Arg Ala Phe Arg Arg Ser Cys Asp Arg Cys His Ala Gln
            20                  25                  30

Lys Ile Lys Cys Ile Gly Ser Glu Gly Ala Val Ala Arg Ala Ser Cys
        35                  40                  45

Gln Arg Cys Gln Gln Ala Gly Leu Arg Cys Val Tyr Ser Glu Arg Cys
    50                  55                  60

Pro Lys Arg Lys Leu Pro Lys Pro Asn Pro Ala Glu Ser Ser Pro Ala
65                  70                  75                  80

Ser Ser Thr Ala Gly Leu His Thr Ser Ser Asp Ser Ser Pro Pro
                85                  90                  95

Val Pro Ser Asp Gly Leu Pro Leu Asp Leu Pro Gly Pro Asp Ser Ser
                100                 105                 110

Gly Val Ser Leu Gln Phe Leu Asp Pro Ser Ala Asp Cys Asp Trp Pro
            115                 120                 125

Trp Ser Ser Ile Gly Val Asp Glu Thr Val Val Asn Asn Cys Leu Asp
        130                 135                 140

Leu Ser His Gly His Gly His Gly Asp Leu Ser Cys Gln Leu Glu Leu
145                 150                 155                 160

Pro Met Pro Asp Leu Pro Ser Pro Phe Glu Phe Ser Ala Glu Lys Ser
                165                 170                 175

Pro Ser Pro Ser Val Ser Gly Ser Ile Ala Gly Ala Val Ser Ala Gln
            180                 185                 190

Arg Glu Leu Phe Asp Gly Leu Ser Thr Val Ser Gln Glu Leu Glu Ala
        195                 200                 205

Ile Leu Leu Ala Val Ala Val Glu Trp Pro Lys Gln Glu Ile Trp Thr
210                 215                 220

Tyr Pro Ile Gly Thr Phe Phe Asn Ala Ser Arg Arg Leu Leu Val Tyr
225                 230                 235                 240

Leu Gln Gln Gln Ser Asn Thr Arg Ser Asp Gln Gly Met Leu Asn Glu
                245                 250                 255

Cys Leu Arg Thr Lys Asn Leu Phe Met Ala Val His Cys Tyr Met Leu
            260                 265                 270

Ile Val Lys Ile Phe Thr Ser Leu Ser Glu Leu Leu Ser Gln Ile
        275                 280                 285

Arg His Ser Gln Ala Gly Gln Leu Thr Pro Leu Glu Gly His Gln Phe
    290                 295                 300

Glu Pro Pro Pro Ser Ser Ser Arg Asp Arg Ser Ser Val Asp Thr Met
305                 310                 315                 320

Pro Ile Phe Asn Pro Asn Leu His Ile Gly Leu Phe Ser Tyr Leu
                325                 330                 335

Asn Pro Phe Met His Ala Leu Ser Ser Ala Cys Thr Thr Leu Arg Val
            340                 345                 350

Gly Val Gln Leu Leu Arg Glu Asn Glu Ser Ala Leu Gly Ile Pro Pro
        355                 360                 365

Ala Gln Gly Val Ala Ala Ser Val Ser Met Gly Lys Glu Glu Trp Ala
    370                 375                 380

Asp Gly Glu Asp Val Ala Ser Ala Val Thr Thr Ala Asp Glu Asp Leu
385                 390                 395                 400
```

-continued

Arg Gln Pro Ala Ser Arg Ile Leu Ser Met Val Trp Ser Asp Glu Val
                405                 410                 415

Gly Asp Gln Lys Ala Lys Ser Ala Asp Ala Ala Gly Pro Arg Ser Arg
            420                 425                 430

Thr Leu Ala Val Leu Arg Arg Cys Asn Arg Glu Ile Phe Ser Leu Ala
        435                 440                 445

Arg Gln His Asn Leu Ala Ser
    450                 455

<210> SEQ ID NO 18
<211> LENGTH: 543
<212> TYPE: PRT
<213> ORGANISM: Monascus BCRC 38072

<400> SEQUENCE: 18

Met Ala Ser His Gln Ser Glu Lys Glu Lys Pro Gln Ser Cys Thr Thr
1               5                   10                  15

Glu Val Gln Val Ser His Val Thr Gly Leu Lys Leu Gly Leu Val Val
            20                  25                  30

Thr Ser Val Thr Leu Val Val Phe Leu Met Leu Leu Asp Met Ser Ile
        35                  40                  45

Ile Val Thr Ala Ile Pro His Ile Thr Ala Gln Phe His Ser Leu Gly
    50                  55                  60

Asp Val Gly Trp Tyr Gly Ser Ala Tyr Leu Leu Ser Ser Cys Ala Leu
65                  70                  75                  80

Gln Pro Leu Ala Gly Lys Leu Tyr Thr Leu Thr Leu Lys Tyr Thr
                85                  90                  95

Phe Leu Ala Phe Leu Gly Val Phe Glu Val Gly Ser Ala Leu Cys Gly
                100                 105                 110

Ala Ala Arg Cys Ser Thr Met Leu Ile Val Gly Arg Ala Val Ala Gly
            115                 120                 125

Met Gly Gly Ser Gly Leu Thr Asn Gly Ala Ile Thr Ile Leu Ala Ser
130                 135                 140

Ala Ala Pro Lys Gln Gln Pro Leu Leu Ile Gly Ile Met Met Gly
145                 150                 155                 160

Leu Ser Gln Ile Ala Ile Val Cys Gly Pro Leu Leu Gly Gly Ala Phe
                165                 170                 175

Thr Gln His Ala Ser Trp Arg Trp Cys Phe Tyr Ile Asn Leu Pro Val
            180                 185                 190

Gly Ala Leu Ala Ala Ile Leu Leu Leu Ala Ile His Ile Pro Lys Ser
        195                 200                 205

Val Pro Thr Ser Asp Cys Thr Met Pro Ala Pro Arg Ala Val Gly Val
    210                 215                 220

Arg Val Ile Leu Ser Gln Leu Asp Leu Leu Gly Phe Val Leu Phe Ala
225                 230                 235                 240

Ala Phe Ala Val Met Ile Ser Leu Ala Leu Glu Trp Gly Gly Ser Asp
                245                 250                 255

Tyr Met Trp Asp Ser Ser Val Ile Ile Gly Leu Phe Cys Gly Ala Gly
            260                 265                 270

Ile Ser Leu Val Val Phe Gly Phe Trp Glu Arg Tyr Val Gly Asn Ser
        275                 280                 285

Met Ala Met Ile Pro Phe Ser Val Ala Ser Arg Arg Gln Val Trp Cys
    290                 295                 300

Ser Cys Leu Phe Leu Gly Phe Phe Ser Gly Ala Leu Leu Thr Phe Ser

|     |     |     |     | 305 |     |     |     |     | 310 |     |     |     |     | 315 |     |     |     |     | 320 |
| --- | --- | --- | --- | --- | --- | --- | --- | --- | --- | --- | --- | --- | --- | --- | --- | --- | --- | --- | --- |

Tyr Tyr Leu Pro Ile Tyr Phe Gln Ala Val Lys Asp Val Ser Pro Thr
              325                      330                     335

Met Ser Gly Val Tyr Met Leu Pro Gly Ile Gly Gln Ile Val Met
        340                      345                      350

Ala Ile Val Ser Gly Ala Ile Ile Gly Lys Thr Gly Tyr Tyr Ile Pro
            355                      360                365

Trp Ala Leu Ala Ser Gly Ile Ile Val Ser Ile Ser Ala Gly Leu Val
    370                      375                    380

Ser Thr Phe Gln Pro His Thr Ser Ile Ala Ala Trp Val Met Tyr Gln
385                      390                    395                400

Phe Met Gly Gly Phe Gly Arg Gly Cys Gly Met Gln Thr Pro Ile Ile
            405                      410                415

Ala Ile Gln His Ala Leu Pro Pro Gln Met Ser Ala Leu Gly Ile Ser
              420                      425                430

Leu Ala Met Phe Gly Gln Thr Phe Gly Gly Ser Leu Phe Leu Thr Leu
        435                      440                    445

Ala Lys Leu Val Phe Ser Ala Gly Leu Asp Ala Gly Leu Arg Glu Tyr
450                      455                    460

Ala Pro Ala Val Ser Ala Glu Ala Val Thr Ala Ala Gly Ala Thr Gly
465                      470                    475                480

Phe Arg Asp Val Val Pro Ala Asn Leu Leu Ser Gln Val Leu Leu Ala
            485                      490                495

Tyr Cys Lys Gly Ile Asp His Thr Phe Tyr Leu Ala Val Gly Ala Ser
              500                      505                510

Gly Ala Thr Phe Leu Phe Ala Trp Gly Met Gly Gln Val Gly Leu Ile
        515                      520                    525

Trp Trp Gly Glu Glu Arg Thr Gly Phe Gly Arg Asp Glu Arg Val
    530                      535                    540

<210> SEQ ID NO 19
<211> LENGTH: 9228
<212> TYPE: DNA
<213> ORGANISM: Monascus BCRC 38072

<400> SEQUENCE: 19

```
atgtacgtag gacgcattgg tgcgaccaca tacatctctc gtcccgcaga ctctcgagct      60
acgccaaaag tgatcaaaac tcaagggtcg atcaccacgt ctaatctaac atcactaaca     120
accatggctc agtcaacata ccccaatgag cctattgtcg tggtaggaag cggctgccgc     180
tttcccgggg cgccaacac gccctccaag ctgtgggagc tccttcggga gcctcgcgac     240
gtccgtagca aaatcccgaa agagagattt gacgtcgacg cattctatca tccagacgga     300
aaacaccatg gacgaacaaa cgcaccctat gcctatatgc tacaagaaga cctgcgcgcc     360
ttcgacggcc ctttcttcaa tatccaggcc ggagaggccg agagtatgga tccacaacag     420
cggctcttgc tggagaccgt gtacgaggca gtctcagatg ccggtatgcg atccaagac     480 ctgcagggt cttccactgc cgtttatgtt ggcatgatga cacgactac gagacggtg     540 tcgacgcgcg acttggagag cattcccact tactcggcca cgggagtcgc tgttagtgtc     600
gcgtcgaacc gcatctcata ctttctttgac tggcatggcc cgagtatgac gatcgatacc     660
gcatgcagct cgtctttggt tgccgttcac ctggctgtac aacagctacg cagtgggcaa     720
agctccatgg ctatcgccgc gggcgccaac atgatcctcg ggcccatgac cttcgttcta     780
gaaagcaagt tgaacatgtt atcccccctcg ggccggtccc gcatgtggga cgctgggcc     840
```

```
gatggctatg ctagaggcga agctgtttgt tcggtagtgc ttaaaacatt gagccaagcc      900
ttgcgcgatg gcgacagcat tgaatgcgtt atccgagaaa ccggtgtgaa ccaagatggt      960
cgaacgacag gcatcacgat gcccaaccac agcgctcagg aggcacttat cagggctacc     1020
tactccaaag ccggcctcga catcacgaac cccgaggatc gatgccagtt cttcgaggct     1080
catgaaactg gtacaccagc aggagatcca caggaggccg aggccatcgc aaccgccttt     1140
ttcggacaca aaaggaggc ctccgatgct gagaacgcag agactcccct cttcgtgggc      1200
agtgtgaaga ccgttgtcgg tcatactgag ggcactgccg gcctggctgg tctcatgaag     1260
gcgtccttcg ccgtccagca cggagtgatc ccgcccaacc tgctgtttga gaatatcagc     1320
ccccgcgtgg ccccattcta ctccaatttg aagattgcaa cagagacaac accatggccc     1380
accatcaaac ctggacagcc tcgccgtgtc agtgtcaact cttttggttt cggtggcacg     1440
aatgcacatg caattattga ggaatacata aagtctgacc aaaaggtgcc agcgagccga     1500
cagccggtgg agtactcaga cagtcccagt acattgaatc tgcccttggt tctctcggcc     1560
aagtctcagc gctccatgaa gacaacgttg gagagcatgg tacagttcct tcagtccaac     1620
cctgaagtta acttgcggga tctttcatgg actctactgc ggaagcggtc gattctaccc     1680
ttccgtcggg ctattgtcgg ccatagccac gaagcaatcc gtgccgctct cgaggcagcc     1740
attgaagacg gcatcgttgt gagcgacttc agcgcggatg tcaaaggcaa gccgtctgtg     1800
ctggagtct tcaccggaca gggtgcccaa tggcctggga tgttgaagga actgattgtg      1860
ggatcatcct atgtgcggtc gatagcgag gagctggatc actcactgca gactttgccg      1920
gagaagtacc gccccctg gaccattctc gagcagctaa tgctagaaga tgaggcttcc       1980
aacgtccgac acgccagctt ctcccagccc ctatgctgtg ctgttcagat tgttctggtg     2040
cgtctcctga agcagcagg aatccagttt gctgctgtgg tcggacacag ttccggagag      2100
atcgcctgtg catttgccac cggtcttatc agtgcatcct tggcaattcg tattgcccac     2160
ctgcgtggag tcgtttcggc ggagcacgct gcctccgcga gcggaggacg cggatctatg     2220
ttggcagcag gtatgtccta tgaggaagcg aaagagctct gtgagttgga tgcctttgaa     2280
agccgcatct gtgttgctgc tagcaattcc ccagacagcg ttaccttctc gggagatgcg     2340
gatgcaattg agcacttgca gggcgttctg gaggacgagg ctacgttcgc cagactgctc     2400
agggtggata cagcatacca ctctcaccat atgcttcctt gtgcagcgcc gtatatgcaa     2460
gctttggagg aatgcggctg tgctgttgct gatggagacg tcaggtgga agagggatca      2520
tggtattcct ctgtcaagga cagcaacgaa ccaatgggcc ttgccgacgt gactgctgag     2580
tactggaaag ataacctggt atccccggtg cttttctctc aggccgtcca gcgggcagcc     2640
atcatgcacc ggcccctgga tgtcgggatt gaagtcggtt gccaccctgc tctcaagggc     2700
ccgtgtctgg ctaccatcaa ggatgctctg tcggacgttg acctggcata cacaggatgt     2760
ttggagcgcg gaaagaatga tatgaatgca ttttcccagg ccctggccta tctttgggag     2820
cagttcggaa ttcaagcct ggatgctgac cgctttataa gtaccattgc tcccgagcgc      2880
tcctgcgtga gcctttcgaa gcagctgccg acgtactcat gggaccattc tcggagctat     2940
tggacggaat ctcgtgccac tcgtcagcac ctgcgaggac cgaagccgca tcttctgctg     3000
ggtaagctct ctgaatatag cactccgttg accttccagt ggctgaactt tgtccgtcct     3060
cgcgacattg aatggctgga tgggcatgca ttgcagggcc aagtggtctt ccctgccgcg     3120
ggttatattg tcatggcgat ggaggcggcc atggaaattc ccaactctca tcaggtgcaa     3180
```

```
gtccagctac ttgagatcct ggatatgagc attgacaaag cggtggtttt cgatgatgaa    3240
gacagtctgg tagaacttaa cttgaccgcg gaagtaacca gcggcatcgg taaaggtgac    3300
cggatgatcc tcagcttcat aattgattcc tgtctatcca gggaaggtga cctctccacc    3360
tcagccaagg gtcagctagt cgtcacattg gatgaaggcc atctccaggt gaccccagat    3420
aacgagaagc agctcctacc cccgccagaa aagagcatc ctcacatgaa ccgagtgaat    3480
atcaattcat tctaccacga gctggatctg atgggctacg actacagcaa agacttccgg    3540
cgcctgcata gcatgcgacg agccgatgca cgagccagtg gaattttgga atttattcct    3600
ctgaacgacg aggtccacgg ccgtcctctc ctgctgcatc ccgctccctt ggacattgcc    3660
ttccagacag tcatcggcgc atactcctcc cccggagatc gacgtctacg ctgcctgtat    3720
gtgccgacgc acattgatcg cattgctctt gtgccctctc tctgtcttgc gacagctgcg    3780
tccggttgtg acaagattgc cttcaatact atcaacacct atgacaaggg tgatttcctc    3840
agcggtgaca tcgtggcgtt tgacgcggag cagaccagtc tgttccatgt cgagaatatt    3900 gttttaagc ccttctcgcc cccgactgcg tctactgatc atccgatctt cgccaaatgg    3960
agctggggtc cactgacccc ggaaaccctg ctggacaacc caaccattg gccacggcg     4020 caggataagg aagcgatccc catcattgaa cgcattgtct acttttacat caaattgttc    4080
ctgcagcagc tgacccgaga agatcgcgaa caagcggcat tccacctgca gaggcagatt    4140
gtgtggtgtg aacaagtcgt ggccgacgct cacgaaggtc gtcaccaatg gtacgatgca    4200
gcttgggaga atgataccga agcccagata gagcagttat gtgccagaag ctcctaccac    4260
cctcacgttc gcttggtaca gcgagttggt caaaacctgc tcgcaaccat ccgttcgaat    4320
ggcaacccgt tcgatctcat ggaccatgat ggcctgttga ccgagttcta taccaacacg    4380
ctcagttttg gcccagcgtt gcactatgcc caagaccttg tgggtcaaat tgcccatcgc    4440
tatcaatcta tggatatcct ggagatcgga gctggaaccg tggcgccac caaatacgtg     4500 ctggcaacgc ctcaactcgg gttcaacagc tacacgtaca ccgacatctc gaccggcttc    4560
ttcgaaaagg cacgcgaaca gtttgctgcc ttcgaggacc gcatggagtt tgagcccctc    4620
gatatccgcc gcagcccagc agagcaaggt ttcacggagc acgtgtacga cctaatcatc    4680
gcgtccaacg tgctacacgc aacgcccgac ttggagaaga ccatggccca tgcacgctcc    4740
ctgctgaagc ccgggggcca gatggtgatt ctggagatca cccaccggaa ccacaccaga    4800
ctagggttta tcttcggcct gttcgccgat tggtgggcag gtatcgacga tgggcggacc    4860
atggagccat ttgtgtcgtt tgaccgctgg gatgagatct tgaagcacgt cgggttttcc    4920
ggcatcgaca gtcgcaccaa ggaccgcgat gcggatctgt tccccacatc ggtcttcagc    4980
acgcatgccg ttaactcgac aatcgactac ctgcacaagc tcttgacgc tccagtgaag    5040 gactcgtacc ccccgttggt ggtggtcggt ggccagacgc caaagaccca gcgcatcttg    5100
gatgagatca aagccgttat gcctaatcgc cagatccagt acaccagcg tctcgttgat    5160 ttgttggatg cagaggacat gcaggccaag ttcacctttg ttgtcctcac ggagctggac    5220
gaggagctat tcgctggtct caccgaagac agctttgaag cagtcaagct actgctcatg    5280
tacgccggga acatgctgtg gctgaccgag aatgcctggg tcaagcgccc tcatcaggcg    5340
agtaccatcg gaatgctgcg ctccatcaga gcgcagcacc ccgacattgg tgtccatatt    5400
atggatgtcg actctgccga gaacctggac gcacacttcc tggtcgaaca ggtccttcgg    5460
ctggaggagg atatcgacga attggcagcc acgacaacgt ggactcagga gccagaagtc    5520
ttctggtgca atggccgcgc ctggattcct cgtctgaagc atgataaatc gaggaataac    5580
```

```
cgtatgaact cctcacgtcg tcagatcttt gagaccctca atccatccaa gatcccgtt    5640
gcattgaaga aggcggcagc ctcctcttct tactacctgg agtcagctga gacctggccc    5700
gtgccaggtg ccgttactgc aggggatagg aaaacggtcc atgttcggct cagccatccc    5760
cacgcccttc gggttggaca tcttgggttt ttctacctcg ttcagggcca cgtcctgaag    5820
ggtgatcaag cacttcctgt ggtggctttg gctgagcgca acgatcgat tgtccacgtt    5880
cgttcagact atgtccatgt tctagaagat accgcggtgt ctgcgaacaa tggaagtttc    5940
atcttggccg ctgcagcggc cgtgttggcc gagacggtga ttcacagtgc caagagcctg    6000
ggagctgatg cctcggtcct ggtcttgaat gccccgggct tctgtgccca gacattgctc    6060
cgcgctgcaa gagattctgg acttcgggtc catctggcca ccacatcgtc cagtaccgac    6120
ccgtctcctg gggccgaccg ttgcgtccga ctgcatcccc gcgacacgga taggcgcctc    6180
aaacagcttc tgccccgtgg cactcaggca ttcttcgatc tgtccaccga tccgagcagt    6240
gaaggtctca cacagcgatt gccaaacgtc cttatacccc gctgtgttcg gcacagtact    6300
gaatacttgc tcagagatac cgcttccgct ggtgggaaag ctacgctgcc cgcggcatac    6360
tgggagcgtg tagcctcctt ggctaatcac agcctcagta ctcactttaa ggagaatgat    6420
aatgccagca atggatgcca ggtcttgtct tgcacagaca ttgtcgcgcg taataacaag    6480
agccgtctga acgcatcgac tgtcatctcc tggccagatg acgcggccct cccggccaga    6540
atccgtccca tcgataccga gaccctgttt gcagcgaaaa agacgtacct cttagtcgga    6600
ctcactggag atctcggccg gtccttgggc cgctggatgg tcttacacgg tgcccgccgc    6660
atcgtcctca ccagccgcaa cccgcaagtg agcccgaatt gggtggcgca tgttgaagag    6720
ttgggcggcc aggttaccgt tctgtccatg gatgtgacga gcgaagactc ggtggattct    6780
ggcttggcca aactccagga tttgaagttg cccctatcg gcggcattgc ctttggccct    6840
ttggtgctgc aggatgtaat gctgaagaac atggacctgc aaatgatgga gatggtgctg    6900
aaacccaagg tcgagggagc ccgcatcctg cacgagaagt tctccgaccc tgccagcagc    6960
aacccactcg acttcttcgt catgttctcc tcgattgtag cggtaatggg taacccgggc    7020
caggccaact acagcgcggc aaactgctac ctgcaggctt tggcgcagcg gcgatgcgcc    7080
tctggattgg cggcttcgac tatcgacatc ggtgcagtct atggtgtcgg ttcgtgacc     7140
cgggcggaac tggaggagga tttcaatgct attcggttca tgtttgactc ggtcgaagaa    7200
catgagctgc actctctgtt tgccgaggcg gtggtgtccg gtcgacgggc catgcaccag    7260
cagcagcagt tcaagacggt gctcgacatg gccgatatcg aattgacgac cggtataccc    7320
ccgctggatc cgactctcaa ggatcgcatt acgttcttcg acgacgctcg ggtcggtaac    7380
ttcaagattc ccgaacggcg cggcaaggcg ggcgataacg cagcaggatc caagggctct    7440
gtcaaggaac agctcttgca agctacaagc ttggaccagg tccgtcaaat agtcattgat    7500
ggtctatccg aaaagcttcg ggtgacccct cagattcccg atggggagag cgtgcacccc    7560
actatcccgc tcatcgacca gggagtagac tccctgggcg cggttaccgt gggtacctgg    7620
ttctcgaagc agctgtacct agacctgccg cttctcagag tgcttggagg cgcctccgtg    7680
gccgatctgg cggacgacgc tgctgcccgg ctgccgccca gctccattcc actcgtggca    7740
gcaagcgaag ggggcgcgga gacctcggac aatgacactt cagggcctga ggggactgat    7800
ctcagcgcct cgaccacaat caccgagccc tcatctgcag acgaagagga cgaaaagcag    7860
gaggacgaca acgacaactc cgtcctcgcc cttcatccac tctccctcgg ccaggagtac    7920
```

```
gcttggagac tgcaaaaggc cgccgatgat tcgaccatct tcaacaacac gatcggcatg    7980
ttcatgacgg gctccatcga cgccaaacgg ctgtccaagg ctctccgagc ggtcttgcgc    8040
cggcacgaaa tcttccgcac cggctttgcg gctgtcggta acaatgcaga tgccacgagt    8100
ctagcgcaaa ttgtctttgg tcgaaccaag aacaaggtcc aagtcatcca ggtggctgac    8160
cgggccggcg cggaagaagg ctaccggcag ctggtgcaga cacagtacga catcaccgct    8220
ggagacactc tgagactggt cgacttcttc tggggcaagg acgagcatct gttcgttgtg    8280
gcctaccatc gatttgtcgg cgatggttcc accacggaga atatctttgt cgaagcgagc    8340
cagttatacg gcggcgtgac cctcgacaag cacgtccctc aatttgcaga cctcgcgacg    8400
cggcagcgag aagcgctcga gtccggccag atggatgcgg acctcgcgta ctgggaatcg    8460
atgcaccacc agcccacggg cgtggtgtcc ccggtcctcc cgcggatgct tctgggcgaa    8520
gatggcctta atagcccgaa ccacgcccgc cagcccaact cgtggaagca acacgaagcg    8580
atcgcgcgtc tcgaccccat ggtcgctttc cgcatccgcg agcgcagtcg caagcacaaa    8640
gccacgccca tgcaattcta cctggctgcg taccacgtgc tcctggcacg attgacgggc    8700
agcagcgact tcagcatagg cctggccgac accaatcgca cgaacgtgga tgaactggcg    8760
ggcatgggct ttttcgccaa cctgctcccg ctgcgcttcc gcaacttcgt cccgcacatc    8820
acctttggcg agcacctggt cgccaccaag gacaaggtgc gcgaggccat gcagcacgcc    8880
cgcgtgccct acggggtgct gctcgagcgc ctcggattcg aggtcccggg ggccaccgcc    8940
gaaacagcgg aaccggcccc cttgttccaa gcggtcttcg attacaagca gggccaggcg    9000
gagagtggtt cgattggcag cgccaagatg accgaggtca tcgcgactcg cgaacgcacc    9060
ccctacgatg tcgtgctgga gatgtcggat gatcccacca aggatccgct gctcaccgtc    9120
aagttgcaga gctcggtgta cgaggtgcat catcccaggg cgttcttgga gagttatatc    9180
tccatattgt cgatgttttc gatgaatccc gcgttgaagt tggcttga              9228
```

<210> SEQ ID NO 20
<211> LENGTH: 7644
<212> TYPE: DNA
<213> ORGANISM: Monascus BCRC 38072

<400> SEQUENCE: 20

```
atgaaagcga cggcagcctc gggcacacct actcccatag ctgtagtggg catgggatgc      60
agatttgccg ggggagcaac agatccacag gcactgtgga aattgctgga gcaaggaggg     120
agcacttggt ccaagactcc atcctcgaga ttcaacgtca gcggagtcta ccaccctaac     180
ggccaacgag taggatcgat gcacgttcgg ggtggtcatt ttctagacca agacccggct     240
cttttcgatg cctcattttt caatatgacc agtgaagttg ccagttgtat ggaccccaa      300
cagagactca tactcgaagt cgtctatgaa gcgctagagg ccgcgggaat tccccttgaa     360
agtgtggccg gctcgaatac cgcggtcttt agcggagcaa tgtatcacga ctaccaggat     420
tcgctccatc gcaacccgga aactctgccg cgatacttca tcacgggtaa tgctggcacg     480
atgatgtcga gtcgcgtctc ccacttctat gacctccgcg gtcccagcgt cacagttgac     540
actgcatgtt ccaccacctt gactgccttg cacctcgcaa tccaaagcat acgagcggga     600
gaggctgaca tggccattgt ggccgggtcg aatctgctct tgaactcgga tgttttttgtc     660
accatgtcca atttaggctt tctctccccg gatgggattt cctactcatt tgatccgaga     720
gctaatgggt atggacgtgg agaaggggta gccgccatca tcttgaaggc tctccccgc      780
gcgctgcgag acgggacccc aattcgcctt gttgtccgcg agacggcgct caaccaagac     840
```

```
ggtcggaccc ccgccatcac cgggccgagc cccgaagcgc aggcgtgcct gatccgggaa    900
tgctatcaga aggccggtct ggacccgagg cagacatcgt acgtggaagc acatggaaca    960
ggaactccga caggtgatcc gctggagctg gcggccatct cagctgcatt ccaaggccag   1020
cctctgcaga tcggctccgt aaaagccaac ctcgggcaca ccgaagctgc cagcgggctg   1080
gcaagcgtaa tgaaggtggc tctggcactg gaaaaaggga ttgtgccacc tagtgcaaga   1140
ttcctgcagc cgagcaagaa gttgctggaa gagagaaaat ccagattcc cctatctagc    1200
caattgtggc ttccgattga cggaatttgt cgcgcatcga tcaacaactt cggcttcgga   1260
ggcgcgaatg ctcatgcaat cgtggagcgg tatgaccccg ctgcgagaat atcgacgagc   1320
aagccaaacg gtcatatccg gcctcacgac agccatgtgg aagcagatcg agggaaaatc   1380
tatgttttga gtgccaagga cgagcacagt tgccaggaaa tgatttcaag gttgcgcgac   1440
tacctcaacc gcgctaatcc gactgatgaa cggcaattcc tcgctaacat ggcgtacact   1500
ttagcttctc gtcgctcgaa tctccgatgg aaggcagcct gcagggcaca tagcctggcg   1560
agccttctct ctgttctcgt aagcgatggg acgcgacctc ggagatcggc cgagaaagcg   1620
aggctgggat gggtcttcac tggccaagga gcacaatggt ttgcaatggg ccgcgagtta   1680
atcgaggcgt atcccgtttt caaggaggca ctcatcgagt gcgatggcta tatcaagggc   1740
atgggagcga actggtccat tatagatgaa cttcgtcgcg gtgaagcaga aagtcgcgtg   1800
aacgaggcag aatttagcct accgttgtca acggctatcc aggttgcact cgttcgtcta   1860
ctctggtcgt gggggatccg accagcggca attaccagcc actctagcgg agaggtagct   1920
gcagcttacg ctgtcggggc attttcagcc cgatcagcca ttggaatcag ctatatacgt   1980
ggtgccttga tagcaaaaac ccagccggca ccgacaacga aggggggcat gctagctgtg   2040
ggattgagtc gcagtgaggt tggtgaatac ataacacgag tacaacaaca aggcgaggaa   2100
tacttggttg taggatgcat aaacagcccc tccaacgtga cggtatcagg agatttgtct   2160
gcggttgtca gattggagga gttgttgcat gctgaccaaa tatttgcgag acgactcaag   2220
gtcacccagg cgtttcactc ccaccacatg caacctttgt caggtgaatt tcgggaggct   2280
ctggtagagg tcttcaatgc agacatcact gacaccacta atgcctgcca ggatgtggtt   2340
tacgcatccc ccaaaaccgg gaaacgccta gacgattgta accacctgcg cgatcccatg   2400
cactgggtgg aaagtatgct ttttccggtc gaattcgaat cttcattccg tgaaatgtgc   2460
ttcgacagga aagatcaagc acaagaggtt gataagatca tcgagattgg ccacatgggg   2520
gtcctgagcg gcgcaatcaa gcaaatccta cagctgccgg agctcgctgc atttgatata   2580
tcctacctat cctgtctgtc tcgagggaaa agcgcggtgg acaccattca gcttctcgcc   2640
atggaccttc tccaaggggg ttatcccgta gacttaaacg cagtcaactt cccatacggg   2700
tgcgaagcag ccgaagtcca ggtgctgtcc gatttgccga cctatccctg gaatcacaag   2760
acgagatact ggaaggagcc acgcatcagt cgagctgcac ggcaacgaaa gatcccgtg    2820
catgatctga tcgagttcaa agagcctttg tgccctccgc ttttgcactt gtggcaaaat   2880
gtgcttcgga tctcggatgt gccgtggata cgcgatcacg tcgtgggctc acgaatcctt   2940
ttccccggtg ctgggttcat cagcatggtt attgatgggc tctctcagat ctgtaatcac   3000
gatcccgaaa cttgcggttt aagctacatc ttacgcgacg tggacctggc gcaggcgctg   3060
atcctgccca cggacggaga cgaaggggtg gatttgcgcc taacaattcg cgccgctgat   3120
cagaagagtc tcggaatgcg ggactggcag agattctccg tctattccat cgccggtgat   3180
```

```
aaggacgact ggacggagca ttgtacaggg ctgattcgcg cgcaggtcga tcatcctgtc   3240
tccagctcgt cgatccaaca aaagaccaat ccaccgcaat ggagccggaa gatggcacca   3300
caggacctgt gggcttcgct gcatgcgacg ggaatctgtc acgggccctt attccagaat   3360
attgagcgca ttgaaagcga tggccaggcc tcgtggtgca ctctgaccgt tgccgacaca   3420
gtggcgacta tgccgcacgc ctacgagagc cagcacattg tgcatccaac cacattagac   3480
tcggctatcc aggcggccta tacagtgctt ccatttatgg gaacactgat gaagacagcg   3540
atggtcccca gtcgaatcgg cggcatgaag atacccgcca gcttcgcgag cttggaaccg   3600
ggtgatatgc tgtgcgcaca agcaaaaata aagaaccaag gcctctctgc ctttacaacc   3660
gatgtagctg tgttcaacga gtcagatatg gatgaagagg caggtatcga gctcgaaggg   3720
cttaccttcc agtcgcttgg tgctgttatt agcgactcta ggcgagattt gaccgagaac   3780
gagagcacct acagttcctg gcattgggct cccgacatca ctctgaccaa ttccacatgg   3840
cttgagagga tactaagcac tgggacccag tctcaggaga tcggggtgat gttggagctt   3900
cgacggtgta ctgtccactt tatccaggaa gcaatagaaa acctaacaac ggaagatgtt   3960
gagaggctga gtggtcatct cgtcaaattt tattgctgga tgcaggctca actggcctgc   4020
gctaccaatg gcgagctggg gcaagacagc gccgactggt tgcgagacag tgagcaggag   4080
agacaaagct gcggtccag agtagtcgct gccaccaaca atggcgagat gatctgtcgt   4140
ctgggcccca agctatccgc tatcttgcgt ggcgagctcg accctcttga gctgatgatg   4200 gacgccaac tgttgtctcg atactacatc agggcaatca aatggagccg gtccaatacg   4260
caggcaagcg aactcgtgcg cctctgctgc cacaagaatc cacgtgcccg catccttgag   4320
attggcggtg gaactggggg gtgcacacag ctcatcgtaa acgctttggg gcccacgaag   4380
ccggtaggcc gctacgactt caccgacgtg tctgctggct tcttcgaagc ggctcgaaag   4440
cggttttcgg ggtggcagga tgtgatggac ttccgcaagt tggatatcga gggcgatccc   4500
gaagtgcagg ggtttgactg cggatcctac gacgtggtgt tggcctgtca agttcttcat   4560
gctacaagca acatgcagcg gacattaaac aatgtgcgca agctgttgaa gccgggaggt   4620
aaactcattc ttgttgaaac cacgagggac cagctcgatt tgttttcac attcgggctc   4680 ctgcccggct ggtggctcag tgaagagccg gaacggcagc ttaccccatc actgtctcct   4740
gagttatggc gcagtgtact gagcgctact ggtttcagtg gcgtggacct agaggtccgc   4800
gactgcgaca gtgatgagtt ttacatgatc agcaccatga tgtccacagc tacacctggg   4860
actcctgcaa ctaccttgaa tggaccagcc gaggtgctcc tggtccatgc cggctcgcct   4920
ccgcccatgg attggctgca gaatctgcag gtagccctcg gcgggaaaaa cagttctata   4980
acttcactca aggcgctcca gggcgtttct gatctcaagg ggaagatgtg tgtattcctg   5040
ggggagatgg accgcaccct acttgaaagc gtggtcagtg atgacttcac atccttaacc   5100
tctatgctac agtatagcca aggtactctt tgggttactc gaggagcggc gatggcgtcg   5160
gatgacccaa gaaaggccct gcacctagga ttgctacgca cgctccgcaa tgagaatcac   5220
ggccgtcgat ttgtttcatt ggacctcgac cccttgcgtg atccatggac ggcccagtcc   5280
tgtgacgcca ttgtcaatgt actgaatgca gtcggtgcgt ctcatgagaa ggagtttgag   5340
tatgcagaac gcgatggcac tattcatgtg ccacgaacgt tcagcgactc aagctccagc   5400
gagaaggaag acttggttgt cttggagcca ttccagaatg aaacgcgctt ggtgcgacta   5460
gacgtacaga ctccagggct tctgattct ttgcacttta gctgtgttc tgcggacgaa   5520 gcttggagta gtgagctgcc agaggactgg gtggagattg agccgagggc gttcggtcta   5580
```

```
aactttcgcg atatcatggt tgccatgggc cagttggagt caaatcgagt catgggcttt    5640
gagtgcgctg gtgtggtaac taggttgagc aaagcagcaa caacaggcgc aggagggctt    5700
gcaatcggag accgtgtatg tgcactcatg aaagggcatt gggcatcgag ggtgcggaca    5760
gcccgcacca atgtcatctg catcccaggg accctgagtt tcgaacaagc ggcttccatc    5820
ccactggcct tcacgacagc ttacacctcc ctctacactg ttgctcgcct tcaacggggt    5880
gaaaaagtgc taatccatgg cggcgctgga ggagtcggac aggcggccat catccttgct    5940
caactggtcg gagcggaggt ctttaccact gctggaactc actctaagcg caacttcttg    6000
atcgataagt tcaagctggc ccccgaccat gtcttctcga gcagagactc cggttttatc    6060
gagggtatca gggcttgtac caatggcaag ggggttgatg tggtgctcaa ttctcttgct    6120
gggcctttgc ttcaatatag cttcgactgt ctggtcaatt ttggtcgctt cgtggaaata    6180
ggcaaaaagg atctcgagca aaatagccga ctcaacatgg cgacttttgc gcggaacgtc    6240 tcctttttcct cgattgatat cctgtactgg gaagaagcca agtccgccga aatcttccga    6300
gcattgacgg agattatgcg gctcttggaa caaaagacaa tcgatttgat tgggccgata    6360
tcagagtatc ccatgtcggc tattgagaag gcattccgta cgatgcagag cggccagcac    6420
gtcggtaagc ttgtggtggc tacggctgag acggacatga tccccgttcg ccggggaacc    6480
atgccagtcg cgttgaagct tgacgcgtct tacctgattg tcggtggact gggggggtatt    6540 ggcagacgca tttgcgagtg gatggtggac catggggcac gacatctgct catcctgtcc    6600
cgaagcggtc gtacggatcc cttttgtgact ggcctccaga agcggggctg tgtcgtacgt    6660
atacattcat gtgatgtggc agatgagagt caacttcatg cagttcttca acagtgccat    6720
gaggataaca tgccccccgat ccggggtatc attcaagcgg ccatggtcct caaggacgct    6780
cttgtctcgc aaatgacggc ggacgacttc catgttgctc ttcgtccaaa ggtccagggc    6840
agttggaatc ttcacaagat cgcatctgag gtggactttt tcatcatgct ctcatctctg    6900
gtgggtgtca tgggtggcgc gggtcaagcc aactatgcgg ctgcaggcgc gttccaggac    6960
gcgctcgcac agcaccgggt cgctcaaggg aagcccgctg tcaccatcga cctgggcatg    7020
gtcaagtcaa tcggctatgt ggcagagact gaccccgcag ttgcggagcg attggcccgg    7080
attggctatc aaccgatgca cgaggaagag gtcctcgccg tgctcgagcg agccatgtcg    7140
ccctcctctt cttcggcacc accgtcctct aaccctacta tacccgcctc gcccgctgtc    7200
atcgttaccg gcatcaacac aggccctggc cctcacttca caaacgccga ctggatgcag    7260
gaggcacgtt tcgcgggaat caagtatcgt gatcccctga aggatgaccg tggtggggcc    7320
ttgtcctctt cacagcccgc tgacgaggat agtgtacgcg ctcggctaag tcgggcatct    7380
accgaggagg aggccactgc cctagtggtg caggtgatgg gtcacagact ggtgacgatg    7440
tttggtctca ctgaaagtga gatgtcgcc acacagacat tgtcgagcgt tggagtcgac    7500
tcgctcgtcg ccatcgagct gcgtaactgg attaccgccc aacttaatgt ggatatctcg    7560
gtctttgagt tgatggaggg tcggaccatt gctgaggtgg cggaggtggt agtgaagaag    7620
tatggcgtgg gaagcaaagt ctag                                          7644
```

<210> SEQ ID NO 21
<211> LENGTH: 1575
<212> TYPE: DNA
<213> ORGANISM: Monascus BCRC 38072

<400> SEQUENCE: 21

```
atgacagttc cgacagatac ggtctcgcgt cgcctccagt ctctcgcttg gagcgacata    60
aagcagcatg ccccatggct gccgtcttct cgcactcttg tctcgggatt tctctgtttg   120
atccttcttc agattctgta ctctcgtgga cgcaaatccg acctgcgggt gtataacccg   180
aagaaatggt gggaactcac caccatgagg gccaagcggg agttcgatgc gaatgcgccc   240
gcatggattg aggcctggtt ctccaagaac gaccaaccgc tccgtttcat tgtcgactct   300
ggctattgta ccattttgcc ctcatcgatg ccgacgaat tccggaagat gaaggagctt    360
tgcatgtaca gttttttggg cacggacttc cactctcatc ttcccggatt cgacggcttc   420
aaagaagtca ccagagacgc acatctcatc accaaggtgg tcatgaatca gttccaaacc   480
caagctgcga atacaccaa gcctcttgcc gatgaggcca gcgcgacaat tgcagatatc    540
tttggggaca caaggaatg gcacacggct cctgtctata cgagtgtttt agatttggtg    600
acacgcactg tcactttcat catggtcggg gataaactgg cgcacaacga ggaatggttg   660
gatatcgcca agcaccacgc ggtgactatg gcgattcagg ctcgccaact ccgcctctgg   720
cccgtcattc tgcgccctat agtccactgg ctcgagcccc agggagccaa actgcgggcg   780
caagtccgac gagcccggca gcttctcgag cccatcatcc aggagcgacg cgccgagaag   840
gccaaatgcc tcgcccaagg gatcgagccg ccgcgctacg tcgattccat tcagtggttt   900
gaagacaccg ccaagggcca atggtacgat gcggcggggg cgcagttggc catggacttt   960
gccggcatct acggcacctc tgacctgatg atcggcgggc tggtcgacat cgtccgccac  1020
ccgcatctca tcgagcccct tcgcaacgag atccggaccg tcatcggcga ggaaggctgg  1080
acgccggcct cgttgtacaa actcaagctt ctggacagct gtctcaagga atcgcagcgc  1140
gtcaagcccg tagaatgcgc cacgatgcgc agctacgcgc tccagaacgt gaccttctcc  1200
aatggaacct tgtcccgaa aggcgagctg gtagctgtgg cggccgaccg catgagcaac   1260
cctgaagtct ggcctgagcc gaagaagtac gacccgtacc gatacatgcg cctgcgagag  1320
gatcccgaca aggcgttcag tgcccagctg gagaacacca acggtaacca tatcggcttt  1380
gggtggcatc ctcgggcgtg tcccggacgg ttcttcgcct ccaaggagat caagatcatg  1440
ttggcgtttc tgctgattcg gtacgactgg aagctggtgc caaacgagcc gttgcagtat  1500
taccgtcatt ccttcagcgt gcgcatccat cctgccacca gcttatgat gcgccgtcgg   1560 gacgaagatc tctga                                                   1575
```

<210> SEQ ID NO 22
<211> LENGTH: 792
<212> TYPE: DNA
<213> ORGANISM: Monascus BCRC 38072

<400> SEQUENCE: 22

```
atgcgtatcc aacgcacccc cgcgcccccc aaagcgcccc gggccctcct ctgcgtgcac    60
ggcgccggct gctcccccgc catcttccgc gtgcagctct ccaaactccg cgccgcttta   120
cgggaagact tgaattcgt ctacgcaacg gcacccttcc cttccgcccc tggacccggg    180
atcctgccca cgttcgaagg cctcgggccc tattacacct ggttcgaggg ttctccgtct   240
ggtgctgctg ccaaagggga taacagcaac agcaacgaca gcaactcttc tcccaccgta   300
cacgaccgcc tcgccgccgt ccacgaaccc gtccgccgcg ccatcgccga atggcagacc   360
cagaacccca gcatccccat cgtgggaacc gtcagtttct ccgagggcgc tcttgtgacc   420
gccctgctgc tctggcagca gcagatgggt aggataccct ggctcccggt catgcaggtt   480
gcgatgttca tctgctgctg gtatcagcat gaggcgactc agtatatgcg ggaggaggta   540
```

```
ggctgcggcg gtgatggtgg cattgacggt gagaagttgg tgatccgggg ggtgctgtcg    600
ctgcacctgc agggtcgtga tgactttgcc ctggcgggtt cgaagatggt ggtggcgcag    660
cattttgtgc ccggggaggc gcaggtgttg gagtttgcgg gccggcatca tttcccgaat    720
cggccgcgcg atgtgttgga gacggttaag cggtttaggc agctgtgtgt gagggctaga    780
gtcattgggt ga                                                        792
```

```
<210> SEQ ID NO 23
<211> LENGTH: 1083
<212> TYPE: DNA
<213> ORGANISM: Monascus BCRC 38072

<400> SEQUENCE: 23
atgaccatca ccttcaccct accacctcac cagactgcgc tgacagtgga cgagcatgac     60
aaagtcacca tctgggacgt cgcccccctgt ccaagcctcc ccccgatca ggtctgcgtg    120 cgcgtcgagg ccgtagccct caaccccagc gacacgaaga tgcgcggcca attcgccacc    180
ccctacgcct tcctgggcac cgactacgcc ggcaccgtcg tcgccgtggg atcgcaggtc    240
acgcacatcc aagtcgggga ccgggtctac ggcgcccaga acgagatgtg tccgcgcacc    300
ccccaccagg gcgccttctc gcagtacacg gtcacccgcg gccgcatctg gccacggtc     360 cctgagggct ggtccttcga gcaggccgcg tcgttgcccg cgggcatcag cacggccggc    420
ctggcgatga gctgctcgg gctgcccttta ccggatccca atgctacgac ggcaccggcc    480
cttccgaagc ccgtgtatgt tttggtgtat ggggtagca ccgctactgc gacgattgtg    540
atgcagatgc tacgcttgtc cggatacatc cccatagcca catgctcccc gcacaatttc    600
gacctcgcca aaaagcacgg cgcagaagat gtctttgact atcgtgatgc cggtctcgcg    660
cagacgattc gcacatacac caaaaacaac ctccgctacg ccctcgattg catcaccaac    720
gtcgagtcca ccaccctctg cttcgccgcc atcggccgcg ccggcggccg ctatgtctcc    780
ctgaacccgt tcccggaaca cgcggcgacc cggaaaatgg tcaccgccga ctggaccctg    840
gggccgacca ttttcgggga aggtcgact tggccggcgc cgtatgggcg gccggggagc    900
gagaaggacc gcgcattcgg cgaggagttg tggcgcgttg cggcaaggct cgtggaggat    960
gggaagatcg tgcaccatcc tctgcgggtg attcctggcg ggttcgaggc cattaagcag   1020
gggatggagt tggttaggac tgggcagttg tcggagaga aggttgtggt gaagttgggg   1080
taa                                                                 1083
```

```
<210> SEQ ID NO 24
<211> LENGTH: 1242
<212> TYPE: DNA
<213> ORGANISM: Monascus BCRC 38072

<400> SEQUENCE: 24
atgcgtcaat ttctctcctc tgatcgcatc aactctgaaa tcccccagga gaaaagcgaa     60
atggtaggat tcagtgatat cgacaatagc agccgccaga tcaaagaaat ggaagccgct    120
ttccgatcgg ccgtgaaaac agggcagatc ccggggggcag tcatcatggc tcgagatcat    180
agtggccgac tgaactatac gcgctgcttc ggggcgcgga cggtggtgcg cgatgagtgt    240
aaccgactcc ctccgatgca ggtcgacacc ccctgccggc tggcgagtgc caccaagctg    300
cttacgacga tcatggcgct gcaatgcgtg gagcggggc tcgtgaggtt ggatgagacg    360
gtggatcgac tgctgccgga tttgagtgcg atgaaggtgc tggagggggtt tgatgccgcg    420
```

```
ggggagccga agatgagaga gcggaaggggg aagattactt tgaaacatct cctaacacac      480
acctccggcc tgtcctacgt cttcctccac ccctcctcc gagaatacat ggccaaaggc       540
cacctccaga cggctgagaa attcgggatc cagagtcggc tggcgccccc ggccgtcaac      600
gacccgggcg ccgagtggat ctacggcgcc aacctcgact ggacggggaa gctggtcgag      660
cgcgccacgg gcctggacct ggagcagtac ctccaagaga acatctgcgc gccgctgaac      720
atcaccgaca tgaccttcaa gctgcagcag cgacccgatc tgctggcgcg gcgcgccgac      780
cagacgcacc gcaacaaggc ggacggccgc ctgcgctacg acgactcggt gtacttccgg      840
tccgacggcg acgagtgctt tggggccag ggggtcttct cgggcccga atcctacatg        900 aaggtcgtgc actccctgct gcagcgcgac gggcgcctgc tgcggcccga ccgtggac        960 ttgatgttcc agcccgcgct cgatgcgcaa acggagaagc agatgaacca gcatatggac     1020
gcgagcccgc acatcaacta cggtgggccg atgcccatgg tgttgcggcg gagttttggg     1080
cttggtggga tgattgcctt ggaggatctg gatgggcaga gtggcgccg aaagggctgt      1140 ttaacctttg gcggcgggcc gaatattgta tgggtaatgt tactctcagc cctacgcttc     1200
gttttcttct tcttcttctt cttcttcttc tgctctagct ga                        1242
```

<210> SEQ ID NO 25
<211> LENGTH: 1368
<212> TYPE: DNA
<213> ORGANISM: Monascus BCRC 38072

<400> SEQUENCE: 25

```
atggccctat cgccagtcca ggatccccct tcacacaccg acaaaactat gccccgccgt       60
gcatttcgcc gatcttgtga ccgatgccat gcacagaaga ttaagtgtat aggcagcgag      120
ggagctgttg cccgtgcttc atgtcaacgt tgccagcaag ctggactgcg gtgcgtttac      180
agcgagcgat gccctaagcg caagctaccc aaacccaacc cagcggaatc ttcccctgca      240
agcagcacgg ccggcctgca cacctcttct tcagattctt cgcccctgt tccctccgat       300 ggcttgccgc tagacctgcc agggccggat tcctcaggcg tctccctcca attcctcgac      360
ccgtctgccg actgcgactg gccttggtcc tcgatcggtg tggacgaaac cgttgtcaac      420
aattgcttgg acttatctca tggccatggc catggagacc tcagttgcca gctcgagctg      480
cctatgccag atcttccctc cccttcgaa ttctcggccg aaaaatctcc ctcaccgtcg       540
gtgtctggca gcattgccgg agctgtcagt gcacaacgag aactcttcga tggcttgtcg     600
acggtgtccc aggaattgga agccatcctt ctggctgtgg cggtggagtg gccaaaacag     660
gaaatctgga cttaccccat tgggacgttc ttcaacgcat cacgaagact tcttgtatat     720
ctccaacaac aatccaacac ccgcagcgac caaggcatgc tgaatgaatg tctacgaacc    780
aagaacctct tcatggcagt gcattgttat atgctgatcg tgaagatttt cacctctctc    840
tcggaattgc tgctatccca gatccggcat tcccaggctg ccagctgac acccttggaa     900 gggcatcagt tcgagccacc accgagcagc agcagggacc gtagcagcgt cgataccatg    960
cccatcttca cccgaatct ccacatcggc gggttgtttt cttatctcaa ccccttcatg     1020
cacgccctat cctcggcttg caccaccttg cgcgtcggcg tacagttgct gcgagagaat    1080
gagagtgctc ttgggatccc ccggcgcag ggggtggcgg cctctgtgag tatgggcaag     1140
gaggagtggg cagacggcga ggatgtagcc agtgcagtga cgacggcgga cgaggatctc    1200
cgccagccgg cctcgcggat cttatccatg gtctggagcg atgaggtggg cgaccagaag    1260
gccaagtctg ctgatgctgc tggtccgcga agccgaaccc tggcggtgct acggcggtgt    1320
```

```
aatcgagaga tcttttccct ggcccgccaa cacaacctgg cctcctaa        1368

<210> SEQ ID NO 26
<211> LENGTH: 1632
<212> TYPE: DNA
<213> ORGANISM: Monascus BCRC 38072

<400> SEQUENCE: 26
atggcttccc accagtctga gaaagagaag ccacagagct gcaccactga agtccaggtc    60
agccatgtca ccggcctaaa gctaggactg gtagtaacct cggtgaccct ggtggtgttt   120
ttgatgttgt tggacatgtc tatcattgtg acagctatcc cccatatcac tgctcagttt   180
cattcccttg gggatgttgg atggtatgga agtgcgtatc ttttgtcgag ctgtgctcta   240
cagcccttgg cagggaagct ctacactctc ttgacattga agtatacctt cctagcattc   300
ctcggggtgt ttgaagtcgg atcagctctc tgtggcgccg cgcgttgttc aactatgttg   360
atcgtggggc gcgcagtggc tggcatggga ggatcggggc tcaccaatgg agccatcacc   420
atcctcgcct ctgcagctcc aaaacaacag caaccactgt taatcgggat catgatgggt   480
ctgagccaaa ttgccattgt ctgtggacca ttgctgggag gtgcttttac ccaacacgca   540
agttggcggt ggtgcttcta tatcaatctt cctgtcggag cgctggccgc catcctcctt   600
ctcgccatcc acattcctaa gagtgtgcca acatcggatt gcacaatgcc tgctcccaga   660
gctgttgggg tccgggtcat cctgagtcag ctcgatctcc tggggtttgt gctcttcgcc   720
gcctttgccg tgatgatctc acttgcgtta gaatggggcg gtccgattta tgtgggat    780
agctccgtaa tcatcggctt gttctgtggt gccggcatct cgctggtggt gtttgggttc   840
tgggaacgct acgtaggcaa ctcgatggcg atgattcctt tctcggtggc cagtcgtcga   900
caagtctggt gctcgtgtct tttcttgggc ttttttctccg gggccttgct caccttctct   960
tactaccttc ctatctactt ccaggccgtg aaggacgtct ctcccaccat gagtgggatg  1020
tatatgcttc caggcatagg gggacaaaatt gtgatggcga tcgtctccgg cgcaatcatc  1080
ggcaaaacgg gtattacat tccctgggcg cttgccagtg ggatcatcgt atctatctcc  1140
gcaggcctgg tatcgacctt ccagccgcat acctcaatcg cagcgtgggt gatgtatcaa  1200
ttcatggggg gctttggtcg aggatgtgga atgcagaccc ccatcattgc cattcaacat  1260
gccctgccac cacaaatgag tgcgctcggt atctcgctgg ccatgttcgg ccagaccttc  1320
ggcggctccc tcttcctcac cttggccaag ctcgtcttca gcgccggcct tgacgccggc  1380
ttacgcgagt atgcgcccgc cgtcagcgca gaggcggtga cggccgcggg cgccacgggc  1440
ttccgcgatg tcgtccccgc aaatctcctt tctcaggttc tcctggcata ctgtaaaggg  1500
atagaccata cattctacct tgcggtcggg gcatcggag ccactttttt gtttgcgtgg   1560
ggaatgggtc aggtcggttt gatttggtgg ggggaggaaa ggacggggtt cggccgcgat   1620
gaacgagtct ag                                                     1632

<210> SEQ ID NO 27
<211> LENGTH: 2046
<212> TYPE: DNA
<213> ORGANISM: Monascus BCRC 38072

<400> SEQUENCE: 27
atggcatcgg cagccgtgac gccaaagctt ggctgggtgc agcaccaggt aaccaacgga    60
ttacatgccg tggtcggcca agtgtgtcga catcccatcc acacgttgct ggtgactgct   120
```

-continued

```
ctgatcgccg caacgactta tctccatgtt ttggaaggca cctttcgcgc agccaaccta    180
ggtcccggtt ccaagactga cgcagccccc ttcgacgtcc agtcgttcct ctggggcagc    240
cgaagtcttc gcctgggcga dacaagctcg tggagatggc aggtgggcga cttgtctgag    300
gcgactggcg atggccaagt caatcaccac tgggctcttg tcactctcag cttccccggc    360
gcctcggtcg atgatcgcag ccctgccttt ctgtggaacg cactgcccga ctctgtgggc    420
gcagagccga tcacgccaac ctccaacttc ttcacctcga tctccaatga attctcgctg    480
gcctttcgag tcccatacac ccaattgagc gattttctgg aggcggtgga gtttgttgcc    540
tcggataagg aggatcgtag ctgggccatc aggtttcctc acgagaggg caagcccatt    600 tcgctgggcc gctggctcgg gaactcgtgg ctgtcgttcc ttcaccgggc taaacacgcc    660
gagacggtag acatggctat catcggttta ggctacctcg ctctgaatat gaccctggtc    720
tctctcttcc gagcgatgcg tcagttgggc tcgcgtttct ggctggcagc ctccgtgctg    780
ctctctgggg cgtttgcctt tgtattcggg ctcggtgtca cgactgcctg cggcgtgcca    840
gtcgacatgc ttcttctgtc ggaagggatt cccttcctgg ttttgaccgt ggggtttgag    900
aagccgatcc gatttacccg tgctgttctc tacgcatcga atcagctccg gcgcgggttg    960
cagcagcggg acgttgccga caagcatgac agccggcagc gccatatgat ccccaacgcc   1020
atgctattcg ccatcaacag agaaggatgg tccattgtcc agtcgtacct tcttgagatc   1080
ggggctctcg cattgggtgc ggtcttccgg ccacgggaac gattcggcca gttctgcttc   1140
ctggccgcat ggatggtgct cttcgacgcc atccttcttt tcaccttcta cgccaccatt   1200
ctctgcgtca aactggaggt gacccggatg caaaaccccg gcaccctgga tctggcagac   1260
gaccaacatg ggccgcgcat cttcgggtac aaggtcaatc cgaccagcct ggcccggtgg   1320
aagctaatca tggtaggcgg gttcgtgctc ttcaacgtcc tccaactgtc atcgttcttt   1380
tatcgcatca tgggaggctt catgaccaat gccgctctga ccccgaccac cgtcagtccg   1440
ttcaaagtgg ctgccaacgg gctgaacgat atttatttgg ccgcccgtgc cggcggagtt   1500
gagacgtggg tcacggtgct accgccgatt cgatatgtca tggaagcatc tgggttggaa   1560
atgtcggccg gcagacgtcc tgtatttgat ggcgtgctgg ccggactgga gagcccctg    1620 ggtcggctct gtctcatggg cgctttggtt ttcagtcttt acctcaataa ccacctgatc   1680
ccggccgccc gctggcattt tttccccggc gcaccgaaag aatccgctgc gcctgcaccc   1740
ccttcatcgc ccgcatcggt ccccagcgct gtaccggtcc ctgcgccctc ctctcgcagc   1800
ttcgaggaaa tcgaggccct attcaaagcg aaccaggcgg aatctctgac cgatgacgag   1860
ctggcggagc tctgtctccg tggtaagatt gccggataca gcttagagaa gaccttggaa   1920
agcattgcct ccgcaggttc ttcaagcaca gcaacaacta ggctggaggc tttcacgcgc   1980
gcggttcgca tccgccgggc cgccgtgtcg cggacgcctt cgactcggga cctcagcggc   2040
ggcatc                                                              2046
```

<210> SEQ ID NO 28
<211> LENGTH: 1052
<212> TYPE: PRT
<213> ORGANISM: Monascus BCRC 38072

<400> SEQUENCE: 28

Met Ala Ser Ala Ala Val Thr Pro Lys Leu Gly Trp Val Gln His Gln
1               5                   10                  15

Val Thr Asn Gly Leu His Ala Val Val Gly Gln Val Cys Arg His Pro
            20                  25                  30

-continued

Ile His Thr Leu Leu Val Thr Ala Leu Ile Ala Thr Thr Tyr Leu
    35                  40                  45

His Val Leu Glu Gly Thr Phe Arg Ala Ala Asn Leu Gly Pro Gly Ser
 50                  55                  60

Lys Thr Asp Ala Ala Pro Phe Asp Val Gln Ser Phe Leu Trp Gly Ser
 65                  70                  75                  80

Arg Ser Leu Arg Leu Gly Glu Thr Ser Ser Trp Arg Trp Gln Val Gly
                 85                  90                  95

Asp Leu Ser Glu Ala Thr Gly Asp Gly Gln Val Asn His His Trp Ala
                100                 105                 110

Leu Val Thr Leu Ser Phe Pro Gly Ala Ser Val Asp Asp Arg Ser Pro
            115                 120                 125

Ala Phe Leu Trp Asn Ala Leu Pro Asp Ser Val Gly Ala Glu Pro Ile
        130                 135                 140

Thr Pro Thr Ser Asn Phe Phe Thr Ser Ile Ser Asn Glu Phe Ser Leu
145                 150                 155                 160

Ala Phe Arg Val Pro Tyr Thr Gln Leu Ser Asp Phe Leu Glu Ala Val
                165                 170                 175

Glu Phe Val Ala Ser Asp Lys Glu Asp Arg Ser Trp Ala Ile Arg Phe
                180                 185                 190

Pro His Gly Glu Gly Lys Pro Ile Ser Leu Gly Arg Trp Leu Gly Asn
            195                 200                 205

Ser Trp Leu Ser Phe Leu His Arg Ala Lys His Ala Glu Thr Val Asp
    210                 215                 220

Met Ala Ile Ile Gly Leu Gly Tyr Leu Ala Leu Asn Met Thr Leu Val
225                 230                 235                 240

Ser Leu Phe Arg Ala Met Arg Gln Leu Gly Ser Arg Phe Trp Leu Ala
                245                 250                 255

Ala Ser Val Leu Leu Ser Gly Ala Phe Ala Phe Val Phe Gly Leu Gly
            260                 265                 270

Val Thr Thr Ala Cys Gly Val Pro Val Asp Met Leu Leu Leu Ser Glu
        275                 280                 285

Gly Ile Pro Phe Leu Val Leu Thr Val Gly Phe Glu Lys Pro Ile Arg
    290                 295                 300

Phe Thr Arg Ala Val Leu Tyr Ala Ser Asn Gln Leu Arg Arg Gly Leu
305                 310                 315                 320

Gln Gln Arg Asp Val Ala Asp Lys His Asp Ser Arg Gln Arg His Met
                325                 330                 335

Ile Pro Asn Ala Met Leu Phe Ala Ile Asn Arg Glu Gly Trp Ser Ile
            340                 345                 350

Val Gln Ser Tyr Leu Leu Glu Ile Gly Ala Leu Ala Leu Gly Ala Val
    355                 360                 365

Phe Arg Pro Arg Glu Arg Phe Gly Gln Phe Cys Phe Leu Ala Ala Trp
370                 375                 380

Met Val Leu Phe Asp Ala Ile Leu Leu Phe Thr Phe Tyr Ala Thr Ile
385                 390                 395                 400

Leu Cys Val Lys Leu Glu Val Thr Arg Met Gln Asn Pro Gly Thr Leu
                405                 410                 415

Asp Leu Ala Asp Asp Gln His Gly Pro Arg Ile Phe Gly Tyr Lys Val
            420                 425                 430

Asn Pro Thr Ser Leu Ala Arg Trp Lys Leu Ile Met Val Gly Gly Phe
        435                 440                 445

```
Val Leu Phe Asn Val Leu Gln Leu Ser Ser Phe Phe Tyr Arg Ile Met
    450                 455                 460
Gly Gly Phe Met Thr Asn Ala Ala Leu Thr Pro Thr Thr Val Ser Pro
465                 470                 475                 480
Phe Lys Val Ala Ala Asn Gly Leu Asn Asp Ile Tyr Leu Ala Ala Arg
                485                 490                 495
Ala Gly Gly Val Glu Thr Trp Val Thr Val Leu Pro Pro Ile Arg Tyr
            500                 505                 510
Val Met Glu Ala Ser Gly Leu Glu Met Ser Ala Gly Arg Arg Pro Val
        515                 520                 525
Phe Asp Gly Val Leu Ala Gly Leu Glu Ser Pro Leu Gly Arg Leu Cys
    530                 535                 540
Leu Met Gly Ala Leu Val Phe Ser Leu Tyr Leu Asn Asn His Leu Ile
545                 550                 555                 560
Pro Ala Ala Arg Trp His Phe Ser Pro Gly Ala Pro Lys Glu Ser Ala
                565                 570                 575
Ala Pro Ala Pro Pro Ser Ser Pro Ala Ser Val Pro Ser Ala Val Pro
            580                 585                 590
Val Pro Ala Pro Ser Ser Arg Ser Phe Glu Glu Ile Glu Ala Leu Phe
        595                 600                 605
Lys Ala Asn Gln Ala Glu Ser Leu Thr Asp Asp Glu Leu Ala Glu Leu
    610                 615                 620
Cys Leu Arg Gly Lys Ile Ala Gly Tyr Ser Leu Glu Lys Thr Leu Glu
625                 630                 635                 640
Ser Ile Ala Ser Ala Gly Ser Ser Ser Thr Ala Thr Arg Leu Glu
                645                 650                 655
Ala Phe Thr Arg Ala Val Arg Ile Arg Arg Ala Ala Val Ser Arg Thr
                660                 665                 670
Pro Ser Thr Arg Asp Leu Ser Gly Gly Ile Gln Glu Ser Leu Leu Pro
            675                 680                 685
Tyr Arg Asn Tyr Asn Tyr Glu Leu Val His Gly Ala Cys Cys Glu Asn
        690                 695                 700
Val Ile Gly Tyr Leu Pro Leu Pro Leu Gly Leu Ala Gly Pro Met Val
705                 710                 715                 720
Ile Asp Gly Gln Ala Tyr Phe Ile Pro Met Ala Thr Thr Glu Gly Val
                725                 730                 735
Leu Val Ala Ser Ala Ser Arg Gly Cys Lys Ala Ile Asn Thr Gly Gly
                740                 745                 750
Gly Ala Val Thr Met Leu Lys Gly Asp Gly Met Thr Arg Gly Pro Cys
            755                 760                 765
Leu Gly Phe Pro Ser Ala Lys Arg Ala Ala Glu Ala Gln Arg Trp Val
    770                 775                 780
Glu Ser Pro Val Gly His Gln Val Leu Thr Asp Ala Phe Asn Ala Thr
785                 790                 795                 800
Ser Arg Phe Ala Arg Leu Gln Thr Leu Thr Val Ala Gln Ala Gly Thr
                805                 810                 815
Tyr Leu Tyr Ile Arg Phe Arg Thr Thr Thr Gly Asp Ala Met Gly Met
                820                 825                 830
Asn Met Ile Ser Lys Gly Val Glu Lys Ala Leu Gln Ala Met Thr Ala
            835                 840                 845
His Gly Phe Pro Asp Met Asn Thr Ile Thr Leu Ser Gly Asn Phe Cys
    850                 855                 860
Ala Asp Lys Lys Ser Ala Ala Ile Asn Trp Ile Gly Gly Arg Gly Lys
```

```
                865                 870                 875                 880
Ser Val Ile Ala Glu Ala Thr Ile Pro Ala Asp Thr Val Arg Lys Val
                885                 890                 895
Leu Lys Thr Asp Ile Asp Ala Leu Val Glu Leu Asn Thr Ala Lys Asn
                900                 905                 910
Leu Val Gly Ser Ala Met Ala Gly Ser Met Gly Gly Phe Asn Ala His
                915                 920                 925
Ala Ser Asn Leu Val Gln Ala Val Phe Leu Ala Thr Gly Gln Asp Pro
                930                 935                 940
Ala Gln Asn Val Glu Ser Ser Cys Ile Thr Thr Met Lys Lys Ile
945                 950                 955                 960
Asp Gly Asn Leu His Ile Ala Val Ser Met Pro Ser Met Glu Val Gly
                965                 970                 975
Thr Ile Gly Gly Gly Thr Ile Leu Glu Ala Gln Gly Ala Met Leu Asp
                980                 985                 990
Leu Leu Gly Val Arg Gly Ala His  Pro Thr Asp Pro Gly  Ala Asn Ala
                995                 1000                1005
Arg Arg  Leu Ala Arg Ile Val  Ala Ala Ala Val Leu  Ala Gly Glu
1010                1015                1020
Leu Ser  Thr Cys Ser Ala Leu  Ala Ala Gly His Leu  Val Asn Ala
1025                1030                1035
His Met  Arg His Asn Arg Ser  Ala Ala Ser Ser Glu  Lys Lys
1040                1045                1050
```

<210> SEQ ID NO 29
<211> LENGTH: 19
<212> TYPE: DNA
<213> ORGANISM: Artificial Sequence
<220> FEATURE:
<223> OTHER INFORMATION: Mplov1 forward primer for Monascus monacolin K
      probe

<400> SEQUENCE: 29
tccactgccg tttatgttg                                                  19

<210> SEQ ID NO 30
<211> LENGTH: 19
<212> TYPE: DNA
<213> ORGANISM: Artificial Sequence
<220> FEATURE:
<223> OTHER INFORMATION: Mplov2 reverse primer for Monascus monacolin K
      probe

<400> SEQUENCE: 30
tcgtcatctt cacccatc                                                   19

<210> SEQ ID NO 31
<211> LENGTH: 20
<212> TYPE: DNA
<213> ORGANISM: Artificial Sequence
<220> FEATURE:
<223> OTHER INFORMATION: forward primer for mkA gene

<400> SEQUENCE: 31
atagctccga gaatggtccc                                                 20

<210> SEQ ID NO 32
<211> LENGTH: 20
<212> TYPE: DNA
<213> ORGANISM: Artificial Sequence
<220> FEATURE:

<223> OTHER INFORMATION: reverse primer for mkA gene

<400> SEQUENCE: 32
ccatcaagga tgctctgtcg                                              20

<210> SEQ ID NO 33
<211> LENGTH: 22
<212> TYPE: DNA
<213> ORGANISM: Artificial Sequence
<220> FEATURE:
<223> OTHER INFORMATION: forward primer for mkB gene

<400> SEQUENCE: 33
ctagactttg cttcccacgc ca                                           22

<210> SEQ ID NO 34
<211> LENGTH: 20
<212> TYPE: DNA
<213> ORGANISM: Artificial Sequence
<220> FEATURE:
<223> OTHER INFORMATION: reverse primer for mkB gene

<400> SEQUENCE: 34
cattgtcgag cgttggagtc                                              20

<210> SEQ ID NO 35
<211> LENGTH: 20
<212> TYPE: DNA
<213> ORGANISM: Artificial Sequence
<220> FEATURE:
<223> OTHER INFORMATION: forward primer for mkC gene

<400> SEQUENCE: 35
ggcctgagcc gaagaagtac                                              20

<210> SEQ ID NO 36
<211> LENGTH: 20
<212> TYPE: DNA
<213> ORGANISM: Artificial Sequence
<220> FEATURE:
<223> OTHER INFORMATION: reverse primer for mkC gene

<400> SEQUENCE: 36
tcagagatct tcgtcccgac                                              20

<210> SEQ ID NO 37
<211> LENGTH: 20
<212> TYPE: DNA
<213> ORGANISM: Artificial Sequence
<220> FEATURE:
<223> OTHER INFORMATION: forward primer for mkD gene

<400> SEQUENCE: 37
tgatgacttt gccctggcgg                                              20

<210> SEQ ID NO 38
<211> LENGTH: 20
<212> TYPE: DNA
<213> ORGANISM: Artificial Sequence
<220> FEATURE:
<223> OTHER INFORMATION: reverse primer for mkD gene

<400> SEQUENCE: 38
tcacccaatg actctagccc                                              20

```
<210> SEQ ID NO 39
<211> LENGTH: 20
<212> TYPE: DNA
<213> ORGANISM: Artificial Sequence
<220> FEATURE:
<223> OTHER INFORMATION: forward primer for mkE gene

<400> SEQUENCE: 39
ttctctcccg acaactgccc                                            20

<210> SEQ ID NO 40
<211> LENGTH: 20
<212> TYPE: DNA
<213> ORGANISM: Artificial Sequence
<220> FEATURE:
<223> OTHER INFORMATION: reverse primer for mkE gene

<400> SEQUENCE: 40
aatggtcacc gccgactgga                                            20

<210> SEQ ID NO 41
<211> LENGTH: 20
<212> TYPE: DNA
<213> ORGANISM: Artificial Sequence
<220> FEATURE:
<223> OTHER INFORMATION: forward primer for mkF gene

<400> SEQUENCE: 41
gccccgaatc ctacatgaag                                            20

<210> SEQ ID NO 42
<211> LENGTH: 20
<212> TYPE: DNA
<213> ORGANISM: Artificial Sequence
<220> FEATURE:
<223> OTHER INFORMATION: reverse primer for mkF gene

<400> SEQUENCE: 42
ggcccaccgt agttgatgtg                                            20

<210> SEQ ID NO 43
<211> LENGTH: 20
<212> TYPE: DNA
<213> ORGANISM: Artificial Sequence
<220> FEATURE:
<223> OTHER INFORMATION: forward primer for mkG gene

<400> SEQUENCE: 43
cctcgctctg aatatgaccc                                            20

<210> SEQ ID NO 44
<211> LENGTH: 20
<212> TYPE: DNA
<213> ORGANISM: Artificial Sequence
<220> FEATURE:
<223> OTHER INFORMATION: reverse primer for mkG gene

<400> SEQUENCE: 44
tcggatcggc ttctcaaacc                                            20

<210> SEQ ID NO 45
<211> LENGTH: 20
<212> TYPE: DNA
<213> ORGANISM: Artificial Sequence
<220> FEATURE:
<223> OTHER INFORMATION: forward primer for mkH gene
```

-continued

```
<400> SEQUENCE: 45
acctcatcgc tccagaccat                                            20

<210> SEQ ID NO 46
<211> LENGTH: 20
<212> TYPE: DNA
<213> ORGANISM: reverse primer for mkH gene

<400> SEQUENCE: 46
ctgcgagaga atgagagtgc                                            20

<210> SEQ ID NO 47
<211> LENGTH: 20
<212> TYPE: DNA
<213> ORGANISM: Artificial Sequence
<220> FEATURE:
<223> OTHER INFORMATION: forward primer for mkI gene

<400> SEQUENCE: 47
ctagactcgt tcatcgcggc                                            20

<210> SEQ ID NO 48
<211> LENGTH: 20
<212> TYPE: DNA
<213> ORGANISM: Artificial Sequence
<220> FEATURE:
<223> OTHER INFORMATION: reverse primer for mkI gene

<400> SEQUENCE: 48
ccatacattc taccttgcgg                                            20

<210> SEQ ID NO 49
<211> LENGTH: 20
<212> TYPE: DNA
<213> ORGANISM: Artificial Sequence
<220> FEATURE:
<223> OTHER INFORMATION: forward primer p3

<400> SEQUENCE: 49
ccatcaagga tgctctgtcg                                            20

<210> SEQ ID NO 50
<211> LENGTH: 20
<212> TYPE: DNA
<213> ORGANISM: Artificial Sequence
<220> FEATURE:
<223> OTHER INFORMATION: reverse primer p4

<400> SEQUENCE: 50
tcaagccaac ttcaacgcgg                                            20

<210> SEQ ID NO 51
<211> LENGTH: 30
<212> TYPE: DNA
<213> ORGANISM: Artificial Sequence
<220> FEATURE:
<223> OTHER INFORMATION: forward primer p1

<400> SEQUENCE: 51
ggaattcatg tacgtaggac gcattggtgc                                 30

<210> SEQ ID NO 52
<211> LENGTH: 20
<212> TYPE: DNA
<213> ORGANISM: Artificial Sequence
```

```
<220> FEATURE:
<223> OTHER INFORMATION: reverse primer p2

<400> SEQUENCE: 52
tcgcgaggac ggacaaagtt                                                    20

<210> SEQ ID NO 53
<211> LENGTH: 29
<212> TYPE: DNA
<213> ORGANISM: Artificial Sequence
<220> FEATURE:
<223> OTHER INFORMATION: forward primer for sfp gene with BamHI site

<400> SEQUENCE: 53
cgggatccca tgaagattta cggaattta                                          29

<210> SEQ ID NO 54
<211> LENGTH: 36
<212> TYPE: DNA
<213> ORGANISM: Artificial Sequence
<220> FEATURE:
<223> OTHER INFORMATION: reverse primer for sfp gene with NotI site

<400> SEQUENCE: 54
atagtttagc ggccgcttat aaaagctctt cgtacg                                  36

<210> SEQ ID NO 55
<211> LENGTH: 28
<212> TYPE: PRT
<213> ORGANISM: A. terreus lovB

<400> SEQUENCE: 55

Asn Arg Ile Ser Tyr Phe Phe Asp Trp His Gly Pro Ser Met Thr Ile
1               5                   10                  15

Asp Thr Ala Cys Ser Ser Ser Leu Val Ala Val His
            20                  25

<210> SEQ ID NO 56
<211> LENGTH: 28
<212> TYPE: PRT
<213> ORGANISM: P. citrinum mlcA

<400> SEQUENCE: 56

Asn Arg Val Ser Tyr Phe Phe Asp Trp His Gly Pro Ser Met Thr Ile
1               5                   10                  15

Asp Thr Ala Cys Ser Ser Ser Leu Ala Ala Val His
            20                  25

<210> SEQ ID NO 57
<211> LENGTH: 28
<212> TYPE: PRT
<213> ORGANISM: rat FAS

<400> SEQUENCE: 57

Asn Arg Ile Ser Phe Phe Phe Asp Phe Lys Gly Pro Ser Ile Ala Leu
1               5                   10                  15

Asp Thr Ala Cys Ser Ser Ser Leu Leu Ala Leu Gln
            20                  25

<210> SEQ ID NO 58
<211> LENGTH: 28
<212> TYPE: PRT
<213> ORGANISM: P. patulum MSAS
```

-continued

<400> SEQUENCE: 58

Asn Arg Ile Ser Tyr His Leu Asn Leu Met Gly Pro Ser Thr Ala Val
1               5                   10                  15

Asp Ala Ala Cys Ala Ser Ser Leu Val Ala Ile His
            20                  25

<210> SEQ ID NO 59
<211> LENGTH: 28
<212> TYPE: PRT
<213> ORGANISM: A. terreus lovF

<400> SEQUENCE: 59

Asn Arg Val Ser His Phe Tyr Asp Leu Arg Gly Pro Ser Val Ser Ile
1               5                   10                  15

Asp Thr Ala Cys Ser Thr Thr Leu Thr Ala Leu His
            20                  25

<210> SEQ ID NO 60
<211> LENGTH: 28
<212> TYPE: PRT
<213> ORGANISM: M. purpureus mkB

<400> SEQUENCE: 60

Ser Arg Val Ser His Phe Tyr Asp Leu Arg Gly Pro Ser Val Thr Val
1               5                   10                  15

Asp Thr Ala Cys Ser Thr Thr Leu Thr Ala Leu His
            20                  25

<210> SEQ ID NO 61
<211> LENGTH: 28
<212> TYPE: PRT
<213> ORGANISM: P. citrinum mlcB

<400> SEQUENCE: 61

Asn Arg Ile Ser His Phe Tyr Asp Leu Arg Gly Pro Ser Val Ile Val
1               5                   10                  15

Asp Thr Ala Cys Ser Thr Thr Leu Thr Ala Leu His
            20                  25

<210> SEQ ID NO 62
<211> LENGTH: 28
<212> TYPE: PRT
<213> ORGANISM: C. heterostrophus PKS1

<400> SEQUENCE: 62

Asn Arg Ile Ser Tyr Ser Phe Asp Leu Lys Gly Pro Ser Val Leu Val
1               5                   10                  15

Asp Thr Ala Cys Ser Gly Gly Leu Thr Ala Leu His
            20                  25

<210> SEQ ID NO 63
<211> LENGTH: 28
<212> TYPE: PRT
<213> ORGANISM: G. fujikuroi FUM5

<400> SEQUENCE: 63

Asn Arg Ile Ser Tyr Glu Tyr Asp Leu Lys Gly Pro Ser Phe Thr Ile
1               5                   10                  15

Lys Ala Gly Cys Ser Ser Ser Leu Ile Ala Leu His
            20                  25

```
<210> SEQ ID NO 64
<211> LENGTH: 26
<212> TYPE: PRT
<213> ORGANISM: A. terreus lovB

<400> SEQUENCE: 64

Arg Ile Arg Phe Thr Ala Val Val Gly His Ser Ser Gly Glu Ile Ala
1               5                   10                  15

Cys Ala Phe Ala Ala Gly Leu Ile Ser Ala
            20                  25

<210> SEQ ID NO 65
<211> LENGTH: 26
<212> TYPE: PRT
<213> ORGANISM: M. purpureus MkA

<400> SEQUENCE: 65

Gly Ile Gln Phe Ala Ala Val Val Gly His Ser Ser Gly Glu Ile Ala
1               5                   10                  15

Cys Ala Phe Ala Thr Gly Leu Ile Ser Ala
            20                  25

<210> SEQ ID NO 66
<211> LENGTH: 26
<212> TYPE: PRT
<213> ORGANISM: P. citrinum mlcA

<400> SEQUENCE: 66

Gly Ile Glu Phe Ser Ala Ile Val Gly His Ser Ser Gly Glu Ile Ala
1               5                   10                  15

Cys Ala Phe Ala Ala Gly Phe Ile Ser Ala
            20                  25

<210> SEQ ID NO 67
<211> LENGTH: 26
<212> TYPE: PRT
<213> ORGANISM: A. terreus lovF

<400> SEQUENCE: 67

Asn Ile Gln Pro Val Ala Val Thr Ser His Ser Ser Gly Glu Ala Ala
1               5                   10                  15

Ala Ala Tyr Ala Ile Gly Ala Leu Thr Ala
            20                  25

<210> SEQ ID NO 68
<211> LENGTH: 26
<212> TYPE: PRT
<213> ORGANISM: M. purpureus mkB

<400> SEQUENCE: 68

Gly Ile Arg Pro Ala Ala Ile Thr Ser His Ser Ser Gly Glu Val Ala
1               5                   10                  15

Ala Ala Tyr Ala Val Gly Ala Phe Ser Ala
            20                  25

<210> SEQ ID NO 69
<211> LENGTH: 26
<212> TYPE: PRT
<213> ORGANISM: P. citrinum mlcB

<400> SEQUENCE: 69

Gly Ile Arg Pro Thr Gly Ile Thr Ser His Ser Ser Gly Glu Ala Ala
1               5                   10                  15
```

```
Ala Ala Tyr Ala Ala Gly Ala Leu Ser Ala
            20                  25

<210> SEQ ID NO 70
<211> LENGTH: 26
<212> TYPE: PRT
<213> ORGANISM: C. heterostrophus PKS1

<400> SEQUENCE: 70

Gly Ile Tyr Ala Gln Ser Val Thr Ser His Ser Ser Gly Glu Ile Ala
1               5                   10                  15

Ala Ala Tyr Ala Ala Gly Ala Leu Ser Leu
            20                  25

<210> SEQ ID NO 71
<211> LENGTH: 26
<212> TYPE: PRT
<213> ORGANISM: G. fujikuroi FUM5

<400> SEQUENCE: 71

Gly Ile Thr Pro Ala Ala Val Val Gly His Ser Ser Gly Glu Met Ala
1               5                   10                  15

Ala Ala Tyr Ala Ala Gly Ala Ile Ser Ser
            20                  25

<210> SEQ ID NO 72
<211> LENGTH: 26
<212> TYPE: PRT
<213> ORGANISM: P. patulum MSAS

<400> SEQUENCE: 72

Gly Ile Thr Pro Gln Ala Val Ile Gly His Ser Val Gly Glu Ile Ala
1               5                   10                  15

Ala Ser Val Val Ala Gly Ala Leu Ser Pro
            20                  25

<210> SEQ ID NO 73
<211> LENGTH: 26
<212> TYPE: PRT
<213> ORGANISM: Rat FAS

<400> SEQUENCE: 73

Gly Leu Lys Pro Asp Gly Ile Ile Gly His Ser Leu Gly Glu Val Ala
1               5                   10                  15

Cys Gly Tyr Ala Asp Gly Cys Leu Ser Gln
            20                  25

<210> SEQ ID NO 74
<211> LENGTH: 26
<212> TYPE: PRT
<213> ORGANISM: A. terreus lovB

<400> SEQUENCE: 74

Arg Asp Ile Glu Trp Leu Asp Gly His Ala Leu Gln Gly Gln Thr Val
1               5                   10                  15

Phe Pro Ala Ala Gly Tyr Ile Val Met Ala
            20                  25

<210> SEQ ID NO 75
<211> LENGTH: 26
<212> TYPE: PRT
<213> ORGANISM: M. purpureus mkA
```

-continued

```
<400> SEQUENCE: 75

Arg Asp Ile Glu Trp Leu Asp Gly His Ala Leu Gln Gly Gln Val Val
1               5                   10                  15

Phe Pro Ala Ala Gly Tyr Ile Val Met Ala
            20                  25

<210> SEQ ID NO 76
<211> LENGTH: 26
<212> TYPE: PRT
<213> ORGANISM: P. citrinum mlcA

<400> SEQUENCE: 76

Arg Asp Leu Glu Trp Leu Asp Gly His Ala Leu Gln Gly Gln Thr Val
1               5                   10                  15

Phe Pro Ala Ala Gly Tyr Ile Ile Met Ala
            20                  25

<210> SEQ ID NO 77
<211> LENGTH: 26
<212> TYPE: PRT
<213> ORGANISM: P. patulum MSAS

<400> SEQUENCE: 77

Asp Thr Lys Pro Phe Pro Gly Ser His Pro Leu His Gly Thr Glu Ile
1               5                   10                  15

Val Pro Ala Ala Gly Leu Ile Asn Thr Phe
            20                  25

<210> SEQ ID NO 78
<211> LENGTH: 26
<212> TYPE: PRT
<213> ORGANISM: A. terreus lovF

<400> SEQUENCE: 78

Ser Asp Leu Pro Trp Leu Arg Asp His Val Val Gly Ser His Ile Val
1               5                   10                  15

Phe Pro Gly Ala Gly Phe Val Cys Met Ala
            20                  25

<210> SEQ ID NO 79
<211> LENGTH: 26
<212> TYPE: PRT
<213> ORGANISM: M. purpureus mkB

<400> SEQUENCE: 79

Ser Asp Val Pro Trp Ile Arg Asp His Val Val Gly Ser Arg Ile Leu
1               5                   10                  15

Phe Pro Gly Ala Gly Phe Ile Ser Met Val
            20                  25

<210> SEQ ID NO 80
<211> LENGTH: 26
<212> TYPE: PRT
<213> ORGANISM: P. citrinum mlcB

<400> SEQUENCE: 80

Ser Asp Ile Pro Trp Ile Arg Asp His Val Val Gly Ser Ser Ile Ile
1               5                   10                  15

Phe Pro Gly Ala Gly Phe Ile Ser Met Ala
            20                  25
```

```
<210> SEQ ID NO 81
<211> LENGTH: 26
<212> TYPE: PRT
<213> ORGANISM: C. heterostrophus PKS1

<400> SEQUENCE: 81

Ser Glu Leu Pro Trp Leu Gln Asp His Lys Ile Gln Ser Ser Ile Leu
1               5                   10                  15

Tyr Pro Val Ala Gly Tyr Ile Ala Met Ala
            20                  25

<210> SEQ ID NO 82
<211> LENGTH: 26
<212> TYPE: PRT
<213> ORGANISM: G. fujikuroi FUM5

<400> SEQUENCE: 82

Asp Gly Ile Pro Trp Leu Arg Asp His Gln Val Leu Asn Asp Val Val
1               5                   10                  15

Phe Pro Cys Ala Gly Tyr Leu Ala Met Ala
            20                  25

<210> SEQ ID NO 83
<211> LENGTH: 26
<212> TYPE: PRT
<213> ORGANISM: Rat FAS

<400> SEQUENCE: 83

Ser Ser Asp His Tyr Leu Val Asp His Cys Ile Asp Gly Arg Val Leu
1               5                   10                  15

Phe Pro Gly Thr Gly Tyr Leu Tyr Leu Val
            20                  25

<210> SEQ ID NO 84
<211> LENGTH: 14
<212> TYPE: PRT
<213> ORGANISM: A. terreus lovB

<400> SEQUENCE: 84

Asp Ile Leu Glu Ile Gly Ala Gly Thr Gly Gly Ala Thr Lys
1               5                   10

<210> SEQ ID NO 85
<211> LENGTH: 14
<212> TYPE: PRT
<213> ORGANISM: A. terreus lovF

<400> SEQUENCE: 85

Arg Ile Leu Glu Ile Gly Gly Gly Thr Gly Gly Cys Thr Gln
1               5                   10

<210> SEQ ID NO 86
<211> LENGTH: 14
<212> TYPE: PRT
<213> ORGANISM: P. citrinum mlcB

<400> SEQUENCE: 86

Arg Ile Leu Glu Ile Gly Gly Gly Thr Gly Gly Cys Thr Lys
1               5                   10

<210> SEQ ID NO 87
<211> LENGTH: 14
<212> TYPE: PRT
```

-continued

<213> ORGANISM: P. citrinum mlcA

<400> SEQUENCE: 87

Asp Ile Leu Glu Ile Gly Leu Gly Thr Gly Ile Ala Thr Lys
1               5                   10

<210> SEQ ID NO 88
<211> LENGTH: 20
<212> TYPE: PRT
<213> ORGANISM: A. terreus lovF

<400> SEQUENCE: 88

Ile Leu Pro Gly Glu Thr Val Leu Ile His Ala Gly Ala Gly Gly Val
1               5                   10                  15

Gly Gln Ala Ala
        20

<210> SEQ ID NO 89
<211> LENGTH: 20
<212> TYPE: PRT
<213> ORGANISM: M. purpureus mkB

<400> SEQUENCE: 89

Leu Gln Arg Gly Glu Lys Val Leu Ile His Gly Gly Ala Gly Gly Val
1               5                   10                  15

Gly Gln Ala Ala
        20

<210> SEQ ID NO 90
<211> LENGTH: 20
<212> TYPE: PRT
<213> ORGANISM: P. citrinum mlcB

<400> SEQUENCE: 90

Leu Arg Arg Gly Glu Arg Val Leu Ile His Ser Gly Ala Gly Gly Val
1               5                   10                  15

Gly Gln Ala Ala
        20

<210> SEQ ID NO 91
<211> LENGTH: 20
<212> TYPE: PRT
<213> ORGANISM: C. geterostrophus PKS1

<400> SEQUENCE: 91

Leu Arg His Gly Glu Thr Ile Leu Ile His Ala Ala Ala Gly Gly Leu
1               5                   10                  15

Gly Gln Ala Leu
        20

<210> SEQ ID NO 92
<211> LENGTH: 20
<212> TYPE: PRT
<213> ORGANISM: G. fujikuroi FUM5

<400> SEQUENCE: 92

Leu Arg Pro Gly Gln Ser Ile Leu Ile His Ser Ala Cys Gly Gly Ile
1               5                   10                  15

Gly Ile Ala Ala
        20

<210> SEQ ID NO 93

```
<211> LENGTH: 20
<212> TYPE: PRT
<213> ORGANISM: Rat FAS

<400> SEQUENCE: 93

Ile Gln His Gly Glu Thr Val Leu Ile His Ser Gly Ser Gly Gly Val
1               5                   10                  15

Gly Gln Ala Ala
            20

<210> SEQ ID NO 94
<211> LENGTH: 32
<212> TYPE: PRT
<213> ORGANISM: A. terreus lovB

<400> SEQUENCE: 94

Thr Tyr Leu Leu Val Gly Leu Thr Gly Asp Leu Gly Arg Ser Leu Gly
1               5                   10                  15

Arg Trp Met Val Gln His Gly Ala Cys His Ile Val Leu Thr Ser Arg
            20                  25                  30

<210> SEQ ID NO 95
<211> LENGTH: 32
<212> TYPE: PRT
<213> ORGANISM: M. purpureus mkA

<400> SEQUENCE: 95

Thr Tyr Leu Leu Val Gly Leu Thr Gly Asp Leu Gly Arg Ser Leu Gly
1               5                   10                  15

Arg Trp Met Val Leu His Gly Ala Arg Arg Ile Val Leu Thr Ser Arg
            20                  25                  30

<210> SEQ ID NO 96
<211> LENGTH: 32
<212> TYPE: PRT
<213> ORGANISM: P. citrinum mlcA

<400> SEQUENCE: 96

Thr Tyr Leu Leu Val Gly Leu Thr Gly Asp Leu Gly Arg Ser Leu Cys
1               5                   10                  15

Arg Trp Met Ile Leu His Gly Ala Arg His Val Val Leu Thr Ser Arg
            20                  25                  30

<210> SEQ ID NO 97
<211> LENGTH: 32
<212> TYPE: PRT
<213> ORGANISM: P. patulum MSAS

<400> SEQUENCE: 97

Thr Tyr Leu Ile Thr Gly Gly Leu Gly Val Leu Gly Leu Glu Val Ala
1               5                   10                  15

Asp Phe Leu Val Glu Lys Gly Ala Arg Arg Leu Leu Leu Ile Ser Arg
            20                  25                  30

<210> SEQ ID NO 98
<211> LENGTH: 32
<212> TYPE: PRT
<213> ORGANISM: Rat FAS

<400> SEQUENCE: 98

Ser Tyr Ile Ile Thr Gly Gly Leu Gly Gly Phe Gly Leu Glu Leu Ala
1               5                   10                  15
```

-continued

```
Arg Trp Leu Val Leu Arg Gly Ala Gln Arg Leu Val Leu Thr Ser Arg
            20                  25                  30

<210> SEQ ID NO 99
<211> LENGTH: 32
<212> TYPE: PRT
<213> ORGANISM: A. terreus lovF

<400> SEQUENCE: 99

Ser Tyr Leu Val Ala Gly Gly Leu Gly Gly Ile Gly Arg Arg Ile Cys
1               5                   10                  15

Glu Trp Leu Val Asp Arg Gly Ala Arg Tyr Leu Ile Ile Leu Ser Arg
            20                  25                  30

<210> SEQ ID NO 100
<211> LENGTH: 32
<212> TYPE: PRT
<213> ORGANISM: M. purpureus mkB

<400> SEQUENCE: 100

Ser Tyr Leu Ile Val Gly Gly Leu Gly Gly Ile Gly Arg Arg Ile Cys
1               5                   10                  15

Glu Trp Met Val Asp His Gly Ala Arg His Leu Leu Ile Leu Ser Arg
            20                  25                  30

<210> SEQ ID NO 101
<211> LENGTH: 32
<212> TYPE: PRT
<213> ORGANISM: P. citrinum mlcB

<400> SEQUENCE: 101

Ser Tyr Leu Val Ala Gly Gly Leu Gly Gly Ile Gly Lys Gln Ile Cys
1               5                   10                  15

Gln Trp Leu Val Asp His Gly Ala Lys His Leu Ile Ile Leu Ser Arg
            20                  25                  30

<210> SEQ ID NO 102
<211> LENGTH: 32
<212> TYPE: PRT
<213> ORGANISM: C. geterostrophus PKS1

<400> SEQUENCE: 102

Ser Tyr Leu Leu Val Gly Gly Val Gly Gly Leu Gly Ser Ala Thr Ala
1               5                   10                  15

Leu Trp Met Ser Thr Arg Gly Ala Arg His Leu Leu Leu Leu Asn Arg
            20                  25                  30

<210> SEQ ID NO 103
<211> LENGTH: 32
<212> TYPE: PRT
<213> ORGANISM: G. fujikuroi FUM5

<400> SEQUENCE: 103

Ser Tyr Leu Leu Val Gly Gly Leu Gly Gly Leu Gly Arg Ala Ala Ala
1               5                   10                  15

Thr Trp Met Val Glu Ser Gly Ala Arg Tyr Leu Ile Phe Phe Ser Arg
            20                  25                  30

<210> SEQ ID NO 104
<211> LENGTH: 21
<212> TYPE: PRT
<213> ORGANISM: A. terreus lovB
```

```
<400> SEQUENCE: 104

Thr Ile Pro Leu Ile Asp Gln Gly Val Asp Ser Leu Gly Ala Val Thr
1               5                   10                  15

Val Gly Thr Trp Phe
            20

<210> SEQ ID NO 105
<211> LENGTH: 21
<212> TYPE: PRT
<213> ORGANISM: P. patulum MSAS

<400> SEQUENCE: 105

Lys Ala Ala Leu Ala Asp Leu Gly Val Asp Ser Val Met Thr Val Thr
1               5                   10                  15

Leu Arg Arg Gln Leu
            20

<210> SEQ ID NO 106
<211> LENGTH: 21
<212> TYPE: PRT
<213> ORGANISM: Rat FAS

<400> SEQUENCE: 106

Asp Ser Ser Leu Ala Asp Leu Gly Leu Asp Ser Leu Met Gly Val Glu
1               5                   10                  15

Val Arg Gln Ile Leu
            20

<210> SEQ ID NO 107
<211> LENGTH: 21
<212> TYPE: PRT
<213> ORGANISM: A. terreus lovF

<400> SEQUENCE: 107

Thr Gln Thr Leu Ala Gly Ile Gly Val Asp Ser Leu Val Ala Ile Glu
1               5                   10                  15

Leu Arg Asn Trp Ile
            20

<210> SEQ ID NO 108
<211> LENGTH: 21
<212> TYPE: PRT
<213> ORGANISM: M. purpureus mkB

<400> SEQUENCE: 108

Thr Gln Thr Leu Ser Ser Val Gly Val Asp Ser Leu Val Ala Ile Glu
1               5                   10                  15

Leu Arg Asn Trp Ile
            20

<210> SEQ ID NO 109
<211> LENGTH: 21
<212> TYPE: PRT
<213> ORGANISM: P. citrinum mlcB

<400> SEQUENCE: 109

Ser Lys Asn Leu Ala Gly Val Gly Val Asp Ser Leu Val Ala Ile Glu
1               5                   10                  15

Leu Arg Asn Trp Ile
            20
```

-continued

```
<210> SEQ ID NO 110
<211> LENGTH: 21
<212> TYPE: PRT
<213> ORGANISM: C. geterostrophus PKS1

<400> SEQUENCE: 110

Thr Lys Ser Leu Gln Asp Tyr Gly Ile Asp Ser Leu Val Ala Val Glu
1               5                   10                  15

Leu Arg Asn Trp Leu
            20

<210> SEQ ID NO 111
<211> LENGTH: 21
<212> TYPE: PRT
<213> ORGANISM: G. fujikuroi FUM5

<400> SEQUENCE: 111

Thr Ala Ser Leu Thr Ser Leu Gly Val Asp Ser Leu Val Thr Ile Glu
1               5                   10                  15

Ile Arg Asn Trp Ile
            20

<210> SEQ ID NO 112
<211> LENGTH: 14
<212> TYPE: PRT
<213> ORGANISM: M. purpureus mkB

<400> SEQUENCE: 112

Arg Ile Leu Glu Ile Gly Gly Gly Thr Gly Gly Cys Thr Gln
1               5                   10

<210> SEQ ID NO 113
<211> LENGTH: 14
<212> TYPE: PRT
<213> ORGANISM: M. purpureus mkA

<400> SEQUENCE: 113

Asp Ile Leu Glu Ile Gly Ala Gly Thr Gly Gly Ala Thr Lys
1               5                   10

<210> SEQ ID NO 114
<211> LENGTH: 21
<212> TYPE: PRT
<213> ORGANISM: M. purpureus mkA

<400> SEQUENCE: 114

Thr Ile Pro Leu Ile Asp Gln Gly Val Asp Ser Leu Gly Ala Val Thr
1               5                   10                  15

Val Gly Thr Trp Phe
            20

<210> SEQ ID NO 115
<211> LENGTH: 21
<212> TYPE: PRT
<213> ORGANISM: P. citrinum mlcA

<400> SEQUENCE: 115

Thr Ile Pro Leu Ile Asp Gln Gly Val Asp Ser Leu Gly Ala Val Thr
1               5                   10                  15

Val Gly Ser Trp Phe
            20

<210> SEQ ID NO 116
```

```
<211> LENGTH: 28
<212> TYPE: PRT
<213> ORGANISM: M. purpureus mkA

<400> SEQUENCE: 116

Asn Arg Ile Ser Tyr Phe Phe Asp Trp His Gly Pro Ser Met Thr Ile
1               5                   10                  15

Asp Thr Ala Cys Ser Ser Ser Leu Val Ala Val His
            20                  25

<210> SEQ ID NO 117
<211> LENGTH: 455
<212> TYPE: PRT
<213> ORGANISM: Monascus

<400> SEQUENCE: 117

Met Ala Leu Ser Pro Val Gln Asp Pro Pro Ser His Thr Asp Lys Thr
1               5                   10                  15

Met Pro Arg Arg Ala Phe Arg Arg Ser Cys Asp Arg Cys His Ala Gln
            20                  25                  30

Lys Ile Lys Cys Ile Gly Ser Glu Gly Ala Val Ala Arg Ala Ser Cys
        35                  40                  45

Gln Arg Cys Gln Gln Ala Gly Leu Arg Cys Val Tyr Ser Glu Arg Cys
    50                  55                  60

Pro Lys Arg Lys Leu Pro Lys Pro Asn Pro Ala Glu Ser Ser Pro Ala
65                  70                  75                  80

Ser Ser Thr Ala Gly Leu His Thr Ser Ser Asp Ser Ser Pro Pro
                85                  90                  95

Val Pro Ser Asp Gly Leu Pro Leu Asp Leu Pro Gly Pro Asp Ser Ser
                100                 105                 110

Gly Val Ser Leu Gln Phe Leu Asp Pro Ser Ala Asp Cys Asp Trp Pro
            115                 120                 125

Trp Ser Ser Ile Gly Val Asp Glu Thr Val Val Asn Asn Cys Leu Asp
    130                 135                 140

Leu Ser His Gly His Gly His Gly Asp Leu Ser Cys Gln Leu Glu Leu
145                 150                 155                 160

Pro Met Pro Asp Leu Pro Ser Pro Phe Glu Phe Ser Ala Glu Lys Ser
                165                 170                 175

Pro Ser Pro Ser Val Ser Gly Ser Ile Ala Gly Ala Val Ser Ala Gln
            180                 185                 190

Arg Glu Leu Phe Asp Gly Leu Ser Thr Val Ser Gln Glu Leu Glu Ala
        195                 200                 205

Ile Leu Leu Ala Val Ala Val Glu Trp Pro Lys Gln Glu Ile Trp Thr
    210                 215                 220

Tyr Pro Ile Gly Thr Phe Phe Asn Ala Ser Arg Arg Leu Leu Val Tyr
225                 230                 235                 240

Leu Gln Gln Gln Ser Asn Thr Arg Ser Asp Gln Gly Met Leu Asn Glu
                245                 250                 255

Cys Leu Arg Thr Lys Asn Leu Phe Met Ala Val His Cys Tyr Met Leu
            260                 265                 270

Ile Val Lys Ile Phe Thr Ser Leu Ser Glu Leu Leu Leu Ser Gln Ile
        275                 280                 285

Arg His Ser Gln Ala Gly Gln Leu Thr Pro Leu Glu Gly His Gln Phe
    290                 295                 300

Glu Pro Pro Pro Ser Ser Ser Arg Asp Arg Ser Ser Val Asp Thr Met
305                 310                 315                 320
```

-continued

```
Pro Ile Phe Asn Pro Asn Leu His Ile Gly Gly Leu Phe Ser Tyr Leu
            325             330             335

Asn Pro Phe Met His Ala Leu Ser Ser Ala Cys Thr Thr Leu Arg Val
            340             345             350

Gly Val Gln Leu Leu Arg Glu Asn Glu Ser Ala Leu Gly Ile Pro Pro
        355             360             365

Ala Gln Gly Val Ala Ala Ser Val Ser Met Gly Lys Glu Glu Trp Ala
    370             375             380

Asp Gly Glu Asp Val Ala Ser Ala Val Thr Thr Ala Asp Glu Asp Leu
385             390             395             400

Arg Gln Pro Ala Ser Arg Ile Leu Ser Met Val Trp Ser Asp Glu Val
            405             410             415

Gly Asp Gln Lys Ala Lys Ser Ala Asp Ala Ala Gly Pro Arg Ser Arg
            420             425             430

Thr Leu Ala Val Leu Arg Arg Cys Asn Arg Glu Ile Phe Ser Leu Ala
        435             440             445

Arg Gln His Asn Leu Ala Ser
    450             455
```

MONACOLIN K BIOSYNTHESIS GENES

BACKGROUND

The invention relates to the field of molecular biology and microbiology. More particularly, the invention relates to monacolin K biosynthesis genes.

*Monascus* has been applied in the food industry for thousands of years in China. Recently, it was discovered that *Monascus* produces several bioactive substances. These bioactive substances are mainly the secondary metabolites of *Monascus*, including substances for reducing hypertension, substances of anti-putrefaction bacteria such as monascidin, anti-cancer substances, substances for lowering blood sugar, ergosteral, anti-oxidants, and inhibitors of cholesterol synthesis such as monacolin. Therefore, *Monascus* has been valued as a functional health food in recent years.

Monacolin K, the cholesterol-synthesis inhibitor produced by *Monascus*, was first isolated from the medium of *Monascus* rubber by SANKYO CO., LTD. Merck & Co., Inc. then found the same substance from the medium of *Aspergillus terreus* denominated as lovastatin and acted as a HMG-COA reductase inhibitor. Monacolin K belongs to polyketides and the structure thereof shares similarity with HMG-CoA. Therefore, Monacolin K competitively inhibits cholesterol synthesis with HMG-CoA, and HMG-CoA reductase cannot catalyze HMG-CoA to form mevolonate, resulting in reduction of cholesterol synthesis.

The secondary metabolites of polyketides produced by fungi express structural variety and unique characteristics which do not exist in other bacteria (O'Hagan, 1995). These characteristics are also expressed in enzyme variety of polyketide synthesis. Monacolin K produced by *Monascus* is a member of the polyketide group, and it is found that the various polyketides are produced by condensation of acetyl CoA catalyzed by polyketide synthase (PKS) (Kennedy et al., 1999; and Abe et al., 2002). From the study of polyketide synthase combined with combinatorial biosynthesis, the development of novel polyketides has great potential (Mc Daniel et al., 1999), and the novel polyketides will be another new rout for screening effective medications.

SUMMARY

Accordingly, an embodiment of the invention provides an isolated DNA molecule, comprising a nucleotide sequence of SEQ ID NO: 1 or a nucleotide sequence hybridizable thereto under stringent conditions.

Another embodiment of the invention provides an isolated DNA molecule comprising a polynucleotide selected from a group consisting of: a) a polynucleotide which is mkA and comprises a nucleotide sequence of SEQ ID NO: 2, b) a polynucleotide which is mkB and comprises a nucleotide sequence of SEQ ID NO: 3, c) a polynucleotide which is mkC and comprises a nucleotide sequence of SEQ ID NO: 4, d) a polynucleotide which is mkD and comprises a nucleotide sequence of SEQ ID NO: 5, e) a polynucleotide which is mkE and comprises a nucleotide sequence of SEQ ID NO: 6, f) a polynucleotide which is mkF and comprises a nucleotide sequence of SEQ ID NO: 7, g) a polynucleotide which is mkG and comprises a nucleotide sequence of SEQ ID NO: 8, h) a polynucleotide which is mkH and comprises a nucleotide sequence of SEQ ID NO: 9, i) a polynucleotide which is mkI and comprises a nucleotide sequence of SEQ ID NO: 10, and j) a polynucleotide hybridizable to the polynucleotide from a), b), c), d), e), f), g), h), or i) under stringent conditions.

Yet another embodiment of the invention provides an vector comprising the isolated DNA molecule as above defined.

In addition, an embodiment of the invention provides a cell transformed with an vector comprising a polynucleotide selected from a group consisting of: a) a polynucleotide which is mkA and comprises a nucleotide sequence of SEQ ID NO: 2, b) a polynucleotide which is mkB and comprises a nucleotide sequence of SEQ ID NO: 3, c) a polynucleotide which is mkC and comprises a nucleotide sequence of SEQ ID NO: 4, d) a polynucleotide which is mkD and comprises a nucleotide sequence of SEQ ID NO: 5, e) a polynucleotide which is mkE and comprises a nucleotide sequence of SEQ ID NO: 6, f) a polynucleotide which is mkF and comprises a nucleotide sequence of SEQ ID NO: 7, g) a polynucleotide which is mkG and comprises a nucleotide sequence of SEQ ID NO-8, h) a polynucleotide which is mkH and comprises a nucleotide sequence of SEQ ID NO: 9, i) a polynucleotide which is mkI and comprises a nucleotide sequence of SEQ ID NO: 10, and j) the combination thereof.

Moreover, an embodiment of the invention provides a method for increasing monacolin K production, comprising culturing a cell transformed by an vector, and collecting monacolin K from the cell. The vector comprising a polynucleotide selected from a group consisting of: a) a polynucleotide which is mkA and comprises a nucleotide sequence of SEQ ID NO: 2, b) a polynucleotide which is mkB and comprises a nucleotide sequence of SEQ ID NO: 3, c) a polynucleotide which is mkC and comprises a nucleotide sequence of SEQ ID NO: 4, d) a polynucleotide which is mkD and comprises a nucleotide sequence of SEQ ID NO: 5, e) a polynucleotide which is mkE and comprises a nucleotide sequence of SEQ ID NO: 6, f) a polynucleotide which is mkF and comprises a nucleotide sequence of SEQ ID NO: 7, g) a polynucleotide which is mkH and comprises a nucleotide sequence of SEQ ID NO: 9, and h) the combination thereof.

Moreover, an embodiment of the invention provides a method for increasing HMG-CoA reductase inhibitor production, comprising culturing a cell transformed by a vector, and collecting HMG-CoA reductase inhibitor from the cell. The vector is as above defined.

Furthermore, an embodiment of the invention provides a method of the production of HMG-CoA reductase inhibitor. The method comprises the steps of: (a) transforming a nucleotide sequence of SEQ ID NO: 2 (mkA genomic DNA), SEQ ID NO: 3 (mkB genomic DNA), SEQ ID NO: 6 (mkE genomic DNA), and SEQ ID NO: 7 (mkF genomic DNA), or a nucleotide sequence sharing 95% homology with these sequences, or a nucleotide sequence hybridizable to these sequences under stringent conditions into a host cell, wherein these sequences encode proteins having nonaketide synthase, diketide synthase, dehydrogenase, and transesterase activity respectively; (b) culturing the transformed cell under a condition suitable for the expression of the nucleotide sequences; and (c) collecting HMG-CoA reductase inhibitor.

Furthermore, an embodiment of the invention provides a method of the production of monacolin k, comprising culturing a cell transformed by a vector and collecting monacolin k from the cell. The vector is as above defined.

BRIEF DESCRIPTION OF THE DRAWINGS

Embodiments of the invention can be more fully understood and further advantages become apparent when reference is made to the following description and the accompanying drawings in which:

FIG. 1A~1G illustrate sequence comparison of polyketide synthase from *Monascus* or other fungi, and motif of fatty acid synthase from rat. FIG. 1A shows ketoacyl synthase comparison, FIG. 1B shows acyl transferase comparison, FIG. 1C shows dehydratase comparison, FIG. 1D shows methyl transferase comparison, FIG. 1E shows enoyl reductase comparison, FIG. 1F shows ketoacyl reductase comparison, and FIG. 1G shows acyl carry protein comparison.

DETAILED DESCRIPTION

Figure 2:
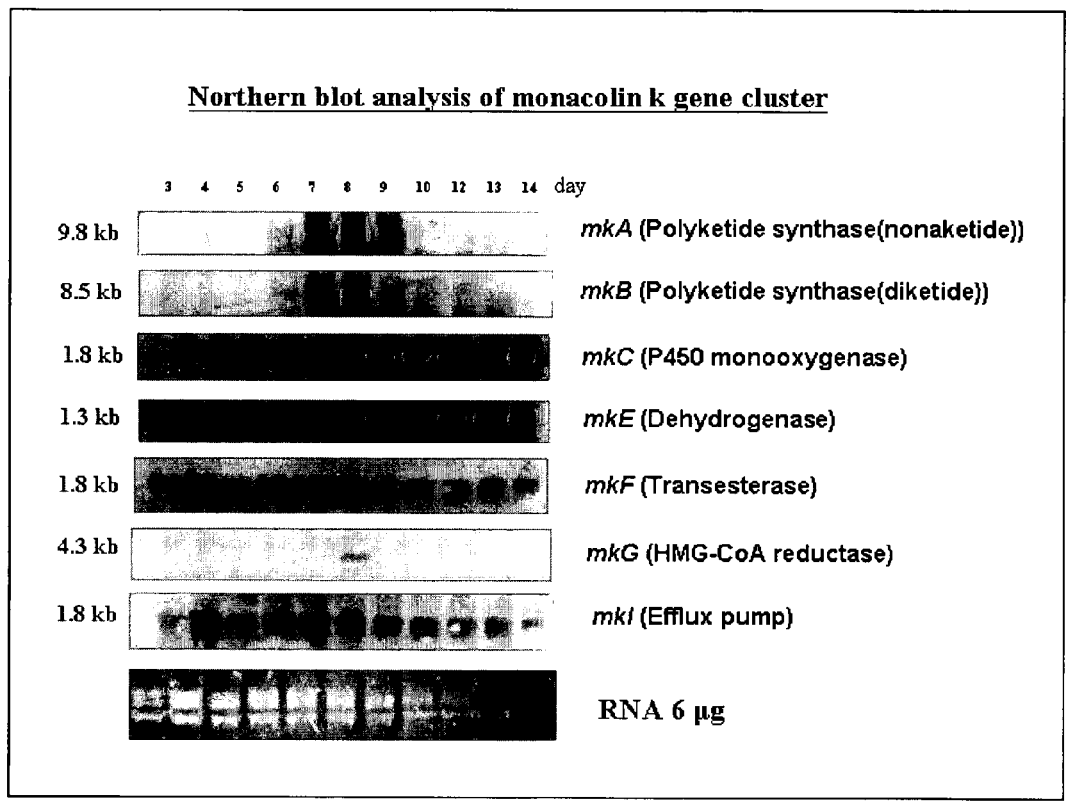
FIG. 2 illustrates expression of *Monascus* mk gene cluster at 3~14 days.

Probes specific to *Monascus* were designed according to the degenerate primers to lovastatin of *Aspergillus terreus* published by Nicholson (2001). The genes related to monacolin K synthesis were cloned from *Monascus* BAC library by colony hybridization, sequenced, and annotated. Two PKS full-length cDNAs were amplified by RT-PCR and cloned into expression vectors respectively. The invention was then achieved.

Since the discovery of cholesterol inhibitors produced by *Monascus* in the 1980's, increasing interest has been focused on the effect of *Monascus* in lowering blood pressure, blood sugar, and cholesterol. In spite of monacolin K, other substances for lowering cholesterol were isolated from *Monascus*, for example, monacolin J, L, M, and X (Endo et al., 1979, 1985, 1986, and Komagata et al., 1989). Monacolin J and L are precursors of monacolin K. The mechanism of cholesterol-synthesis inhibition by Monacolin K is based on the structural similarities between monacolin k and HMG-CoA. Monacolin k may bind to HMG-CoA reductase and block its catalysis activity for the formation of mevolonate from HMG-CoA, and cholesterol synthesis will then be greatly reduced. Except for monacolin K, other methods adopting biotransformation or chemical modification for the inhibition of cholesterol are also commercially available, for example, Pravastatin, Simvastatin, Fluvastatin, or Atorvastatin, which all share structural similarities with HMG-CoA.

Therefore, the primary object of the invention is to provide genes related to monacolin K production from *Monascus*. The subject analyzed in the invention is *Monascus* sp. BCRC 38072 which was observed as having the characteristics of:

Macroscopic Characteristics:

CYA, 25° C., 7 days. Colonies 25-26 mm diam, mycelium white initially, becoming light reddish orange, reverse deep reddish orange.

MEA, 25° C., 7 days. Colonies 48 mm diam, bright reddish orange, reverse vivid reddish orange.

G25N, 25° C., 7 days. Colonies 28-29 mm diam, deep reddish orange, deep yellowish orange at the centers.

Microscopic Characteristics:

Aleurioconidia arising singly or occasionally in short chains, obpyriform to globose, 10-13×8-10 μm. Cleistothecia globose, 37-72 μm diam. Ascospores hyaline, ellipsoid, 4.6-6.3 (−6.6)×3.3-4.2 μm.

According to the classification system of Hawksworth & Pitt (1983), BCRC 38072 was identified as:

Morphological Characteristics:

BCRC 38072 is between *M. pilosus* and *M. ruber*.

1. BCRC 38072 is similar to *M. pilosus* in colony color and growth rate.

2. BCRC 38072 is similar to *M. ruber* in the morphology of ascospore.

Sequence Analysis:

BCRC 38072, *M. ruber*, and *M pilosus* share 100% sequence similarity in rDNA ITS fragments and β-tubulin gene.

Species Identification:

BCRC 38072 was temporarily denominated as *Monascus pilosus* K. Sato ex D. Hawksw. & Pitt.

From the analysis of *Monascus pilosus* BCRC 38072, probes specific to the conserved region of ketosynthase with a length of 226 bp (SEQ ID NO: 1) were designed for colony hybridization, southern blotting, and PCR. In addition, the probes can be used for *Monascus* screening. The annotation and prediction of the full-length BAC DNA sequence was performed by BLAST and Vector NTI. Nine genes sharing high similarities of over 54% with lovastatin gene cluster produced by *Aspergillus terreus* were obtained by the BAC library, as shown in table 1.

TABLE 1

Similarity comparison of mk gene cluster of Monascus, lov gene cluster of *Aspergillus terreus*, and mlc gene cluster of *Penicillium citrinum*.

| mk gene | Amino acids | Molecular weight (kDa) | Proposed function | Homologous lov gene | Protein similarity (%) | Homologous mlc gene | Protein similarity (%) |
| --- | --- | --- | --- | --- | --- | --- | --- |
| mkA | 3075 | 338 | polyketide synthase | lovB | 76 | mlcA | 66 |
| mkB | 2547 | 276 | polyketide synthase | lovF | 73 | mlcB | 61 |

TABLE 1-continued

Similarity comparison of mk gene cluster of Monascus, lov gene cluster of *Aspergillus terreus*, and mlc gene cluster of *Penicillium citrinum*.

| mk gene | Amino acids | Molecular weight (kDa) | Proposed function | Homologous lov gene | Protein similarity (%) | Homologous mlc gene | Protein similarity (%) |
|---------|-------------|------------------------|-------------------|---------------------|------------------------|---------------------|------------------------|
| mkC | 524 | 60.6 | P450 monooxygenase | lovA | 85 | mlcC | 67 |
| mkD | 263 | 28.9 | Oxidoreductase | lovG | 67 | mlcF | 53 |
| mkE | 360 | 38.9 | Dehydrogenase | lovC | 81 | mlcG | 70 |
| mkF | 413 | 46.8 | Transesterase | lovD | 74 | mlcH | 63 |
| mkG | 1052 | 113 | HMG-CoA reductase | lvrA | 69 | mlcD | 39 |
| mkH | 455 | 49.4 | Transcription factor | lovE | 54 | mlcR | 49 |
| mkI | 543 | 57.5 | Efflux pump | lovI | 81 | mlcE | 68 |

Monacolin K gene cluster and compactin gene cluster synthesized from *Penicillin citrinum* share high similarities of over 49%. The nine genes include two polyketide synthase genes, one is responsible for nonaketide synthesis, and the other is for diketide synthesis. Moreover, a monooxygenase gene, an oxidoreductase gene, a dehydrogenase gene, a trans esterase gene, an HMG-CoA reductase gene, a transcription factor gene, and an efflux pump gene are included. A fosmid library of *Monascus* was constructed and two clones which were screened by fosmid end sequence comparison were deposited for patent depository as pMPF001 including mkB, mkD, mkE, mkF, mkG, mkH; and pMPF002 including mkA, mkC, mkD, mkE, mkF, mkG, mkH, and mkI. pMPF001 was deposited in the American Type Culture Collection (ATCC) as PTA-5685, and pMPF002 was as PTA-5686. The functional regions of nonaketide synthase gene and diketide synthase gene were further analyzed by comparing with known polyketide synthesis genes of *Aspergillus, Penicillium, Cochliobolus*, and *Gibberella*, and fatty acid synthesis (FAS) genes of rat. The results indicate that the functional regions of these two genes are similar to that of lovastatin produced by *Aspergillus terreus* and compactin produced by *Penicillium citrinum*, as shown in FIG. 1. Northern blot analysis of total RNA extracted from *Monascus* shows the expression of these genes in transcriptional level, as shown in FIG. 2.

Figure 3A:
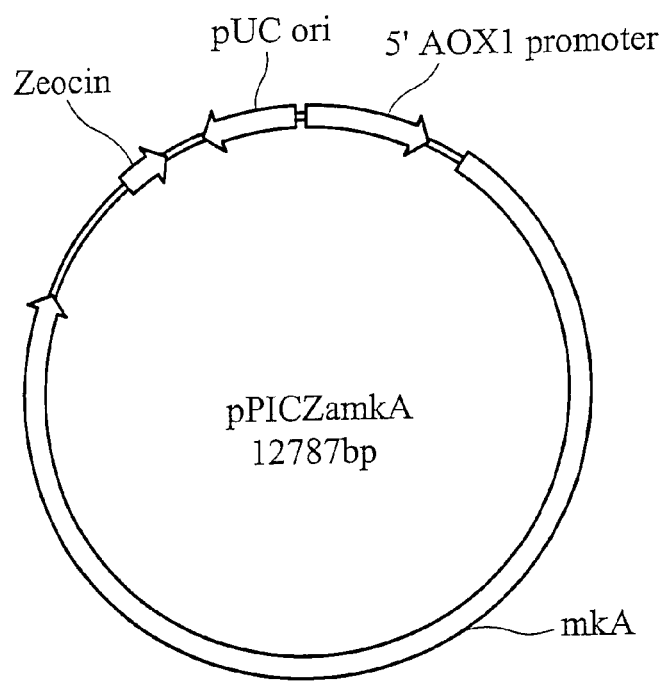
FIGS. 3A and 3B illustrate maps of pPICZamkA and pPICZamkB respectively.
Figure 3B:
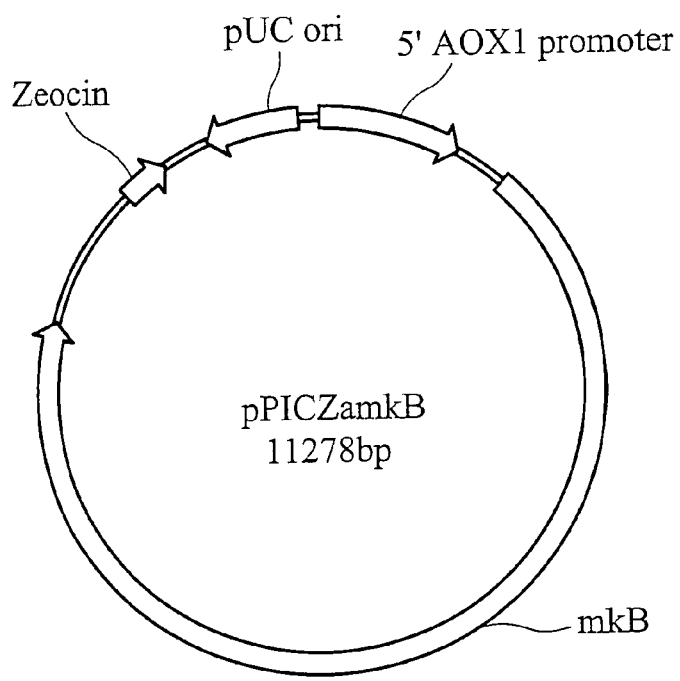

The two polyketide synthase genes of the invention are multi-functional enzymes: mkA gene has functionality of β-ketoacyl synthase, acetyl transferase, dehydratase, methyltransferase, ketoreductase, and acyl carrier protein; mkB gene has the above mentioned 6 functions and an additional enoyl reductase function, as shown in FIG. 1. Full-length cDNA of the two genes were obtained by RT-PCR and then cloned to the *Pichia pastoris* expression system for the expression of polyketide products. Since polyketide synthase gene expresses multi-functional enzymes, various polyketide products can be produced by DNA recombination such as shuffling from the full-length cDNA of the invention. This method is a new route for screening new drugs. Several patents such as U.S. Pat. Nos. 6,221,641 and 6,391,594 disclose similar methods for the expression in bacteria. However, the secondary metabolites of polyketides produced by fungi represent structural variety and complexity. Therefore, pPICZamkA (FIG. 3A) and pPICZamkB (FIG. 3B) obtained in the invention can be used as expression plasmids for expressing various polyketide products by shuffling.

Accordingly, the invention provides the following DNA molecules, vectors, and methods.

(I) Probes for Screening Genes Related to Monacolin K Synthesis

The invention features a probe for screening genes related to monacolin K synthesis, comprising a nucleotide sequence of SEQ ID NO: 1. The probe is specific to *Monascus* BCRC38072 and was designed from the degenerate primers for lovastatin synthesis gene of *Aspergillus terreus* designed by Nicoholson (2001). It is easy for those skilled in the art to isolate or purify genes similar to monacolin K by known methods such as hybridization using the probe of the invention.

(II) Nonaketide Synthase (mkA Genomic DNA)

One aspect of the invention relates to a DNA sequence comprising a nucleotide sequence of SEQ ID NO: 2 (mkA genomic DNA), or a nucleotide sequence sharing 95% homology with SEQ ID NO: 2, or a nucleotide sequence hybridizable thereto under stringent conditions and encoding a protein having nonaketide synthase activity. The DNA sequence was isolated from BCRC38072. In addition, the DNA sequence of the invention is obtainable for those skilled in the art by known methods such as PCR or hybridization according to the disclosure of the invention. References to the stringent conditions can be found in EP 1,325,959 A1 P7 [0036]. Nonaketide synthase catalyzes one acetate and eight malonates to form nonaketide. This gene has multi-functional regions, including β-ketoacyl synthase, acetyltransferase, dehydratase, methyltransferase, ketoreductase, and acyl carrier protein. Comparison of this gene to functional regions from other species shows that mkA functional regions of *Monascus* BCRC38072 share high similarity with lovB gene of *Aspergillus terreus* and mlcA gene of *Penicillium citrinum*.

Another aspect of the invention features a vector, comprising a nucleotide sequence of SEQ ID NO: 2 (mkA genomic DNA), or a nucleotide sequence sharing 95% homology with SEQ ID NO:2, or a nucleotide sequence hybridizable thereto under stringent conditions and encoding a protein having the nonaketide synthase activity. Tools for constructing the vector of the invention include molecular sequences self-replicable or integratable to chromosome in a host cell, for example, a plasmid, a phage, or a virus; preferably, the vector is a shuttle vector. The vector of the invention further produces various polyketide products by shuffling. Reference to shuffling can be seen in U.S. Pat. Nos.: 6,221,641 and 6,391,594.

Another aspect of the invention also features a transformant, comprising a nucleotide sequence of SEQ ID NO: 2, or a nucleotide sequence sharing 95% homology with SEQ ID NO:2, or a nucleotide sequence hybridizable thereto under stringent conditions and encoding a protein having nonaketide synthase activity, and a host cell for constructing the transformant. The host cell includes prokaryote or eukaryote. Suitable host cells include, but are not limited to, bacteria, yeasts, animal cells, insect cells, plant cells, or filamentous fungi. The filamentous fungi can be *Monascus* sp., particularly *Monascus pilosus, Monascus ruber*, or *Monascus purpureus*, more particularly BCRC38072. Transformation can be completed by applying a transformation method for filamentous fungi belonging to the genus *Aspergillus* using the standing known host-vector system. See EP 1,325,959 A1 P5 [0022].

Another aspect of the invention relates to a method for increasing monacolin K production, comprising the steps of: (a) transforming a nucleotide sequence of SEQ ID NO: 2 (mkA genomic DNA), or a nucleotide sequence sharing 95% homology with SEQ ID NO:2, or a nucleotide sequence hybridizable thereto under stringent conditions and encoding a protein having nonaketide synthase activity into a host cell; and (b) culturing the transformed cell under a condition suitable for the expression of the nucleotide sequence. Preferably, the host cell is originally a monacolin K-producing cell.

Another aspect of the invention relates to a method for increasing HMG-CoA reductase inhibitor production. The method comprises the steps of: (a) transforming a nucleotide sequence of SEQ ID NO: 2, or a nucleotide sequence sharing 95% homology with SEQ ID NO:2, or a nucleotide sequence hybridizable thereto under stringent conditions and encoding a protein having nonaketide synthase activity into a host cell; (b) culturing the transformed cell under a condition suitable for the expression of the nucleotide sequence; and (c) collecting the HMG-CoA reductase inhibitor. Preferably, the host cell is originally a monacolin K-producing cell. (III)

Diketide synthase (mkB genomic DNA)

The invention relates to a DNA sequence comprising a nucleotide sequence of SEQ ID NO: 3 (mkB genomic DNA), or a nucleotide sequence sharing 95% homology with SEQ ID NO:3, or a nucleotide sequence hybridizable thereto under stringent conditions and encoding a protein having diketide synthase activity. The DNA sequence was isolated from BCRC38072. In addition, the DNA sequence of the invention is obtainable for those skilled in the art by known methods such as PCR or hybridization according to the disclosure of the invention. Reference to the stringent conditions can be found in EP 1,325,959 A1 P7 [0036]. Diketide synthase biosynthesizes a branch of monacolin K, namely diketide or designated as 2-methylbutyrate. This gene has multi-functional regions, including β-ketoacyl synthase, acetyl transferase, dehydratase, methyltransferase, ketoreductase, acyl carrier protein, and enoyl reductase. Comparison of this gene to functional regions from other species shows that mkB functional regions of *Monascus pilosus* BCRC38072 share high similarity with lovf gene of *Aspergillus terreus* and mlcB gene of *Penicillium citrinum*.

Another aspect of the invention relates to a vector, comprising a nucleotide sequence of SEQ ID NO: 3, or a nucleotide sequence sharing 95% homology with SEQ ID NO: 3, or a nucleotide sequence hybridizable thereto under stringent conditions and encoding a protein having diketide synthase activity. Tools for constructing the vector of the invention include molecular sequences which are self-replicable or integratable to a chromosome in a host cell, for example, a plasmid, a phage, or a virus. The vector of the invention further produces various polyketide products by shuffling. Reference to shuffling can be seen in U.S. Pat. Nos.: 6,221, 641 and 6,391,594.

Another aspect of the invention also relates to a transformant, comprising a nucleotide sequence of SEQ ID NO: 3, or a nucleotide sequence sharing 95% homology with SEQ ID NO:3, or a nucleotide sequence hybridizable thereto under stringent conditions and encoding a protein having diketide synthase activity, and a host cell for constructing the transformant. The host cell includes prokaryote or eukaryote. Suitable host cells include, but are not limited to, bacteria, yeasts, animal cells, insect cells, plant cells, or filamentous fungi. The filamentous fungi can be *Monascus* sp., particularly *Monascus pilosus, Monascus ruber*, or *Monascus purpureus*, more particularly BCRC38072. Transformation can be completed by applying a transformation method for filamentous fungi belonging to the genus *Aspergillus* using the standing known host-vector system. See EP 1,325,959 A1 P5 [0022].

Another aspect of the invention relates to a method for increasing monacolin K production, comprising the steps of: (a) transforming a nucleotide sequence of SEQ ID NO: 3, or a nucleotide sequence sharing 95% homology with SEQ ID NO:3, or a nucleotide sequence hybridizable thereto under stringent conditions and encoding a protein having diketide synthase activity into a host cell; and (b) culturing the transformed cell under a condition suitable for the expression of the nucleotide sequence. Preferably, the host cell is originally a monacolin K-producing cell.

Another aspect of the invention relates to a method for increasing HMG-CoA reductase inhibitor production. The method comprises the steps of: (a) transforming a nucleotide sequence of SEQ ID NO: 3, or a nucleotide sequence sharing 95% homology with SEQ ID NO:3, or a nucleotide sequence hybridizable thereto under stringent conditions and encoding a protein having diketide synthase activity into a host cell; (b) culturing the transformed cell under a condition suitable for the expression of the nucleotide sequence; and (c) collecting the HMG-CoA reductase inhibitor. Preferably, the host cell is originally a monacolin K-producing cell.

(IV) Transcription Factor (mkH Genomic DNA)

Figure 4:
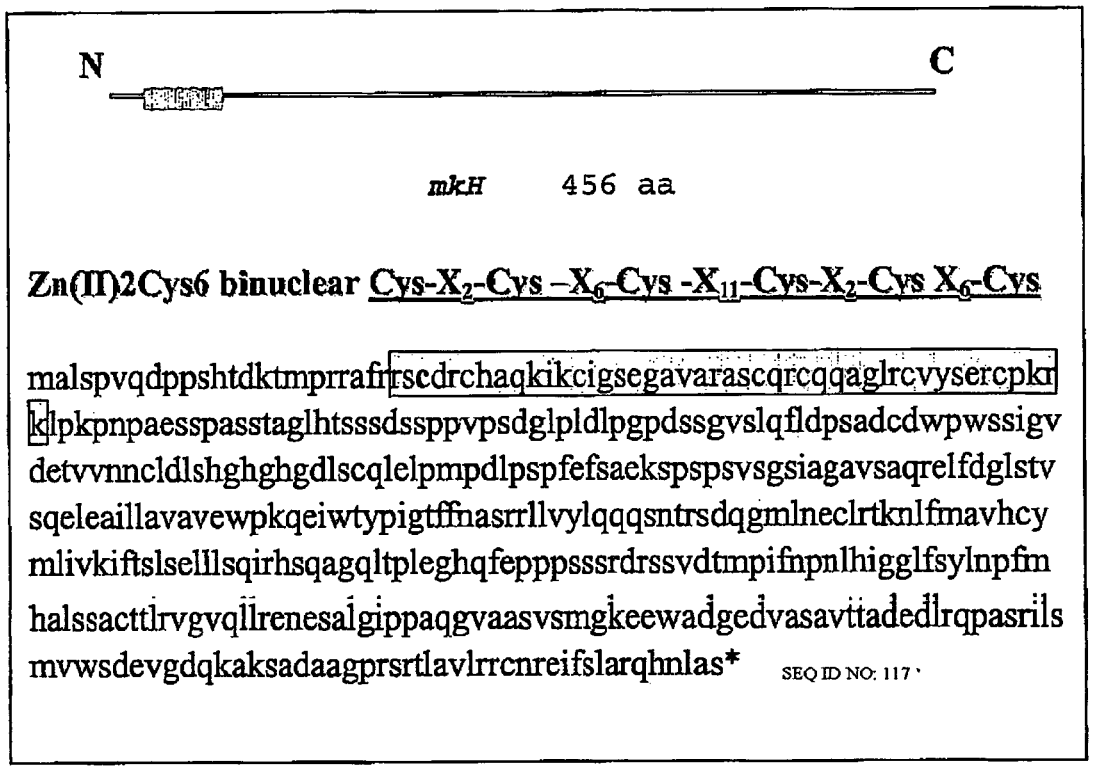
FIG. 4 illustrates MKH amino acid sequence and putative Zn(II)Cys6 binuclear motif analyzed by Vector NTI. The amino acid sequence in the box indicates Zn (II) Cys6 binuclear motif; 6 Cys is marked in gray label.

The invention relates to a DNA sequence comprising a nucleotide sequence of SEQ ID NO: 9 (mkH genomic DNA), or a nucleotide sequence sharing 95% homology with SEQ ID NO:9, or a nucleotide sequence hybridizable thereto under stringent conditions and encoding a protein having transcription factor activity. The DNA sequence was isolated from BCRC38072. In addition, the DNA sequence of the invention is obtainable for those skilled in the art by known methods such as PCR or hybridization according to the disclosure of the invention. Reference to the stringent conditions can be found in EP 1,325,959 A1 P7 [0036]. mkH gene is identified as Zn(II)Cys6 binuclear motif from Vector NTI comparison. The conserved sequence of this gene is Cys-X2-Cys-X6-Cys-X11-Cys-X2-Cys-X6-Cys, as shown in FIG. 4.

Another aspect of the invention relates to a vector, comprising a nucleotide sequence of SEQ ID NO: 9, or a nucleotide sequence sharing. 95% homology with SEQ ID. NO:9, or a nucleotide sequence hybridizable thereto under stringent conditions and encoding a protein having transcription factor activity. Tools for constructing the vector of the invention include molecular sequences self-replicable or integratable to chromosome in a host cell, for example, a plasmid, a phage, or a virus. Preferably, the vector of the invention is an expression vector.

Another aspect of the invention also relates to a transformant, comprising a nucleotide sequence of SEQ ID NO: 9, or a nucleotide sequence sharing 95% homology with SEQ ID NO:9, or a nucleotide sequence hybridizable thereto under stringent conditions and encoding a protein having transcriptional factor activity, and a host cell for constructing the transformant. The host cell includes prokaryote or eukaryote. Suitable host cells include, but are not limited to, bacteria, yeasts, animal cells, insect cells, plant cells, or filamentous fungi. The filamentous fungi can be *Monascus* sp., particularly *Monascus pilosus, Monascus ruber*, or *Monascus purpureus*, more particularly BCRC38072. Transformation can be completed by applying a transformation method for filamentous fungi belonging to the genus *Aspergillus* using the standing known host-vector system. See EP 1,325,959 A1 P5 [0022].

Another aspect of the invention relates to an expression system. The expression system comprises a nucleotide sequence of SEQ ID NO: 9, or a nucleotide sequence sharing 95% homology with SEQ ID NO:9, or a nucleotide sequence hybridizable thereto under stringent conditions and encoding a protein having transcription factor activity, and a host cell for expressing the nucleotide sequence. The sequence is transformed into the host cell by transformation. Suitable host cells include bacteria, yeasts, animal cells, insect cells, plant cells, or filamentous fungi. The filamentous fungi can be *Monascus* sp., particularly *Monascus pilosus, Monascus ruber*, or *Monascus purpureus*, more particularly BCRC38072.

Another aspect of the invention relates to a method for increasing monacolin K production, comprising the steps of: (a) transforming a nucleotide sequence of SEQ ID NO: 9, or a nucleotide sequence sharing 95% homology with SEQ ID NO: 9, or a nucleotide sequence hybridizable thereto under stringent conditions and encoding a protein having transcription factor activity into a host cell; and (b) culturing the transformed cell under a condition suitable for the expression of the nucleotide sequence. Preferably, the host cell is originally a monacolin K-producing cell.

Another aspect of the invention relates to a method for increasing HMG-CoA reductase inhibitor production. The method comprises the steps of: (a) transforming a nucleotide sequence of SEQ ID NO: 9, or a nucleotide sequence sharing 95% homology with SEQ ID NO:9, or a nucleotide sequence hybridizable thereto under stringent conditions and encoding a protein having transcription factor activity into a host cell; (b) culturing the transformed cell under a condition suitable for the expression of the nucleotide sequence; and (c) collecting the HMG-CoA reductase inhibitor. The host cell includes prokaryote or eukaryote. Suitable host cells include, but are not limited to, bacteria, yeasts, animal cells, insect cells, plant cells, or filamentous fungi. The filamentous fungi can be *Monascus* sp., particularly *Monascus pilosus, Monascus ruber*, or *Monascus purpureus*, more particularly BCRC38072.

(V) HMG-CoA Reductase Inhibitor and Monacolin K Production

The invention relates to a method for the production of HMG-CoA reductase inhibitor, preferable for the production of monacolin K. The method comprises the steps of: (a) transforming a nucleotide sequence of SEQ ID NO: 2 (mkA genomic DNA), SEQ ID NO: 3 (mkB genomic DNA), SEQ ID NO: 6 (mkE genomic DNA), and SEQ ID NO: 7 (mkF genomic DNA), or a nucleotide sequence hybridizable to these sequences under stringent conditions into a host cell, wherein these sequences encode proteins having nonaketide synthase, diketide synthase, dehydrogenase, and transesterase activity respectively; (b) culturing the transformed cell under a condition suitable for the expression of the nucleotide sequences; and (c) collecting monacolin K. The host cell includes prokaryote or eukaryote. Suitable host cells include, but are not limited to, bacteria, yeasts, animal cells, insect cells, plant cells, or filamentous fungi. The filamentous fungi can be *Monascus* sp., particularly *Monascus pilosus, Monascus ruber*, or *Monascus purpureus*, more particularly BCRC38072. Hutchinson et al. (2000) proposed that four genes are necessary for lovastatin synthesis when heterologously expressed, which are nonaketide synthase, diketide synthase, dehydrogenase, and transesterase. Among these, nonaketide synthase and dehydrogenase contribute the production of lovastatin precursor, diketide synthase assists the production of 2-methylbutyrate, and the produced 2-methylbutyrate binds to nonaketide by transesterase and form the complete lovastatin.

The above mentioned method further comprises a nucleotide sequence of SEQ ID NO: 4 (mkC genomic DNA), SEQ ID NO: 5 (mkD genomic DNA), SEQ ID NO: 8 (mkG genomic DNA), SEQ ID NO: 9 (mkH genomic DNA), and SEQ ID NO: 10 (mkI genomic DNA), or a nucleotide sequence sharing 95% homology with these sequences, or a nucleotide sequence hybridizable to these sequences under stringent conditions, wherein these sequences encode proteins having P450 monooxygenase, oxidoreductase, HMG-CoA reductase, transcription factor, and efflux pump activity respectively.

(VI) Nonaketide Synthase (mkA cDNA)

The invention relates to a DNA sequence comprising a nucleotide sequence of SEQ ID NO: 19 (mkA cDNA), or a nucleotide sequence sharing 95% homology with SEQ ID NO: 19, or a nucleotide sequence hybridizable thereto under stringent conditions and encoding a protein having nonaketide synthase activity. The DNA sequence was isolated from BCRC38072. In addition, the DNA sequence of the invention is obtainable for those skilled in the art by known methods such as PCR or hybridization according to the disclosure of the invention.

Another aspect of the invention relates to a vector, comprising a nucleotide sequence of SEQ ID NO: 19 (mkA cDNA), or a nucleotide sequence sharing 95% homology with SEQ ID NO: 19, or a nucleotide sequence hybridizable thereto under stringent conditions and encoding a protein having nonaketide synthase activity. Tools for constructing the vector of the invention include molecular sequences self-replicable or integratable to chromosome in a host cell, for example, a plasmid, a phage, or a virus. Preferably, the vector of the invention is an expression vector. More preferably, the vector of the invention is pPICZαA (invitrogen). The construct of the invention is pPICZamkA comprising the nucleotide sequence of SEQ ID NO: 19. The construct pPICZamkA was obtained by cloning full-length cDNA of mkA gene into pPICZαA according to the methods described in Molecular Cloning. Various polyketide products can be produced using the vector of the invention by shuffling. Reference to shuffling can be seen in U.S. Pat. Nos.: 6,221,641 and 6,391,594.

Another aspect of the invention also relates to a transformant, comprising a nucleotide sequence of SEQ ID NO: 19, or a nucleotide sequence sharing 95% homology with SEQ ID NO: 19, or a nucleotide sequence hybridizable thereto under stringent conditions and encoding a protein having nonaketide synthase activity, and a host cell for constructing the transformant. The host cell includes prokaryote or eukaryote. Suitable host cells include, but are not limited to, bacteria, yeasts, animal cells, insect cells, plant cells, or filamentous fungi. The filamentous fungi can be *Monascus* sp., particularly *Monascus pilosus, Monascus ruber*, or *Monascus purpureus*, more particularly BCRC38072. Transformation can be completed by applying a transformation method for filamentous fungi belonging to the genus *Aspergillus* using the standing known host-vector system. See EP 1,325,959 A1 P5 [0022].

Another aspect of the invention relates to a method for increasing monacolin K production, comprising the steps of: (a) transforming a nucleotide sequence of SEQ ID NO: 19, or a nucleotide sequence sharing 95% homology with SEQ ID NO: 19, or a nucleotide sequence hybridizable thereto under stringent conditions and encoding a protein having nonaketide synthase activity into a host cell; and (b) culturing the transformed cell under a condition suitable for the expression of the nucleotide sequence. Preferably, the host cell is originally a monacolin K-producing cell.

Another aspect of the invention relates to a method increasing HMG-CoA reductase inhibitor production. The method comprises the steps of: (a) transforming a nucleotide sequence of SEQ ID NO: 19, or a nucleotide sequence sharing 95% homology with SEQ ID NO:19, or a nucleotide sequence hybridizable thereto under stringent conditions and encoding a protein having nonaketide synthase activity into a host cell; (b) culturing the transformed cell under a condition suitable for the expression of the nucleotide sequence; and (c) collecting the HMG-CoA reductase inhibitor. Preferably, the host cell is originally a monacolin K-producing cell.

(VII) Diketide Synthase (mkB cDNA)

The invention relates to a DNA sequence comprising a nucleotide sequence of SEQ ID NO: 20 (mkB cDNA), or a nucleotide sequence sharing 95% homology with SEQ ID NO: 20, or a nucleotide sequence hybridizable thereto under stringent conditions and encoding a protein having diketide synthase activity. The DNA sequence was isolated from BCRC38072. In addition, the DNA sequence of the invention is obtainable for those skilled in the art by known methods such as PCR or hybridization according to the disclosure of the invention.

Another aspect of the invention relates to a vector, comprising a nucleotide sequence of SEQ ID NO: 20 (mkB cDNA), or a nucleotide sequence sharing 95% homology with SEQ ID NO:20, or a nucleotide sequence hybridizable thereto under stringent conditions and encoding a protein having diketide synthase activity. Tools for constructing the vector of the invention include molecular sequences self-replicable or integratable to chromosome in a host cell, for example, a plasmid, a phage, or a virus. Preferably, the vector of the invention is an expression vector. More preferably, the vector of the invention is pPICZαC (invitrogen). The construct of the invention is pPICZamkB comprising the nucleotide sequence of SEQ ID NO: 20. The construct pPICZamkB was obtained by cloning full-length cDNA of mkB gene into pPICZαC according to the methods described in Molecular Cloning. Various polyketide products can be produced using the vector of the invention by shuffling. Reference to shuffling can be seen in U.S. Pat. Nos.: 6,221,641 and 6,391,594.

Another aspect of the invention also relates to a transformant, comprising a nucleotide sequence of SEQ ID NO: 20, or a nucleotide sequence sharing 95% homology with SEQ ID NO: 20, or a nucleotide sequence hybridizable thereto under stringent conditions and encoding a protein having diketide synthase activity, and a host cell for constructing the transformant. The host cell includes prokaryote or eukaryote. Suitable host cells include, but are not limited to, bacteria, yeasts, animal cells, insect cells, plant cells, or filamentous fungi. The filamentous fungi can be *Monascus* sp., particularly *Monascus pilosus, Monascus ruber*, or *Monascus purpureus*, more particularly BCRC38072. Transformation can be completed by applying a transformation method for filamentous fungi belonging to the genus *Aspergillus* using the standing known host-vector system. See EP 1,325,959 A1 P5 [0022].

Another aspect of the invention relates to a method for increasing monacolin K production, comprising the steps of: (a) transforming a nucleotide sequence of SEQ ID NO: 20, or a nucleotide sequence sharing 95% homology with SEQ ID NO: 20, or a nucleotide sequence hybridizable thereto under stringent conditions and encoding a protein having diketide synthase activity into a host cell; and (b) culturing the transformed cell under a condition suitable for the expression of the nucleotide sequence. Preferably, the host cell is originally a monacolin K-producing cell.

Another aspect of the invention relates to a method for increasing HMG-CoA reductase inhibitor production. The method comprises the steps of: (a) transforming a nucleotide sequence of SEQ ID NO: 20, or a nucleotide sequence sharing 95% homology with SEQ ID NO: 20, or a nucleotide sequence hybridizable thereto under stringent conditions and encoding a protein having diketide synthase activity into a host cell; (b) culturing the transformed cell under a condition suitable for the expression of the nucleotide sequence; and (c) collecting the HMG-CoA reductase inhibitor. Preferably, the host cell is originally a monacolin K-producing cell.

(VIII) Transcription Factor (mkH cDNA)

The invention relates to a DNA sequence comprising a nucleotide sequence of SEQ ID NO: 25 (mkH cDNA), or a nucleotide sequence sharing 95% homology with SEQ ID NO: 25, or a nucleotide sequence hybridizable thereto under stringent conditions and encoding a protein having transcription factor activity. The DNA sequence was isolated from BCRC38072. In addition, the DNA sequence of the invention is obtainable for those skilled in the art by known methods such as PCR or hybridization according to the disclosure of the invention. Reference to Stringent conditions can be seen in EP 1,325,959 A1 P7 [0036].

Another aspect of the invention relates to a vector, comprising a nucleotide sequence of SEQ ID NO: 25, or a nucleotide sequence sharing 95% homology with SEQ ID NO: 25, or a nucleotide sequence hybridizable thereto under stringent conditions and encoding a protein having transcription factor activity. Tools for constructing the vector of the invention include molecular sequences self-replicable or integratable to chromosome in a host cell, for example, a plasmid, a phage, or a virus. Preferably, the vector of the invention is an expression vector. More preferably, the vector of the invention is pMS. The construct of the invention is pMSmkH comprising the nucleotide sequence of SEQ ID NO: 25. The construct pMSmkH was obtained by cloning full-length cDNA of mkH gene into pMS according to the methods described in Molecular Cloning.

Another aspect of the invention also relates to a transformant, comprising a nucleotide sequence of SEQ ID NO: 25, or a nucleotide sequence sharing 95% homology with SEQ ID NO: 25, or a nucleotide sequence hybridizable thereto under stringent conditions and encoding a protein having transcription factor activity, and a host cell for constructing the transformant. The host cell includes prokaryote or eukaryote. Suitable host cells include, but are not limited to, bacteria, yeasts, animal cells, insect cells, plant cells, or filamentous fungi. The filamentous fungi can be *Monascus* sp., particularly *Monascus pilosus, Monascus ruber*, or *Monascus purpureus*, more particularly BCRC38072. Transformation can be completed by applying a transformation method for filamentous fungi belonging to the genus *Aspergillus* using the standing known host-vector system. See EP 1,325,959 A1 P5 [0022].

Another aspect of the invention relates to an expression system. The expression system comprises a nucleotide sequence of SEQ ID NO: 25, or a nucleotide sequence sharing 95% homology with SEQ ID NO: 25, or a nucleotide sequence hybridizable thereto under stringent conditions, and a host cell suitable for expressing the nucleotide sequence, wherein the sequence is transformed into the host cell by transformation. Suitable host cells include bacteria, yeasts, animal cells, insect cells, plant cells, or filamentous fungi. The filamentous fungi can be *Monascus* sp, particularly *Monascus pilosus, Monascus ruber*, or *Monascus purpureus*, more particularly BCRC38072.

Another aspect of the invention relates to a method for increasing monacolin K production, comprising the steps of: (a) transforming a nucleotide sequence of SEQ ID NO: 25, or a nucleotide sequence sharing 95% homology with SEQ ID NO: 25, or a nucleotide sequence hybridizable thereto under stringent conditions and encoding a protein having transcription factor activity into a host cell; and (b) culturing the transformed cell under a condition suitable for the expression of the nucleotide sequence. Preferably, the host cell is originally a monacolin K-producing cell.

Another aspect of the invention relates to a method for increasing HMG-CoA reductase inhibitor production. The method comprises the steps of: (a) transforming a nucleotide sequence of SEQ ID NO: 25, or a nucleotide sequence sharing 95% homology with SEQ ID NO: 25, or a nucleotide sequence hybridizable thereto under stringent conditions and encoding a protein having transcription factor activity into a host cell; (b) culturing the transformed cell under a condition suitable for the expression of the nucleotide sequence; and (c) collecting the HMG-CoA reductase inhibitor. Preferably, the host cell is originally a monacolin K-producing cell. (IX) HMG-CoA reductase inhibitor and Monacolin K production The invention relates to a method for the production of HMG-CoA reductase inhibitor, preferable the production of monacolin K. The method comprises the steps of: (a) transforming a nucleotide sequence of SEQ ID NO: 19 (mkA cDNA), SEQ ID NO: 20 (mkB cDNA), SEQ ID NO: 23 (mkE cDNA), and SEQ ID NO: 24 (mkF cDNA), or a nucleotide sequence hybridizable to these sequences under stringent conditions into a host cell, wherein these sequences encode proteins having nonaketide synthase, diketide synthase, dehydrogenase, and transesterase activity respectively; (b) culturing the transformed cell under a condition suitable for the expression of the nucleotide sequences; and (c) collecting monacolin K. The host cell includes prokaryote or eukaryote. Suitable host cells include, but are not limited to, bacteria, yeasts, animal cells, insect cells, plant cells, or filamentous fungi. The filamentous fungi can be *Monascus* sp., particularly *Monascus pilosus, Monascus ruber*, or *Monascus purpureus*, more particularly BCRC38072. Hutchinson et al. (2000) proposed that four genes are necessary for lovastatin synthesis when heterologously expressed, which are nonaketide synthase, diketide synthase, dehydrogenase, and transesterase. Among these, nonaketide synthase and dehydrogenase contribute the production of lovastatin precursor, diketide synthase assists the production of 2-methylbutyrate, and the produced 2-methylbutyrate binds to nonaketide by transesterase and form the complete lovastatin.

The above mentioned method further comprises a nucleotide sequence of SEQ ID NO: 21 (mkC cDNA), SEQ ID NO: 22 (mkD cDNA), SEQ ID NO: 25 (mkH cDNA), and SEQ ID NO: 26 (mkI cDNA), or a nucleotide sequence sharing 95% homology with these sequences, or a nucleotide sequence hybridizable to these sequences under stringent conditions, wherein these sequences encode proteins having P450 monooxygenase, oxidoreductase, transcription factor, and efflux pump activity respectively.

EXAMPLE

Example 1

Cultivation of *Monascus*

*Monascus* was inoculated in slant PDA (Potato Dextrose Agar) and cultured at 30° C. Hyphae and spores were scraped, inoculated in 50 ml medium (7% glycerol, 3% glucose, 3% MSG, 1.2% polypeptone, 0.2% $NaNO_3$, 0.1% $MgSO_4 \cdot 7H_2O$), and cultured under vibration at 25° C.

Example 2

Construction of *Monascus* BAC Library

A. Preparation of *Monascus* Nuclei

*Monascus* cells were collected, washed with $ddH_2O$, and dried by air-extraction. 10× volume of pre-cold wash buffer (HB buffer+1.5% β-mercaptoethanol) was added to the dried cells, and the cells were homogenized in a blender. *Monascus* nuclei were obtained by Miracloth filtration.

B. Preparation of Plugs and Chromosomal DNA 1.8% low melting temperature agarose was prepared in HB buffer and placed in a 50° C. water-bath. Equal volumes of agarose and nuclei solution were mixed thoroughly and added into plug mold (Bio-Rad). The impurities were treated with proteinase K (1 mg/mL). The plugs were spliced to small pieces and partially digested by HindIII. After restriction reaction, the plugs were analyzed under 1% agarose gel for pulse electrophoresis. DNA fragments with 200 kb were recovered by electro-elution.

C. Construction of *Monascus* Library pIndigoBAC-5 HindIII ready (Epicentre) was used as the vector for ligation with recovered DNA. The ligation reactant was then electroporated into competent cells (Epicentre, TransforMax™ EC 100™ electro competent *E. coli*.). Colonies were stored at 384 microplates.

Example 3

Design of Primers for Probes and Preparation of Probes

PCR and sequencing were performed by degenerate primers, and the obtained DNA sequence was used as a basis for designing primers of a 226 bp probe, as shown in Attachment 1. The software Vector NTI was employed for designing primers, and the designed primers are listed below.

```
Mplov1 5' TCCACTGCCGTTTATGTTG 3'    (SEQ ID NO: 29)

Mplov2 5' TCGTCATCTTCACCCCATC 3'    (SEQ ID NO: 30)
```

A DNA sequence containing DIG-11-dUTP (Roche, PCR DIG Probe Synthesis Kit) was amplified by PCR and used as the probe.

Example 4

Analysis of Colony Hybridization and Extraction of BAC DNA

A corner of the nylon membrane (Roche) was cut to mark the direction, and the nylon membrane was then placed on a plate containing colonies. The nylon membrane with the colony side up was sequentially contacted with 5 min lysis solution (2N NaOH, 0.1% SDS), 5 min 0.5 M NaOH/1.5 M NaCl solution, 5 min 1.5 M NaCl/0.5 M Tris-HCl (pH 7.4), and 5 min 2×SSC. DNA was then immobilized on the nylon membrane by UV light. The obtained nylon membrane was used for hybridization and immuno-detection (Roche). After that, the colonies obtained from the reaction were cultured, and the BAC DNA was extracted using Large-Construct Kit (Qiagen).

Example 5

Analysis of Shotgun Sequence

A. Preparation of Shotgun Library

3~5 μg of BAC DNA was sonicated to be 1~2 kb under suitable sonication conditions, and the results were confirmed by electrophoresis. DNA was then repaired by Bal31 nuclease and T4 DNA polymerase to be blunt-ended, and DNA fragments with 1~2 kb were recovered from electrophoresis. Ligation was performed using pUC18/SmaI/CIAP (50 ng/μL) (Pharmacia) as a vector and the ligation reactant was electroporated to $E.\ coli$ DH5α.

B. DNA Sequencing and Analysis

Plasmid DNA was extracted with high throughput using a 96 microplate, and the obtained plasmid DNA was sequenced by ABI Bigdye v3.0 Kit. The sequence analysis was performed by ABI3700 sequencer with 10× coverage.

Example 6

DNA Sequence Assembly and Annotation

DNA sequence assembly was performed by Phred-Phrap-Consed developed by Phil Green lab. The full-length BAC was further annotated by Vector NTI and BLAST

Example 7

Extraction of Monascus Total RNA and RT-PCR Reaction 0.2 g of Monascus hyphae was placed in a mortar, frozen by liquid nitrogen, and then powdered. Total RNA was extracted using trizol reagent (Invitrogen) and chloroform, and dissolved in DEPC-H$_2$O. RNA was used as a template for reverse transcription (Promega, ImProm-IITM Reverse Transcription System) to obtain a full-length cDNA. The full-length cDNA was ligated to TA vector (promega, pGEM-T vector system).

Example 8

RNA Electrophoresis and Northern Blot

A. RNA Electrophoresis 1.2% agarose gel containing formaldehyde gel running buffer and formaldehyde was prepared. RNA was mixed with formaldehyde gel running buffer, formaldehyde (37%), and formamide thoroughly. RNA electrophoresis was performed and the gel was stained with ETBr.

B. RNA Transferring

Nylon membrane was cut in the same size of the gel, and a corner of the nylon membrane was cut to mark the direction. RNA transferring from the gel to the nylon membrane was performed, and RNA was immobilized on the nylon membrane by UV light. The obtained nylon membrane was used for hybridization and immuno-detection (Roche).

Example 9

Design of Primers for Probes and Preparation of Probes

Primers were designed according to the BAC DNA sequence for the preparation of probes used for Northern blot. The designed primers were listed below.

mkA Gene

```
                                      (SEQ ID NO: 31)
    Forward 5'ATA GCT CCG AGA ATG GTC CC 3'
                                      (SEQ ID NO: 32)
    Reverse 5'CCA TCA AGG ATG CTC TGT CG 3'
```

Length of the probe: 229 bp mkB Gene

```
                                      (SEQ ID NO: 33)
Forward 5' CTA GAC TTT GCT TCC CAC GCC A 3'
                                      (SEQ ID NO: 34)
Reverse 5' CAT TGT CGA GCG TTG GAG TC 3'
```

Length of the probe: 167 bp mkC Gene

```
                                      (SEQ ID NO: 35)
Forward 5'GGC CTG AGC CGA AGA AGT AC 3'
                                      (SEQ ID NO: 36)
Reverse 5'TCA GAG ATC TTC GTC CCG AC 3'
```

Length of the probe: 304 bp mkD Gene

```
                                      (SEQ ID NO: 37)
Forward 5'TGA TGA CTT TGC CCT GGC GG 3'
                                      (SEQ ID NO: 38)
Reverse 5'TCA CCC AAT GAC TCT AGC CC 3'
```

Length of the probe: 175 bp
mkE Gene

Forward 5'TTC TCT CCC GAC AAC TGC CC 3' (SEQ ID NO: 39)

Reverse 5'AAT GGT CAC CGC CGA CTG GA 3' (SEQ ID NO: 40)

Length of the probe: 246 bp
mkF Gene

Forward 5'GCC CCG AAT CCT ACA TGA AG 3' (SEQ ID NO: 41)

Reverse 5'GGC CCA CCG TAG TTG ATG TG 3' (SEQ ID NO: 42)

Length of the probe: 166 bp
mkG Gene

Forward 5'CCT CGC TCT GAA TAT GAC CC 3' (SEQ ID NO: 43)

Reverse 5'TCG GAT CGG CTT CTC AAA CC 3' (SEQ ID NO: 44)

Length of the probe: 217 bp
mkH Gene

Forward 5'ACC TCA TCG CTC CAG ACC AT 3' (SEQ ID NO: 45)

Reverse 5'CTG CGA GAG AAT GAG AGT GC 3' (SEQ ID NO: 46)

Length of the probe: 179 bp
mkI Gene

Forward 5'CTA GAC TCG TTC ATC GCG GC 3' (SEQ ID NO: 47)

Reverse 5'CCA TAC ATT CTA CCT TGC GG 3' (SEQ ID NO: 48)

Length of the probe: 127 bp

Example 10

Transformation of *Pichia pastoris*

Full-length cDNAs of PKS (mkA and mkB) was ligated to pPICZαA and C (Invitrogen), respectively. Transformation was performed using *Pichia* EasyComp. Kit (Invitrogen).

Example 11

Southern Blot

Acid depurination was performed by immersing the gel in 0.25 M HCl for 10 min shaking on a flat shaker, and the gel was washed with ddH$_2$O. Denaturation was then performed by immersing the gel in NaCl/NaOH solution (1.5 M NaCl, 0.5 N NaOH) for 15 min shaking twice, and the gel was washed with ddH$_2$O. Neutralization was finally performed by immersing the gel in NaCl/Tris-HCl solution (1.5 M NaCl, 1 M Tris-HCl, pH 7.4) for 15 min shaking twice. Nylon membrane with the same size of the gel was prepared and a corner of the nylon membrane was cut to mark the direction. DNA was transferred from the gel to the nylon membrane and immobilized on the nylon membrane by UV light. The obtained nylon membrane can be used for hybridization and immuno-detection (Roche). Primers listed below were designed for the preparation of probes used for Southern blot.

mkA Gene

Forward2 5'TGA ACA GCA CAG CAT AGG GG 3' (SEQ ID NO: 49)

Reverse2 5'GCA GCC ATT GAA GAC GGC AT 3' (SEQ ID NO: 50)

Length of the probe: 293 bp
mkB Gene

Forward 5' CTA GAC TTT GCT TCC CAC GCC A 3' (SEQ ID NO: 51)

Reverse 5' CAT TGT CGA GCG TTG GAG TC 3' (SEQ ID NO: 52)

Length of the probe: 167 bp

Example 12

Production of Polyketid

Figure 5:
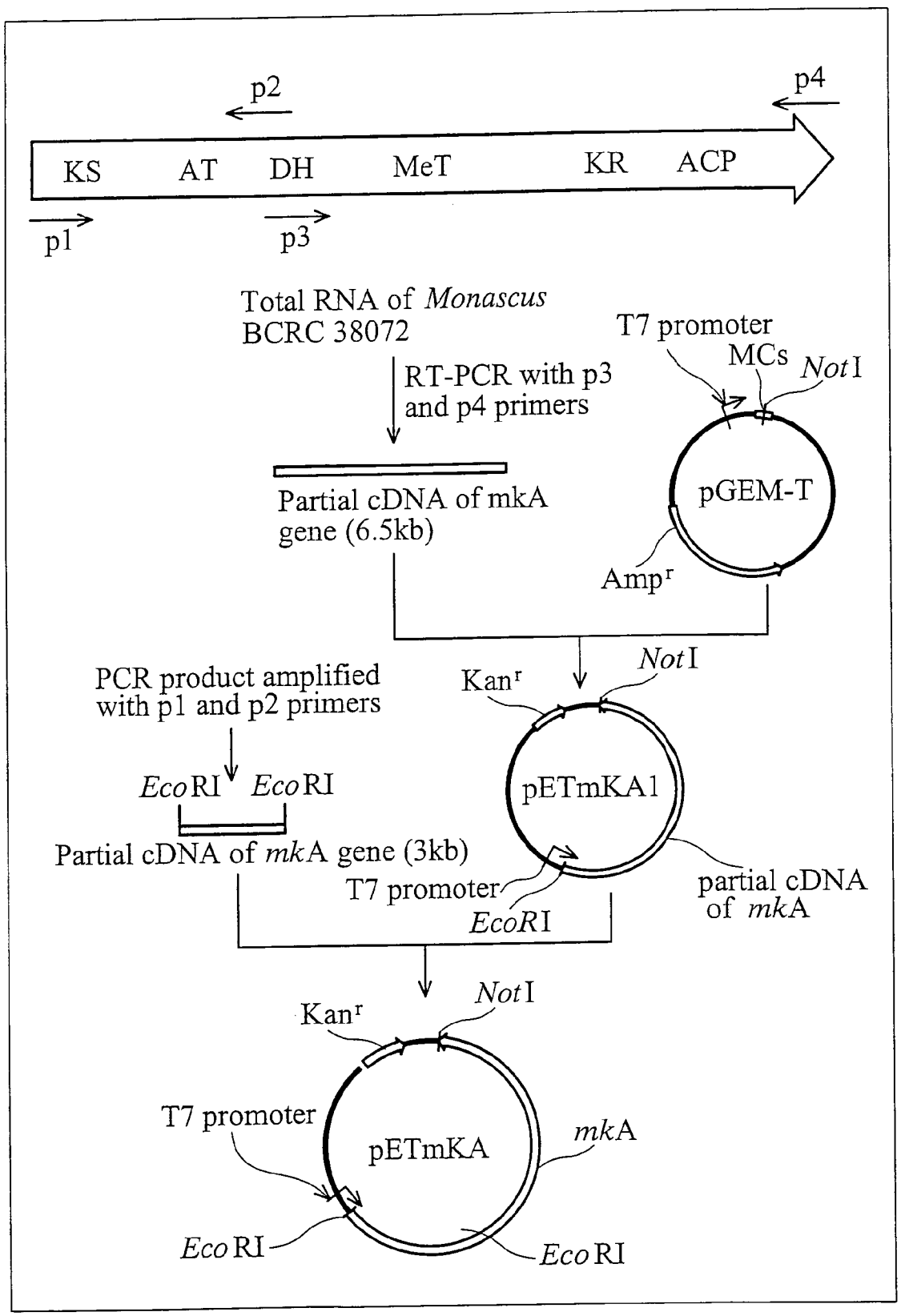
FIG. 5 illustrates constructions of *E. coli* expression vector containing polyketide synthase mkA gene. One set of oligonucleotides primers (p3 and p4) was designed to amplify the partial cDNA of mkA gene (6.5 kb) by RT-PCR. The primers of p1 and p2 were designed to amplify the partial cDNA of mkA gene (3.0 kb) by RT-PCR.
Figure 6:
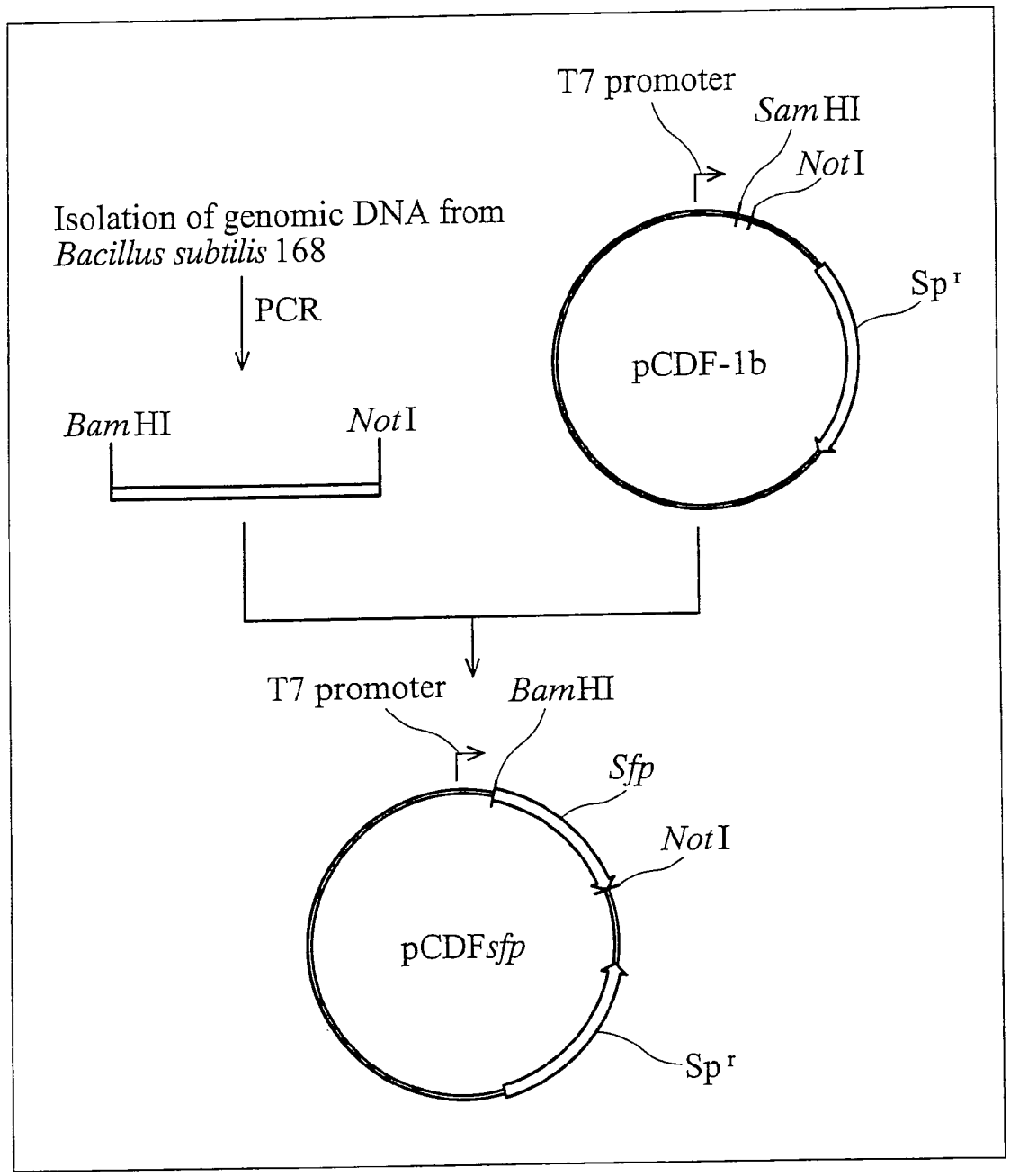
FIG. 6 illustrates construction of *E. coli* expression vector containing 4'-phosphopantetheine transferase sfp gene from *B. subtilis*.
Figure 7:
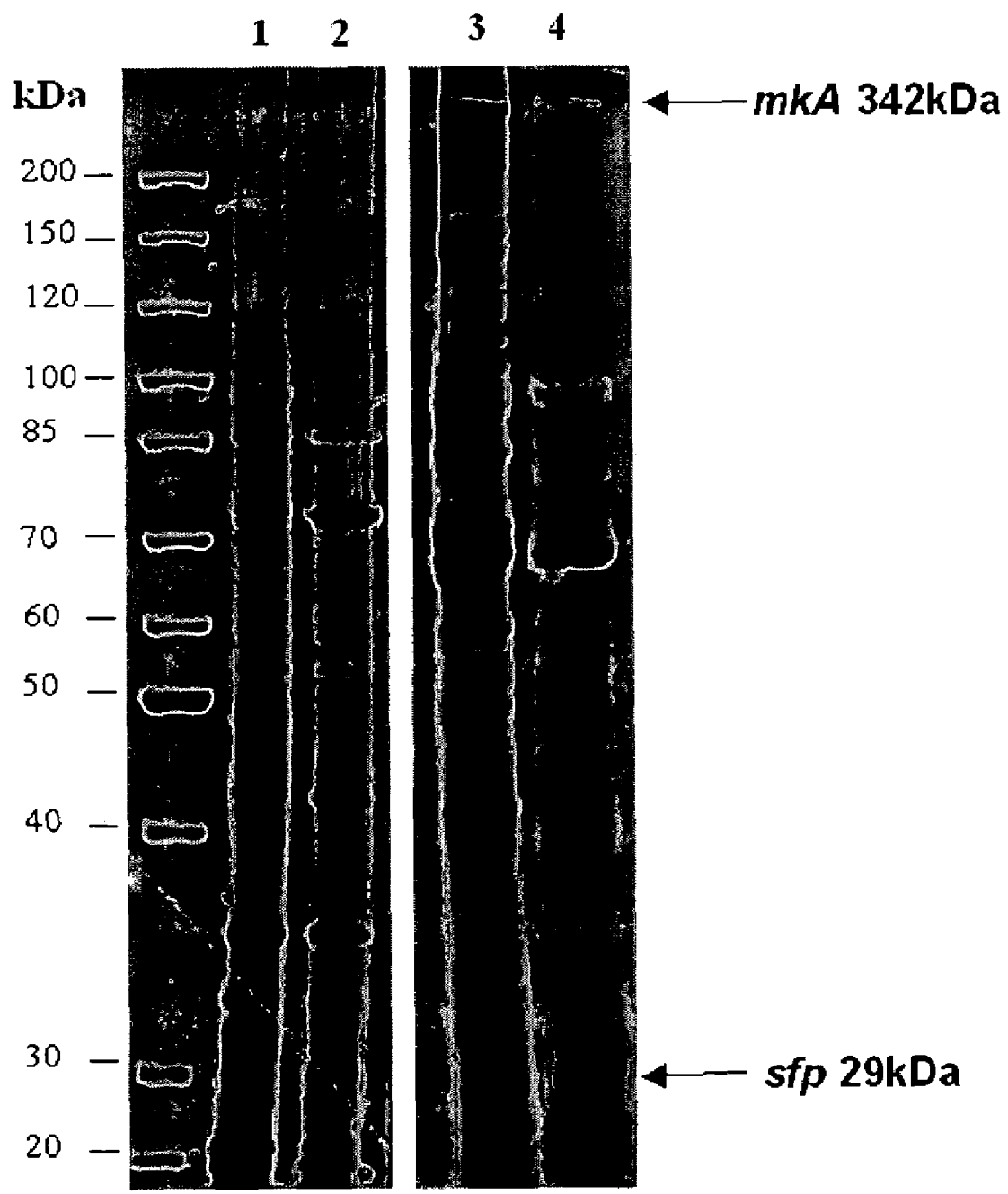
FIG. 7 illustrates expression of mkA and sfp in *E. coli*. Total proteins of *E. coli* harboring the control plasmids pCDF-1b and pET30 (lane 1) and expression plasmids pCDFsfp (sfp gene) and pETmkA (mkA gene) (lane 2) were boiled in loading buffer and subjected to SDS-PAGE. Proteins were stained with colloidal coomassie blue. Arrows indicate the positions of Sfp and MKA. The lysate proteins were purified by ProBond™ purification system (Invitrogen). Lane 3 indicates the lysate centrifuging at 3000×g for 60 min and lane 4 is the proteins purified by Ni-column.

The utility of *E. coli* and *Streptomyces* as hosts of heterologous polyketide synthase expression has been studied by Bedford (1995), Gokhale (1999) and Pfeifer (2001). Moreover, bacterial polyketide synthases have been successfully expressed in *E. coli* and *Streptomyces* and a lower level yield of polyketide has been detected. In general, a lack of post-translational modification in *E. coli* prevents heterologous expression of functional polyketide synthase. Therefore, it is reasonable to coexpress PKS with 4'-phosphopantetheine transferase (PPTase) to produce holo-ACP (acyl carrier protein) domain of PKS for polyketide production (Mootz et al., 2001). To further investigate the expression effect of the expression vector of the invention, the sfp gene (PPTase) of *Bacillus subtilis* has been successfully cloned to introduce into expression vector, pCDF-1b (FIG. 6) and coexpress with PKS, mkA gene (FIG. 5), in *E. coli*. The result of SDS-PAGE showed that a lower level yield of PKS soluble protein (342 kDa) (FIG. 7). However, the most protein of Sfp was soluble and resulted in the expression of 29 kDa protein.

1. Construction of Expression Plasmids

The partial cDNA fragment (6.5 kb cDNA with forward primer p3: 5'-CCATCAAGGATGCTCTGTCG-3' (SEQ ID NO: 49) and reverse primer p4: 5'-TCAAGCCAACT-TCAACGCGG-3' (SEQ ID NO: 50)) of mkA gene was amplified from the first strand cDNA of *Monascus* by RT-PCR. The 6.5 kb cDNA fragment was introduced into pGEM-T vector to obtain the EcoRI-NotI fragment by restricted reaction. Then the fragment was ligated with pET30 to give pETmkA1. One set of oligonucleotide primers with forward primer p1: 5'-GGAATTCATGTACGTAG-GACGCATTGGTGC-3' (SEQ ID NO: 51) contained 23 bases complementary to the 5' mkA gene and introduced EcoRI restriction site and reverse primer p2: 5'-TCGCGAG-GACGGACAAAGTT-3' (SEQ ID NO: 52) was designed to amplify the partial 3.0 kb cDNA by RT-PCR. The 3.0 kb EcoRI-EcoRI cDNA fragment was ligated with pETmkA1 to give pETmkA (FIG. 6).

One set of oligonucleotide primers with forward primer 5'-CGGGATCCCATGAAGATTTACGGAATTTA-3' (SEQ ID NO: 53) contained 20 bases complementary to the 5' sfp gene and introduced BamHI restriction site and reverse primer 5'-ATAGTTTAGCGGCCGCT-TATAAAAGCTCTTCGTACG-3' (SEQ ID NO: 54) contained 20 bases complementary to the 5' sfp gene and introduced NotI restriction site was designed to amplify the sfp gene from genomic DNA of Bacillus subtilis 168. The BamHI-NotI sfp gene was ligated with pCDF-1b to give pCDFsfp (FIG. 7).

2. Coexpression of mkA and sfp in E. coli

Both pETmkA and pCDFsfp were cotransformed into E. coli BL21 (DE3) and LB medium was inoculated with a single colony for culture of overnight. Then, the LB medium was transferred into ATCC medium 765 supplemented with 10% glycerol and the culture was grown until OD600 reached 0.6~0.8. Gene expression was induced by addition of isopropyl β-D-thiogalactoside (IPTG) to 1.0 mM (final concentration), and the culture was incubated for 48 hr at 20° C. Cell pellet was harvested and frozen in liquid nitrogen and thawed at 42° C. to lyse cell. To facilitate lysis, lysozyme was added in cell pellet. Protein expression was monitored by SDS-PAGE (7.5% gels) of total cellular protein and soluble protein, followed by colloidal coomassie blue staining.

REFERENCE

1. Abe Y, Suzuki T, Ono C, Iwamoto K, Hosobuchi M, Yoshikawa H. Molecular cloning and characterization of an ML-236B (compactin) biosynthetic gene cluster in *Penicillium citrinum*. 2002. Mol. Genet. Genomics. 267: 636-646.
2. Bedford, D. J., Schweizer, E., Hopwood, D. A., Khosla, C. Expression of a functional fungal polyketide synthase in the bacterium *Streptomyces coelicolor* A3(2). 1995. J. Bacteriol. 177, 4544-4548.
3. Endo A. Monacolin K, a new hypocholesterolemic agent produced by a *Monascus* species. J Antibiot (Tokyo) 1979, August; 32(8):852-4.
4. Endo A, Komagata D, Shimada H. Monacolin M, a new inhibitor of cholesterol biosynthesis. J Antibiot (Tokyo) 1986, December; 39(12):1670-3.
5. Endo A, Hasumi K, Negishi S. Monacolins J and L, new inhibitors of cholesterol biosynthesis produced by *Monascus ruber*. J Antibiot (Tokyo) 1985, March; 38(3): 420-2.
6. Endo A, Hasumi K, Nakamura T, Kunishima M, Masuda M. Dihydromonacolin L and monacolin X, new metabolites which inhibit cholesterol biosynthesis. J Antibiot (Tokyo) 1985, March; 38(3):321-7.
7. Gokhale, R. S., Tsuji, S. Y., Cane, D. E., Khosla, C. Dissecting and exploiting intermodular communication in polyketide synthases. 1999. Science. 284, 482-485.
8. Hendrickson L, Davis C R, Roach C, Nguyen D K, Aldrich T, McAda P C & Reeves C D. Lovastatin biosynthesis in *Aspergillus terreus*: characterization of blocked mutants, enzyme activities and a multifunctional polyketide synthase gene. 1999, Chem. Biol. 6: 429-439.
9. Hutchinson C. R., Kennedy J., Park C., Kendrew S., Auclair K. and Vederas J. Aspects of the biosynthesis of non-aromatic fungal by iterative polyketide synthases. Antonie van Leeuwenhoek 2000, 78:287-295.
10. Kennedy J, Auclair K, Kendrew S G, Park C, Vederas J C, Hutchinson C R. Modulation of polyketide synthase activity by accessory proteins during lovastatin biosynthesis. Science 1999, May 21; 284(5418):1368-72.
11. Komagata D, Shimada H, Murakawa S, Endo A. Biosynthesis of monacolins: conversion of monacolin L to monacolin J by a monooxygenase of *Monascus ruber*. J. Antibiot (Tokyo) 1989, March; 42(3):407-12.
12. McDaniel R, Thamchaipenet A, Gustafsson C, Fu H, Betlach M, Ashley G: Multiple genetic modifications of the erythromycin polyketide synthase to produce a library of novel 'unnatural' natural products. Proc Natl Acad Sci USA 1999, 96:1846-1851.
13. Mootz, H. D., Finking, R., Marahiel, M. A. 4'-Phosphopantetheine transfer in primary and secondary metabolism of *Bacillius subtilis*. 2001. J. Biol. Chem. 40, 37289-37298.
14. Nicholson T P, Rudd B A, Dawson M, Lazarus C M, Simpson T J, Cox R J. Design and utility of oligonucleotide gene probes for fungal polyketide synthases. Chem Biol 2001, February; 8(2):157-78.
15. O'Hagan D. Biosynthesis of fatty acid and polyketide me-tabolites. Nat Prod Rep. 2001, 12:1-32.
16. Pfeifer, B. A., Admiraal, S. J., Gramajo, H., Cane, D. E., Khosla, C. Biosynthesis of complex polyketides in a metabolically engineered strain of *E. coli*. 2001. Science. 291, 1790-1792.

What is claimed is:

1. An isolated DNA molecule, comprising a polynucleotide which is mkA and comprises SEQ ID NO: 2.

2. The isolated DNA molecule as claimed in claim 1, wherein the polynucleotide encodes a polypeptide comprising β-ketoacyl synthase, acetyl transferase, dehydratase, methyltransferase, ketoreductase, and acyl carrier protein activities.

3. The isolated DNA molecule as claimed in claim 1, wherein the polynucleotide encodes a polypeptide having nonaketide synthase activity.

4. A shuttle vector comprising the isolated DNA molecule as claimed in claim 1.

5. An isolated DNA molecule, comprising a polynucleotide which is mkA and comprises SEQ ID NO: 19.

6. The isolated DNA molecule as claimed in claim 5, which encodes a polypeptide comprising β-ketoacyl synthase, acetyl transferase, dehydratase, methyltransferase, ketoreductase, and acyl carrier protein activities.

7. The isolated DNA molecule as claimed in claim 5, wherein the polypeptide has nonaketide synthase activity.

8. An expression vector comprising the isolated DNA molecule as claimed in claim 5.

9. A cell transformed with a polynucleotide which is mkA and comprises SEQ ID NO: 2 or 19.

10. The cell as claimed in claim 9, wherein the cell is a bacterium, a yeast, an animal cell, an insect cell, a plant cell, or a filamentous fungus.

11. The cell as claimed in claim 9, wherein the cell is *Monascus* sp.

12. The cell as claimed in claim 9, wherein the cell is selected from a group consisting of *Monascus pilosus, Monascus ruber*, and *Monascus purpureus*.

13. An isolated DNA molecule, comprising a polynucleotide encoding a polypeptide comprises SEQ ID NO: 11.

14. The isolated DNA molecule as claimed in claim 13, wherein the polypeptide comprises β-ketoacyl synthase, acetyl transferase, dehydratase, methyltransferase, ketoreductase, and acyl carrier protein activities.

15. The isolated DNA molecule as claimed in claim 13, wherein the polypeptide has nonaketide synthase activity.

16. An expression vector comprising the isolated DNA molecule as claimed in claim 13.

* * * * *